United States Patent [19]

Yoshioka et al.

[11] Patent Number: 4,873,255

[45] Date of Patent: Oct. 10, 1989

[54] THIAZOLIDINONE DERIVATIVES, THEIR PREPARATION AND THEIR USE

[75] Inventors: Takao Yoshioka; Tsutomu Kanai; Yuichi Aizawa; Hiroyoshi Horikoshi; Kazuo Hasegawa, all of Hiromachi, Japan

[73] Assignee: Sankyo Company Limited, Tokyo, Japan

[21] Appl. No.: 151,807

[22] Filed: Feb. 3, 1988

[30] Foreign Application Priority Data

Feb. 4, 1987 [JP] Japan .................................. 62-22508

[51] Int. Cl.$^4$ .................. C07D 417/12; A61K 31/425
[52] U.S. Cl. .................................... 514/369; 514/337; 546/269; 548/183
[58] Field of Search ................. 514/369, 337; 548/183; 546/269

[56] References Cited

U.S. PATENT DOCUMENTS 4,572,912 2/1980 Yoshioka .............................. 514/369

Primary Examiner—Robert Gerstl
Attorney, Agent, or Firm—Frishauf, Holtz, Goodman & Woodward

[57] ABSTRACT

Thiazolidinone derivatives of formula (I):

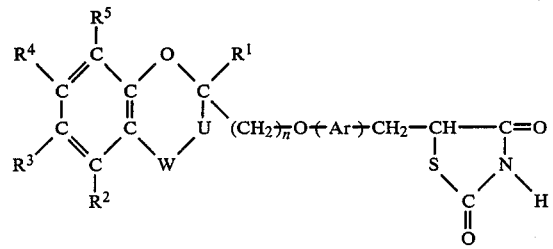

in which $R^1$, $R^2$, $R^3$, $R^4$ and $R^5$ are various atoms or organic groups, Ar is an aromatic group and n is an integer have valuable pharmacological activities including the ability to reduce blood glucose levels and blood lipid levels.

22 Claims, No Drawings

THIAZOLIDINONE DERIVATIVES, THEIR PREPARATION AND THEIR USE

BACKGROUND TO THE INVENTION

The present invention relates to a series of new thiazolidinone derivatives having valuable properties for the treatment and prophylaxis of diabetes. The invention also provides processes for preparing these compounds and compositions and methods using them.

The compounds of the present invention are of particular use for reducing blood glucose levels, and are therefore useful in the treatment of diabetes and complications thereof. They are also able to reduce blood lipid levels and can thus be used for the treatment of hyperlipemia.

Certain thiazolidinone derivatives having the ability to lower blood lipid and blood glucose levels are disclosed in U.S. Pat. No. 4 572 912 and in U.S. patent application Ser. No. 833 867 filed the 25th day of Feb. 1986. Other thiazolidinone derivatives having a similar type of activity are disclosed in European Patent Publication No. 8203; but such compounds are structurally less similar to those of the present invention.

We have now discovered a series of thiazolidinone derivatives which have the ability to reduce the levels of blood glucose and inhibit the activity of aldose reductase and which have the ability to reduce blood lipid levels. Moreover, it is a significant advantage of the compounds of the present invention that they have a very low toxicity and that the reduction in blood glucose levels is of a very long duration. As a result, the compounds of the invention are expected to be of considerable value in the treatment of diabetes and various complications thereof.

It is, therefore, an object of the present invention to provide a series of new compounds having the ability to reduce blood glucose levels.

It is a further object of the invention to provide pharmaceutical compositions for the treatment of diabetes and hyperlipemia containing such compounds as the active ingredient.

It is a still further object of the invention to provide methods for the treatment of humans and other animals employing such compounds.

BRIEF SUMMARY OF INVENTION

The present invention thus consists in compounds of formula (I):

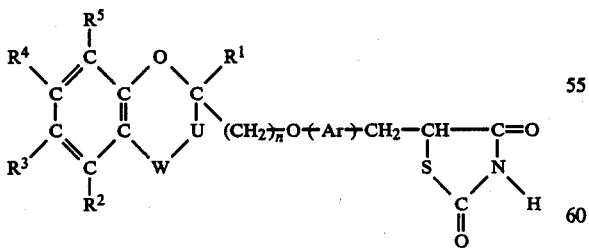

in which:

$R^1$ represents a hydrogen atom, a $C_1$–$C_{25}$ alkyl group, an aralkyl group, a $C_3$–$C_{10}$ cycloalkyl group or a substituted $C_3$–$C_{10}$ cycloalkyl group having at least one substituent selected from the group consisting of $C_1$–$C_6$ alkyl groups;

$R^2$, $R^4$ and $R^5$ are independently selected from the group consisting of: hydrogen atoms; $C_1$–$C_{25}$ alkyl groups; substituted $C_1$–$C_{25}$ alkyl groups having at least one substituent selected from the group consisting of substituents (a); aralkyl groups; $C_3$–$C_{10}$ cycloalkyl groups; substituted $C_3$–$C_{10}$ cycloalkyl groups having at least one substituent selected from the group consisting of $C_1$–$C_6$ alkyl groups; aryl groups; halogen atoms; hydroxy groups; protected hydroxy groups in which the protecting group is selected from the group consisting of substituents (b); $C_1$–$C_7$ alkanoyl groups; substituted $C_2$–$C_7$ alkanoyl groups having at least one substituent selected from the group consisting of substituents (c); arylcarbonyl groups; cycloalkylcarbonyl groups in which the cycloalkyl part is $C_3$–$C_{10}$; substituted cycloalkylcarbonyl groups in which the cycloalkyl part is $C_3$–$C_{10}$ and has at least one substituent selected from the group consisting of $C_1$–$C_6$ alkyl groups; carboxy groups; $C_2$–$C_7$ alkoxycarbonyl groups; aryloxycarbonyl groups; aralkyloxycarbonyl groups; nitro groups; groups of formula (II):

in which $R^7$ and $R^8$ are independently selected from the group consisting of hydrogen atoms, $C_1$–$C_6$ alkyl groups, aralkyl groups, $C_3$–$C_{10}$ cycloalkyl groups, aryl groups, $C_1$–$C_7$ alkanoyl groups, aralkanoyl groups, arylcarbonyl groups and $C_2$–$C_7$ alkoxycarbonyl groups, or $R^7$ and $R^8$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms. and groups of formula (III):

in which $R^{7'}$ and $R^{8'}$ are independently selected from the group consisting of hydrogen atoms, $C_1$–$C_6$ alkyl groups, aralkyl groups, $C_3$–$C_{10}$ cycloalkyl groups and aryl groups or $R^{7'}$ and $R^{8'}$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms;

$R^3$ represents a hydrogen atom, a $C_1$–$C_{25}$ alkyl group, a substituted $C_1$–$C_{25}$ alkyl group having at least one substituent selected from the group consisting of substituents (a), an aralkyl group, a $C_3$–$C_{10}$ cycloalkyl group, a substituted $C_3$–$C_{10}$ cycloalkyl group having at least one substituent selected from the group consisting of $C_1$–$C_6$ alkyl groups, an aryl group, a halogen atom, a $C_1$–$C_7$ alkanoyl group, a substituted $C_2$–$C_7$ alkanoyl group having at least one substituent selected from the group consisting of substituents (c), an arylcarbonyl group, a cycloalkylcarbonyl group in which the cycloalkyl part is $C_3$-$C_{10}$, a substituted cycloalkylcarbonyl group in which the cycloalkyl part is $C_3$-$C_{10}$ and has at least one substituent selected from the group consisting of $C_1$-$C_6$ alkyl groups, a carboxy group, a $C_2$-$C_7$ alkoxycarbonyl group, an aryloxycarbonyl group, an aralkyloxycarbonyl group, a nitro group, a group of formula (II) as defined or a group of formula (III) as defined above; or $R^3$ represents a hydroxy group or a protected hydroxy group in which the protecting group is selected from the group consisting of substituents (b), provided that at least one of $R^2$, $R^4$ and $R^5$ represents a substituted alkyl group having at least one substituent selected from the group consisting of substituents (a), a halogen atom, a hydroxy group, a substituted alkoxy group having at least one substituent selected from the group consisting of substituents (c), a $C_1$-$C_7$ alkanoyloxy group, a substituted $C_2$-$C_7$ alkanoyloxy group having at least one substituent selected from the group consisting of substituents (c), an arylcarbonyloxy group, a sulfoxy group, a $C_1$-$C_7$ alkanoyl group, a substituted $C_2$-$C_7$ alkanoyl group having at least one substituent selected from the group consisting of substituents (c), a cycloalkylcarbonyl group in which the cycloalkyl part is $C_3$-$C_{10}$, a substituted cycloalkylcarbonyl group in which the cycloalkyl part is $C_3$-$C_{10}$ and has at least one substituent selected from the group consisting of $C_1$-$C_6$ alkyl groups, an arylcarbonyl group, a carboxy group, a $C_2$-$C_7$ alkoxycarbonyl group, an aryloxycarbonyl group, an aralkyloxycarbonyl group, a nitro group, a group of formula (II) as defined above or a group of formula (III) as defined above;

Ar represents a divalent aromatic carbocyclic group or a divalent aromatic heterocyclic group;

W represents a methylene group, a carbonyl group, a group of formula $>$CH—OY
in which Y represents a hydrogen atom, a $C_1$-$C_7$ alkanoyl group or an arylcarbonyl group, or
a group of formula $>$C=N-OV
in which V represents a hydrogen atom, a $C_1$-$C_6$ alkyl group, a substituted $C_1$-$C_6$ alkyl group having at least one substituent selected from the group consisting of substituents (c), a $C_1$-$C_7$ alkanoyl group or an arylcarbonyl group;

U represents a single bond or a methylene group;

or, when W represents a carbonyl group or said group of formula $>$C=N-OV, U, $R^1$ and the carbon atom to which $R^1$ is attached may together represent a group of formula -CH=C$<$;

or W-U may represent a carbon-carbon double bond; and

N represents an integer from 1 to 10;

said aralkyl groups have an alkyl portion containing from 1 to 6 carbon atoms and an aryl portion as defined below, the alkyl portion being unsubstituted or having at least one substituent selected from the group consisting of substituents (c);

substituents (a):

hydroxy groups; protected hydroxy groups in which the protecting group is selected from the group consisting of substituents (b); $C_1$-$C_7$ aliphatic carboxylic acyl groups; $C_2$-$C_7$ aliphatic carboxylic acyl groups having at least one substituent selected from the group consisting of substituents (c); arylcarbonyl groups; cycloalkylcarbonyl groups in which the cycloalkyl part is $C_3$-$C_{10}$; substituted cycloalkylcarbonyl groups in which the cycloalkyl part is $C_3$-$C_{10}$ and having at least one substituent selected from the group consisting of $C_1$-$C_6$ alkyl groups; carboxy groups; $C_2$-$C_7$ alkoxycarbonyl groups; aryloxycarbonyl groups; aralkyloxycarbonyl groups; hydroxyimino groups; protected hydroxyimino groups in which the protecting group is selected from the group consisting of substituents (b); groups of formula (II) as defined above; and groups of formula (III) as defined above;

substituents (b):

$C_1$-$C_6$ alkyl groups, substituted $C_1$-$C_6$ alkyl groups having at least one substituent selected from the group consisting of substituents (c), $C_1$-$C_7$ aliphatic carboxylic acyl groups, substituted $C_2$-$C_7$ aliphatic carboxylic acyl groups having at least one substituent selected from the group consisting of substituents (c), arylcarbonyl groups, $C_2$-$C_7$ alkoxycarbonyl groups, aryloxycarbonyl groups, groups of formula (III) as defined above and sulfo groups;

substituents (c):

carboxy groups, $C_2$-$C_7$ alkoxycarbonyl groups and aryl groups;

said aryl groups and the aryl parts of said aralkyl, arylcarbonyl, aryloxycarbonyl, aralkyloxycarbonyl and divalent aromatic groups being $C_6$-$C_{14}$ carbocyclic aryl groups which are unsubstituted or have at least one substituent selected from the group consisting of substituents (d);

said heterocyclic groups, heterocyclic parts of said heterocyclic acyl and acyloxy groups and said divalent heterocyclic aromatic groups having from 5 to 14 ring atoms, of which from 1 to 5 are heteroatoms selected from the group consisting of nitrogen, oxygen and sulfur hetero-atoms, said heterocyclic groups being unsubstituted or having at least one substituent selected from the group consisting of substituents (d) and substituents (e);

substituents (d):

$C_1$-$C_6$ alkyl groups, $C_1$-$C_6$ alkoxy groups, hydroxy groups, sulfoxy groups, halogen atoms, nitro groups, groups of formula (II), as defined above, $C_1$-$C_7$ aliphatic carboxylic acyl groups, $C_7$-$C_{11}$ aromatic carboxylic acyl groups, $C_1$-$C_7$ aliphatic carboxylic acyloxy groups and $C_7$-$C_{11}$ arylcarbonyloxy groups in which the aryl part is unsubstituted or has at least one substituent selected from the group consisting of $C_1$-$C_6$ alkyl groups, $C_1$-$C_6$ alkoxy groups and halogen atoms;

substituents (e):

aryl groups and oxygen atoms; and pharmaceutically acceptable salts thereof.

The invention still further provides a pharmaceutical composition comprising a compound of formula (I) or a pharmaceutically acceptable salt thereof in admixture with a pharmaceutically acceptable carrier or diluent.

The invention still further provides a method of reducing blood lipid and blood glucose levels in an animal, especially a mammal, e.g. a human being, by administering to said animal an effective amount of a compound of formula (I) or a pharmaceutically acceptable salt thereof.

The invention still further provides processes for preparing the compounds of the invention, as described in greater detail hereafter.

DETAILED DESCRIPTION OF INVENTION

In the compounds of the present invention, where $R^1$ represents an alkyl group, this may be a straight or branched chain alkyl group having from 1 to 25 carbon atoms. Specific examples of such alkyl groups which may be represented by $R^1$ include the methyl, ethyl, propyl, isopropyl, butyl, isobutyl, sec-butyl, pentyl, isopentyl, 2-methylbutyl, 1-ethylpropyl, neopentyl, 2-methylbutyl, 1-ethylpropyl, hexyl, isohexyl, neohexyl, 1-methylpentyl, 3-methylpentyl, 1,3-dimethylbutyl, 2-ethylbutyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, heptadecyl, octadecyl, nonadecyl, icosyl, 3,7,11,15-tetramethylhexadecyl, docosyl and pentacosyl groups, of which the $C_1$–$C_{10}$ alkyl groups are more preferred, and the $C_1$–$C_4$ alkyl groups, especially the methyl and ethyl groups, are most preferred.

Where $R^1$, $R^7$, $R^{7'}$, $R^8$ or $R^{8'}$ represents an aralkyl group, the alkyl part is $C_1$–$C_6$ and the aryl part has from 6 to 14, more preferably from 6 to 10, ring atoms. More preferably, the alkyl part is $C_1$–$C_3$, and still more preferably $C_1$–$C_2$, the methyl group being most preferred. The aryl part is still more preferably a phenyl or naphthyl group, the phenyl group being most preferred. The alkyl part may be substituted by one or more of substituents (c), but is preferably unsubstituted, whilst the aryl part may be unsubstituted or have at least one, and preferably from 1 to 7 and more preferably from 1 to 3, substituents selected from the group consisting of substituents (d), as defined above and exemplified herein. Examples of such aralkyl groups include the benzyl, phenethyl, 1-phenylethyl, 3-phenylpropyl, 2-phenylpropyl, 1-phenylpropyl, 4-phenylbutyl, 1-naphthylmethyl and 2-naphthylmethyl groups, and substituted analogs thereof.

Where $R^1$, $R^7$, $R^{7'}$, $R^8$ or $R^{8'}$ represents a cycloalkyl group, this has from 3 to 10 ring carbon atoms, preferably from 5 to 8 ring atoms, and more preferably from 5 to 7 ring carbon atoms. Such groups may be unsubstituted or have at least one substituent selected from the group consisting of $C_1$–$C_6$ alkyl groups, more preferably $C_1$–$C_3$ alkyl groups, e.g. the methyl, ethyl, propyl, isopropyl, butyl, isobutyl, sec-butyl, t-butyl, pentyl, isopentyl, neopentyl, 2-methylbutyl, 1-ethylpropyl, hexyl, isohexyl, neohexyl, 1-methylpentyl, 3-methylpentyl, 1,3-dimethylbutyl and 2-ethylbutyl groups. Examples of such cycloalkyl groups include the cyclopentyl, cyclohexyl, cycloheptyl and cyclooctyl groups.

Where $R^2$, $R^3$, $R^4$ or $R^5$ represents an alkyl group, this has from 1 to 25, preferably from 1 to 20 and more preferably from 1 to 10, carbon atoms and may be a straight or branched chain group. Specific examples of such alkyl groups include the methyl, ethyl, propyl, isopropyl, butyl, isobutyl, t-butyl, pentyl, isopentyl, neopentyl, t-pentyl, hexyl, 1,1-dimethylbutl, 1,3-dimethylbutyl, heptyl, 1,1-diethylpropyl, octyl, 1-methylheptyl, 2-ethylhexyl, 1,1,3,3-tetramethylbutyl, nonyl, decyl, 3,7-dimethyloctyl, undecyl, dodecyl, pentadecyl and icosyl groups. Such groups may be substituted or unsubstituted, and, if substituted, the substituents are preferably selected from the group consisting of substituents (a), as defined above, and exemplified herein.

Where $R^2$, $R^3$, $R^4$ or $R^5$ represents an aralkyl or cycloalkyl group, these may be as exemplified above in relation to the similar groups which may be represented by $R^1$.

Where $R^2$, $R^3$, $R^4$, $R^5$, $R^7$, $R^{7'}$, $R^8$, $R^{8'}$, substituent (c) or substituent (e) represents an aryl group, this may be as defined above in relation to aryl groups generally, but preferably has from 6 to 10 ring carbon atoms, and is more preferably a phenyl or naphthyl (1- or 2-naphthyl) group, most preferably a phenyl group. Such groups may be substituted or unsubstituted, and, if substituted, the substituents are selected from the group consisting of substituents (d), as defined above and exemplified herein.

Where $R^2$, $R^3$, $R^4$, $R^5$ or substituent (d) represents a halogen atom, this is preferably a fluorine, chlorine, bromine or iodine atom, the fluorine and chlorine atoms being more preferred.

Where $R^2$, $R^3$, $R^4$ or $R^5$ represents a hydroxy group, this may be a free hydroxy group or it may be protected by one of the protecting groups listed as substituents (b), as defined above and exemplified herein.

Where $R^2$, $R^3$, $R^4$, $R^5$, $R^7$, $R^8$, V or Y represents an alkanoyl group, this has from 1 to 7 carbon atoms, including the carbon atom of the carbonyl group, and may be a straight or branched chain group. Examples include the formyl, acetyl, propionyl, butyryl, isobutyryl, valeryl, isovaleryl, pivaloyl, hexanoyl and heptanoyl groups. Of these, those alkanoyl groups having from 2 to 7 carbon atoms may, if desired, be substituted by one or more substituents selected from the group consisting of substituents (c), as defined above and exemplified herein. Where substituent (a), substituent (b) or substituent (d) represents an aliphatic acyl group or substituent (d) represents an aliphatic acyloxy group, this may be an alkanoyl group, as exemplified above or it may be an alkenoyl or alkynoyl group or the corresponding alkenoyloxy or alkynoyloxy group. Where it is such an alkenoyl or alkynoyl group, suitable examples include the acryloyl, propioloyl, methacryloyl, crotonoyl and isocrotonoyl groups or, for substituent (d), the corresponding alkenoyloxy or alkynoyloxy group. These groups likewise may, if desired, be substituted by one or more substituents selected from the group consisting of substituents (c), as defined above and exemplified herein.

Where $R^2$, $R^3$, $R^4$, $R^5$, $R^7$, $R^8$, V, Y, substituent (a), substituent (b) or substituent (d) represents an arylcarbonyl group or substituent (d) represents an arylcarbonyloxy group, the aryl part is as defined generally above, and is preferably a phenyl or naphthyl (1-or 2-naphthyl) group, which may be substituted or unsubstituted, and, if substituted, the substituents are selected from the group consisting of substituents (d), as defined generally above and exemplified herein. Preferred arylcarbonyl groups are the benzoyl and naphthylcarbonyl (1- and 2- naphthyl) groups and substituted analogs thereof, such as the benzoyl, p-toluoyl, o-toluoyl, m-toluoyl, o-chlorobenzoyl, p-chlorobenzoyl, m-chlorobenzoyl, p-nitrobenzoyl, m-fluorobenzoyl, p-aminobenzoyl, m-dimethylaminobenzoyl, m-methoxybenzoyl, p-methoxybenzoyl, o-methoxybenzoyl, 3,4-dichlorobenzoyl, 3,5-di-t-butyl-4-hydroxybenzoyl and 1- and 2- naphthoyl groups.

Where $R^2$, $R^3$, $R^4$, $R^5$ or substituent (a) represents a cycloalkylcarbonyl group, the cycloalkyl part is preferably as exemplified above in relation to the cycloalkyl groups which may be represented by $R^1$, and preferred examples of such cycloalkylcarbonyl groups include the cyclopentylcarbonyl, cyclohexylcarbonyl, cycloheptylcarbonyl and cyclooctylcarbonyl groups. Such groups may be substituted or unsubstituted, and, if substituted, the substituents are selected from the group consisting of $C_1$–$C_6$ alkyl groups, e.g. as exemplified in relation to substituents on cycloalkyl groups.

Where $R^2$, $R^3$, $R^4$, $R^5$, $R^7$, $R^8$, substituent (a), substituent (b) or substituent (c) represents an alkoxycarbonyl group, this has a total of from 2 to 7 carbon atoms, i.e. the alkoxy part has from 1 to 6 carbon atoms. Specific examples of such groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups.

Where $R^2$, $R^3$, $R^4$, $R^5$, substituent (a) or substituent (b) represents an aryloxycarbonyl group, the aryl part may be as defined generally above and examples of such groups include the phenoxycarbonyl and 1- and 2-naphthyloxycarbonyl groups, which may be substituted or unsubstituted, and, if substituted, the substituents are selected from the group consisting of substituents (d), as defined generally above and exemplified herein.

Where $R^2$, $R^3$, $R^4$, $R^5$ or substituent (a) represents an aralkyloxycarbonyl group, the aralkyl part may be any one of those aralkyl groups exemplified above in relation to $R^1$. Specific examples of such groups include the benzyloxycarbonyl group.

Where $R^2$, $R^3$, $R^4$ or $R^5$ represents a group of formula (II), as defined above, $R^7$ and $R^8$ are as defined above, and the resulting group may be an amino group or a nitrogen-containing heterocyclic group. Examples of such amino groups include the amino, methylamino, ethylamino, propylamino, isopropylamino, butylamino, sec-butylamino, pentylamino, isopentylamino, dimethylamino, diethylamino, dipropylamino, dibutylamino, dipentylamino, N-methyl-N-ethylamino, N-methyl-N-propylamino, N-ethyl-N-propylamino benzylamino, phenethylamino, cyclopropylamino, cyclopentylamino, cyclohexylamino and phenylamino groups. Where the groups of formula (II) is a nitrogen-containing heterocyclic group, the heterocyclic group contains from 5 to 10 ring atoms, of which at least one must be a nitrogen atom (provided by the nitrogen atom shown in the formula) and optionally another from 1 to 3, preferably 1 or 2, may be additional hetero-atoms selected from the group consisting of nitrogen, oxygen and sulfur heteroatoms. Examples of the nitrogen-containing heterocyclic groups (i.e. -$NR^7R^8$ where $R^7$, $R^8$ and the nitrogen atom together form an optionally substituted heterocyclic group), include the 1-pyrrolyl, 1-imidazolyl, 3-thiazolidinyl, 1-pyrrolidinyl, 1-pyrrolinyl, 1-imidazolinyl, 1-imidazolidinyl, 3-methyl-1-imidazolidinyl, 3-ethyl-1-imidazolidinyl, 3-t-butyl-1-imidazolidinyl, 3-acetyl-1-imidazolidinyl, 3-butyryl-1-imidazolidinyl, 3-valeryl-1-imidazolidinyl, 3-pivaloyl-1-imidazolidinyl, piperidino, 1-piperazinyl, 4-methyl-1-piperazinyl, 4-ethyl-1-piperazinyl, 4-propyl-1-piperazinyl, 4-butyl-1-piperazinyl, 4-pentyl-1-piperazinyl, 4-t-butyl-1-piperazinyl, 4-acetyl-1-piperazinyl, 4-formyl-1-piperazinyl, 4-propionyl-1-piperazinyl, 4-benzoyl-1-piperazinyl, 4-acryloyl-1-piperazinyl, 4-methacryloyl-1-piperazinyl, 4-propioloyl-1-piperazinyl, 4-butyryl-1-piperazinyl, 4-isovaleryl-1-piperazinyl, morpholino and 1-homopiperazinyl groups.

Where $R^2$, $R^3$, $R^4$ or $R^5$ represents a group of formula (III), as defined above, $R^{7'}$ and $R^{8'}$ are as defined above, and the resulting group may be a carbamoyl group or a nitrogen-containing heterocyclic acyl group. Examples of such carbamoyl groups include the carbamoyl, methylcarbamoyl, ethylcarbamoyl, propylcarbamoyl, isopropylcarbamoyl, butylcarbamoyl, sec-butylcarbamoyl, pentylcarbamoyl, isopentylcarbamoyl, dimethylcarbamoyl, diethylcarbamoyl, dipropylcarbamoyl, dibutylcarbamoyl, dipentylcarbamoyl, N-methyl-N-ethylcarbamoyl, N-methyl-N-propylcarbamoyl, N-ethyl-N-propylcarbamoyl, benzylcarbamoyl, phenethylcarbamoyl, cyclopropylcarbamoyl, cyclopentylcarbamoyl, cyclohexylcarbamoyl and phenylcarbamoyl groups. Where the group of formula (III) is a nitrogen-containing heterocyclic acyl group, the heterocyclic part contains from 5 to 10 ring atoms, of which at least one must be a nitrogen atom (provided by the nitrogen atom shown in the formula) and optionally another from 1 to 3, preferably 1 to 2, may be additional hetero-atoms selected from the group consisting of nitrogen, oxygen and sulfur hetero-atoms. Examples of the nitrogen-containing heterocyclic acyl groups (i.e. —$CONR^{7'}R^{8'}$ where $R^{7'}$, $R^{8'}$ and the nitrogen atom together form an optionally substituted heterocyclic group), include the 1-pyrrolylcarbonyl, 1-imidazolylcarbonyl, 3-thiazolidinylcarbonyl, 1-pyrrolidinylcarbonyl, 1-pyrrolinylcarbonyl, 1-imidazolinylcarbonyl, 1-imidazolidinylcarbonyl, 3-methyl-1-imidazolidinylcarbonyl, 3-ethyl-1-imidazolidinylcarbonyl, 3-t-butyl-1-imidazolidinylcarbonyl, 3-acetyl-1-imidazolidinylcarbonyl, 3-butyryl-1-imidazolidinylcarbonyl, 3-valeryl-1-imidazolidinylcarbonyl, 3-pivaloyl-1-imidazolidinylcarbonyl, piperidinocarbonyl, 1-piperazinylcarbonyl, 4-methyl-1-piperazinylcarbonyl, 4-ethyl-1-piperazinylcarbonyl, 4-propyl-1-piperazinylcarbonyl, 4-butyl-1-piperazinylcarbonyl, 4-pentyl-1-piperazinylcarbonyl, 4-t-butyl-1-piperazinylcarbonyl, 4-acetyl-1-piperazinylcarbonyl, 4-formyl-1-piperazinylcarbonyl, 4-propionyl-1-piperazinylcarbonyl, 4-benzoyl-1-piperazinylcarbonyl, 4-acryloyl-1-piperazinylcarbonyl, 4-methacryloyl-1-piperazinylcarbonyl, 4-propioloyl-1-piperazinylcarbonyl, 4-butyryl-1-piperazinylcarbonyl, 4-isovaleryl-1-piperazinylcarbonyl, morpholinocarbonyl and 1-homopiperazinylcarbonyl groups.

Where $R^7$, $R^{7'}$, $R^8$, $R^{8'}$ or V represents an alkyl group, this has from 1 to 6 carbon atoms and may be a straight or branched chain group. Examples of such groups include the methyl, ethyl, propyl, isopropyl, butyl, isobutyl, sec-butyl, t-butyl, pentyl, isopentyl, neopentyl, t-pentyl, 2-methylbutyl, 1-ethylpropyl, hexyl, isohexyl, neohexyl, 1-methylpentyl, 3-methylpentyl, 1,3-dimethylbutyl and 2-ethylbutyl groups. These groups may be substituted or unsubstituted, and, if substituted, the substituents are preferably selected from the group consisting of substituents (c), as defined above, and exemplified herein.

Where Ar represents a divalent carbocyclic aromatic group, this may be substituted or unsubstituted and has from 6 to 14, preferably from 6 to 10, ring carbon atoms. Examples of such divalent aromatic groups include the p-phenylene, o-phenylene and m-phenylene groups. Where such a group is substituted, it may have at least one of the substituents (d) defined above, but preferably $C_1$–$C_5$ alkyl groups (e.g. the methyl, ethyl, propyl, isopropyl, butyl or pentyl groups) or $C_1$–$C_5$ alkoxy groups (e.g. the methoxy, ethoxy, isopropoxy, t-butoxy or pentyloxy groups).

Where Ar represents a divalent aromatic heterocyclic group, the heterocyclic group is preferably a pyridine, furan, thiophene or pyrrole ring, which may be unsubstituted or have at least one substituent selected from the group consisting of substituents (d) and substituents (e), defined above, and the two free valences may be in a variety of positions. Specific examples of such groups are as follows, in which the first number given denotes the position of attachment of the heterocyclic group to the group of formula —$(CH_2)_n$—O—, whilst the second number given denotes the position of attachment of the heterocyclic group to the —$CH_2$—thiazolidine group: the pyrid-2,3-diyl, pyrid-2,4-diyl, pyrid-2,5-diyl, pyrid-2,6-diyl, pyrid-3,4-diyl, pyrid-3,5-diyl, pyrid-3,6-diyl, pyrid-3,2-diyl, pyrid-4,3-diyl, pyrid-4,2-diyl, furan-2,3-diyl, furan-2,4-diyl, furan-2,5-diyl, furan-3,2-diyl, furan-4,2-diyl, furan-3,4-diyl, thien-2,3-diyl, thien-2,4-diyl, thien-2,5-diyl, thien-3,2-diyl, thien-4,2-diyl, thien-3,4-diyl, pyrrol-2,3-diyl, pyrrol-2,4-diyl, pyrrol-2,5-diyl, pyrrol-3,2-diyl, pyrrol-4,2-diyl and pyrrol-3,4-diyl groups. Such groups may be unsubstituted or, if desired, may have at least one, and preferably only one, substituent selected from those substituents (d) and/or (e), defined above, but preferably $C_1$-$C_5$ alkyl groups (e.g. the methyl, ethyl, isopropyl, t-butyl or pentyl groups) or $C_1$-$C_5$ alkoxy groups (e.g. the methoxy, ethoxy, isopropoxy, t-butoxy or pentyloxy groups).

W may represent a methylene (—$CH_2$—) group, a carbonyl (>C=O) group, a group of formula >CH—OY (in which Y is as defined above) or a group of formula >C=NOV (where V is as defined above and may be the same as or different from the atom or group represented by $R^2$, $R^3$, $R^4$ and $R^5$). Examples of the hydroxy-protecting groups which may be represented by Y and V are as given above.

Alternatively, W and U may together form a double bond, e.g. as illustrated by the compounds of formula (I—4) described hereafter.

U preferably represents a methylene group. However, as mentioned above, it may form a double bond with W, or, when W represents a carbonyl group or a group of formula >C=N—OV, U may, together with $R^1$ and the carbon atom to which the group represented by $R^1$ is attached, form a group of formula —CH=C<. Alternatively, U may represent a carbon-carbon single bond, i.e. a direct bond between the carbon atom of the group represented by W and that to which the group represented by $R^1$ is attached.

n may be any integer from 1 to 10, but is preferably 1, 2 or 3.

Included amongst the preferred compounds of the invention are those compounds of formula (I) in which:

$R^1$ represents a hydrogen atom, or a straight or branched chain alkyl group having from 1 to 10 carbon atoms; more preferably a straight or branched chain alkyl group having from 1 to 5 carbon atoms; most preferably a methyl group or an ethyl group;

$R^2$, $R^3$, $R^4$ and $R^5$ are the same or different, and each represents a hydrogen atom, a straight or branched chain alkyl group having from 1 to 5 carbon atoms, a halogen atom (such as a fluorine, chlorine or bromine atom), an aliphatic acyl group having from 1 to 5 carbon atoms, a carboxy group, or an alkoxycarbonyl group having from 2 to 6 carbon atoms; more preferably a hydrogen atom, a straight or branched chain alkyl group having from 1 to 5 carbon atoms, a halogen atom (such as fluorine or chlorine), or an acyl group (such as acetyl or propionyl); most preferably a hydrogen atom, a methyl group, a fluorine atom or an acetyl group;

$R^2$, $R^4$ and $R^5$ are the same or different, and each represents a hydrogen atom, a straight or branched chain alkyl group having from 1 to 5 carbon atoms, a halogen atom (such as a fluorine, chlorine or bromine atom), a hydroxy group, an alkoxy group having from 1 to 5 carbon atoms which may be unsubstituted or substituted by a carboxy group or by an alkoxycarbonyl group having from 2 to 6 carbon atoms, an aliphatic acyloxy group having from 1 to 5 carbon atoms which may be unsubstituted or substituted by a carboxy group or by an alkoxycarbonyl group having from 2 to 6 carbon atoms, a benzoyloxy group which may be unsubstituted or substituted by a group selected from the group consisting of substituents (d), a sulfoxy group, or an aliphatic acyl group having from 1 to 5 carbon atoms; more preferably a hydrogen atom, an alkyl group having from 1 to 5 carbon atoms (such as a methyl, ethyl, propyl, isopropyl or t-butyl group), a halogen atom (such as a fluorine or chlorine atom), a hydroxy group, an alkoxy group (such as a methoxy or ethoxy group), an alkoxy group having from 1 to 4 carbon atoms which is substituted by a carboxy group (such as a carboxymethoxy or 1-carboxy-1-methylethoxy group), an alkoxy group having from 1 to 5 carbon atoms which is substituted by an alkoxycarbonyl group having from 2 to 6 carbon atoms (such as a methoxycarbonylmethoxy, ethoxycarbonylmethoxy or 1-ethoxycarbonyl-1-methylethoxy group), an acyloxy group (such as an acetoxy or benzoyloxy group), or an acyl group (such as an acetyl or propionyl group); most preferably a hydrogen atom, a methyl group, a hydroxyl group, a fluorine atom or an acetyl group;

W represents a methylene group, a carbonyl group or a group having the formula >C=N—O—V [in which V represents a hydrogen atom, an alkyl group having from 1 to 5 carbon atoms and substituted by a carboxyl group, (such as a carboxymethyl or 1-carboxy-1-methylethyl group), or an alkyl group having from 1 to 5 carbon atoms and substituted by an alkoxycarbonyl group having from 2 to 6 carbon atoms (such as an ethoxycarbonyl-methyl or 1-ethoxycarbonyl-1-methylethyl group)]; more preferably a methylene group, a carbonyl group or a group having the formula >C=N—OH; most preferably a methylene group or a carbonyl group; U represents a methylene group;

n is an integer of from 1 to 3; more preferably 1 or 2; most preferably 1;

Ar represents a p-phenylene group, an o-phenylene group or a m-phenylene group; more preferably a p-phenylene group; such groups represented by Ar may be unsubstituted or substituted by an alkyl group having from 1 to 5 carbon atoms, such as a methyl or isopropyl group.

In particular, examples of preferred groups which may be represented by $R^1$ include the methyl, propyl, isopropyl, butyl, isobutyl, pentyl, hexyl, heptyl, octyl, decyl, 2-(p-acetoxyphenyl)ethyl, benzyl, o-methylbenzyl, p-methoxybenzyl and m-chlorobenzyl groups and the hydrogen atom.

Examples of preferred groups which may be represented by $R^2$ include the methyl, isopropyl, hydroxymethyl, acetoxymethyl, formyl, carboxy, ethoxycarbonyl, hydroxy, methoxy, carboxymethoxy, ethoxycarbonylmethoxy, methoxycarbonyl, benzoyloxy and 2-methoxyethyl groups and the hydrogen and fluorine atoms.

Examples of preferred groups which may be represented by $R^3$ include the methyl, ethyl, isopropyl, butyl, sec-butyl, t-butyl, pentyl, t-pentyl, hexyl, 1,1,3,3-tetramethylbutyl, carboxy, ethoxycarbonyl, hydroxy, formyl, acetyl, 1-hydroxyiminoethyl, propionyl, isobutyryl, heptanoyl, benzoyl, p-methylbenzoyl, 2-naphthylcarbonyl, valeryl, pivaloyl, 3-carboxypropionyl, hydroxymethyl, nitro, amino, acetamido, dimethylamino, 4-methyl-1-piperazinyl and 4-acetyl-1-piperazinyl groups and the hydrogen, chlorine and fluorine atoms.

Examples of preferred groups which may be represented by $R^4$ include the methyl, t-butyl, hydroxy, carboxymethoxy, ethoxycarbonylmethoxy, t-butoxycarbonylmethoxy, 3-carboxypropoxy, 1-methyl-1-carboxypropoxy, formyloxy, acetoxy, sulfoxy, benzoyloxy, phenylacetoxy, 3-carboxypropionyloxy, acetyl, carboxy, methoxy, hydroxymethyl, ethoxycarbonyl and propionyloxy groups and the hydrogen, chlorine and fluorine atoms.

Examples of preferred groups which may be represented by $R^5$ include the methyl, isopropyl, t-butyl, butyl, acetyl, pentyl, octyl, methoxy, hydroxy, acetoxy, hydroxymethyl, carboxy, formyl, propyl, nitro, amino, acetamido and benzamido groups and the hydrogen, bromine and fluorine atoms.

Where the compounds of the present invention contain an acidic group in their molecule, for example where they contain a carboxy group [for example if substituent (a) or (c) represents a carboxy group] or where substituent (b) represents a sulfo (—SO$_3$H) group, then the compounds of the invention may form salts with cations. There is no limitation upon the nature of such salts, provided that, where they are to be used for therapeutic purposes, they are pharmaceutically acceptable, which, as is well-known in the art, means that they do not have reduced activity (or unacceptably reduced activity) or increased toxicity (or unacceptably increased toxicity) compared with the free compound of formula (I). Where, however, they are to be used for non-therapeutic purposes, e.g. as intermediates in the preparation of other compounds, even this limitation does not apply. Suitable salts include, for example: alkali metal salts, such as the sodium or potassium salts; alkaline earth metal salts, such as the calcium or magnesium salts; other metal salts, such as the aluminum or iron salts; salts with basic amino acids, such as the lysine or arginine salts; ammonium salts; and salts with organic amines, such as the cyclohexylammonium, diisopropylammonium and triethylammonium salts.

A particularly preferred salt is the sodium salt. In particular, we especially prefer a sodium salt of a compound in which $R^2$–$R^5$ are all hydrogen, U is methylene, W is methylene, Ar is 1,4-phenylene, $R^1$ is methyl and n is 1.

The compounds of the invention may also, depending upon the particular substituents, contain basic groups in their molecules and, in such a case, they can also form acid addition salts. As with the salts mentioned above, there is no particular limitation on the nature of the acid forming such a salt, provided that, where the compound is to be used for therapeutic purposes, the resulting salt is pharmaceutically acceptable. Examples of suitable acids include: inorganic acids, such as hydrochloric acid, sulfuric acid, nitric acid or phosphoric acid; organic carboxylic acids, such as acetic acid, tartaric acid, maleic acid, fumaric acid, malic acid, succinic acid, glutamic acid or aspartic acid; and organic sulfonic acids, such as p-toluenesulfonic acid or methanesulfonic acid.

Preferred classes of compound of the present invention are as follows:

(A) Those compounds of formula (I), in which:

$R^1$ represents a hydrogen atom or a $C_1$–$C_{10}$ alkyl group;

$R^2$, $R^4$ and $R^5$ are independently selected from the group consisting of: hydrogen atoms; $C_1$–$C_{10}$ alkyl groups; substituted $C_1$–$C_{10}$ alkyl groups having at least one substituent selected from the groups consisting of substituents (a): aralkyl groups; aryl groups; halogen atoms; hydroxy groups; protected hydroxy groups in which the protecting group is selected from the group consisting of substituents (b); $C_1$–$C_6$ alkanoyl groups; substituted $C_2$–$C_6$ alkanoyl groups having at least one substituent selected from the group consisting of substituents (c); arylcarbonyl groups; carboxy groups; $C_2$–$C_7$ alkoxycarbonyl groups; nitro groups; groups of formula (II), as defined above, and groups of formula (III), as defined above;

$R^3$ represents a hydrogen atom, a $C_1$–$C_{10}$ alkyl group, a substituted $C_1$–$C_{10}$ alkyl group having at least one substituent selected from the group consisting of substituents (a), an aralkyl group, an aryl group, a halogen atom, a $C_1$–$C_6$ alkanoyl group, a substituted $C_2$–$C_6$ alkanoyl group having at least one substituent selected from the group consisting of substituents (c), an arylcarbonyl group, a carboxy group, a $C_2$–$C_7$ alkoxycarbonyl group, a nitro group, a group of formula (II) as defined above or a group of formula (III) as defined above; or $R^3$ represents a hydroxy group or a protected hydroxy group in which the protecting group is selected from the group consisting of substituents (b), provided that at least one of $R^2$, $R^4$ and $R^5$ represents a substituted $C_1$–$C_6$ alkyl group having at least one substituent selected from the group consisting of substituents (a), a halogen atom, a hydroxy group, a substituted $C_1$–$C_6$ alkoxy group having at least one substituent selected from the group consisting of substituents (c), a $C_1$–$C_6$ alkanoyloxy group, a substituted $C_2$–$C_6$ alkanoyloxy group having at least one substituent selected from the group consisting of substituents (c), an arylcarbonyloxy group, a sulfoxy group, a $C_1$–$C_6$ alkanoyl group, a substituted $C_2$–$C_6$ alkanoyl group having at least one substituent selected from the group consisting of substituents (c), an arylcarbonyl group, a carboxy group, a $C_2$–$C_7$ alkoxycarbonyl group, a nitro group, a group of formula (II) as defined above or a group of formula (III) as defined above;

$R^7$ and $R^8$ are independently selected from the group consisting of hydrogen atoms, $C_1$–$C_6$ alkyl groups, aralkyl groups, aryl groups, $C_1$–$C_5$ alkanoyl groups and arylcarbonyl groups, or $R^7$ and $R^8$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms;

$R^{7'}$ and $R^{8'}$ are independently selected from the group consisting of hydrogen atoms, $C_1$–$C_6$ alkyl groups, aralkyl groups and aryl groups or $R^{7'}$ and $R^{8'}$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms, said heterocyclic group being unsubstituted or having at least one substituent selected from the group consisting of $C_1$–$C_6$ alkanoyl groups and arylcarbonyl groups;

Ar represents a phenylene group;

W represents a methylene group, a carbonyl group, a group of formula $>CH-OY$, in which Y is as defined above, or a group of formula $>C=N-OV$, in which V is as defined above;

U represents a methylene group;

or, when W represents a carbonyl group or said group of formula $>C=N-OV$, U, $R^1$ and the carbon atom to which $R^1$ is attached may together represent a group of formula $-CH=C<$;

or W–U may represent a carbon-carbon double bond; and

N represents the integer 1, 2 or 3; and pharmaceutically acceptable salts thereof.

(B) Those compounds of formula (I), in which:

$R^1$ represents a $C_1$–$C_4$ alkyl group;

$R^2$, $R^4$ and $R^5$ are independently selected from the group consisting of: hydrogen atoms; $C_1$–$C_4$ alkyl groups; halogen atoms; hydroxy groups; protected hydroxy groups in which the protecting group is selected from the group consisting of substituents (b); $C_1$–$C_5$ alkanoyl groups; benzoyl groups; carboxy groups; $C_2$–$C_7$ alkoxycarbonyl groups, nitro groups, and amino groups;

$R^3$ represents a hydrogen atom, a $C_1$–$C_4$ alkyl group, a halogen atom, a $C_1$–$C_5$ alkanoyl group, a benzoyl group, a carboxy group, a $C_2$–$C_7$ alkoxycarbonyl group, a nitro group or an amino group;

$R^3$ represents a hydroxy group or a protected hydroxy group in which the protecting group is selected from the group consisting of substituents (b), provided that at least one of $R^2$, $R^4$ and $R^5$ represents a halogen atom, a hydroxy group, a $C_1$–$C_5$ alkanoyloxy group, a benzoyloxy group, a sulfoxy group, a $C_1$–$C_5$ alkanoyl group, a benzoyl group, a carboxy group, a $C_2$–$C_6$ alkoxycarbonyl group, a nitro group or an amino group;

Ar represents a phenylene group;

W represents a methylene group, a carbonyl group or a group of formula $>CH-OH$;

U represents a methylene group;

or W–U may represent a carbon-carbon double bond; and n represents the integer 1, 2 or 3; and pharmaceutically acceptable salts thereof.

(C) Those compounds of formula (I), in which:

$R^1$ represents a $C_1$–$C_4$ alkyl group;

$R^2$, $R^4$ and $R^5$ are independently selected from the group consisting of: hydrogen atoms; $C_1$–$C_4$ alkyl groups, halogen atoms; hydroxy groups; protected hydroxy groups in which the protecting group is selected from the group consisting of substituents (f); $C_1$–$C_5$ alkanoyl groups; carboxy groups; $C_2$–$C_5$ alkoxycarbonyl groups; and nitro groups;

$R^3$ represents a hydrogen atom, a $C_1$–$C_4$ alkyl group, a halogen atom, a $C_1$–$C_5$ alkanoyl group, a carboxy group, a $C_2$–$C_5$ alkoxycarbonyl group or a nitro group; or $R^3$ represents a hydroxy group or a protected hydroxy group in which the protecting group is selected from the group consisting of substituents (f), provided that at least one of $R^2$, $R^4$ and $R^5$ represents a halogen atom, a hydroxy group, a benzoyloxy group, a $C_1$–$C_5$ alkanoyloxy group, a $C_1$–$C_5$ alkanoy group, a carboxy group, a $C_2$–$C_5$ alkoxycarbonyl group or a nitro group;

Ar represents an unsubstituted 1,4-phenylene group;

W represents a methylene group or a carbonyl group;

U represents a methylene group;

or W–U may represent a carbon-carbon double bond; and n represents the integer 1 or 2;

substituents (f):

$C_1$–$C_4$ alkyl groups having a single substituent selected from the group consisting of carboxy groups and $C_2$–$C_5$ alkoxycarbonyl groups, $C_1$–$C_5$ alkanoyl groups and benzoyl groups;

and pharmaceutically acceptable salts thereof.

(D) Those compounds of formula (I), in which:

$R^1$ represents a hydrogen atom or a $C_1$–$C_4$ alkyl group;

$R^2$ represents a hydrogen atom or a $C_1$–$C_4$ alkyl group;

$R^3$ represents a hydrogen atom, a $C_1$–$C_4$ alkyl group, a halogen atom, a $C_1$–$C_5$ alkanoyl group, a benzoyl group, a carboxy group, a $C_2$–$C_5$ alkoxycarbonyl group, a hydroxy group, an acetoxy group, a benzoyloxy group or a nitro group;

$R^4$ represents a hydrogen atom, a $C_1$–$C_4$ alkyl group, a halogen atom, a hydroxy group or a protected hydroxy group in which the protecting group is selected from the group consisting of substituents (f);

$R^5$ represents a hydrogen atom, a $C_1$–$C_4$ alkyl group or a nitro group;

PROVIDED THAT:

WHEN $R^3$ represents said hdyroxy group, said acetoxy group or said benzoyloxy group, THEN $R^4$ represents a halogen atom, a hydroxy group, a protected hydroxy group in which the protecting group is selected from the group consisting of substituents (f), defined below;

Ar represents a phenylene group;

W represents a methylene group or a carbonyl group;

U represents a methylene group;

or W–U may represent a carbon-carbon double bond; and n represents the integer 1, 2 or 3;

substituents (f):

$C_1$–$C_4$ alkyl groups having a single substituent selected from the group consisting of carboxy groups and $C_2$–$C_5$ alkoxycarbonyl groups, $C_1$–$C_5$ alkanoyl groups and benzoyl groups;

and pharmaceutically acceptable salts thereof.

(E) Those compounds of formula (I), in which:

$R^1$ represents a $C_1$–$C_4$ alkyl group;

$R^2$ represents a hydrogen atom or a $C_1$–$C_4$ alkyl group;

$R^3$ represents a hydrogen atom, a $C_1$–$C_4$ alkyl group, a halogen atom, a $C_2$–$C_5$ alkanoyl group, a carboxy group, a $C_2$–$C_5$ alkoxycarbonyl group or a hydroxy group;

$R^4$ represents a hydrogen atom, a $C_1$–$C_4$ alkyl group, a hydroxy group or a protected hydroxy group in which the protecting group is selected from the group consisting of substituents (f), defined above;

$R^5$ represents a hydrogen atom or a $C_1$–$C_4$ alkyl group;

PROVIDED THAT:

WHEN $R^3$ represents said hydroxy group, THEN $R^4$ represents a protected hydroxy group in which the protecting group is selected from the group consisting of substituted $C_1$–$C_4$ alkyl groups having at least one substituent selected from the group consisting of carboxy groups and $C_2$–$C_5$ alkoxycarbonyl groups;

Ar represents a phenylene group;

W represents a methylene group or a carbonyl group;

U represents a methylene group;

or W–U may represent a carbon–carbon double bond; and n represents the integer 1 or 2; and pharmaceutically acceptable salts thereof.

(F) Those compounds of formula (I), in which:
$R^1$ represents a $C_1$–$C_4$ alkyl group;
$R^2$ represents a hydrogen atom or a $C_1$–$C_4$ alkyl group;
$R^3$ represents a hydrogen atom, a $C_1$–$C_4$ alkyl group, a halogen atom, a $C_2$–$C_5$ alkanoyl group, a carboxy group or a $C_2$–$C_5$ alkoxycarbonyl group;
$R^4$ represents a hydrogen atom, a $C_1$–$C_4$ alkyl group, a hydroxy group or a protected hydroxy group in which the protecting group is selected from the group consisting of substituents (f), defined above;
$R^5$ represents a hydrogen atom or a $C_1$–$C_4$ alkyl group;
Ar represents an unsubstituted 1,4-phenylene group;
W represents a methylene group or a carbonyl group;
U represents a methylene group;
or W–U may represent a carbon–carbon double bond; and n represents the integer 1 or 2; and pharmaceutically acceptable salts thereof.

Examples of specific compounds of the invention are given in the following formulae (I-1) to (I-4), in which the substituents are as defined in the corresponding one of Tables 1 to 4 [i.e. Table 1 relates to formula (I-1), Table 2 relates to formula (I-2) and so on]. In the Tables, the following abbreviations are used:

| Ac | acetyl |
| Boz | benzoyl |
| Bu | butyl |
| iBu | isobutyl |

-continued

| sBu | sec-butyl |
| tBu | t-butyl |
| iByr | isobutyryl |
| Bz | benzyl |
| Dc | decyl |
| Et | ethyl |
| Etc | ethoxycarbonyl |
| Hp | heptyl |
| Hpo | heptanoyl |
| Hx | hexyl |
| Me | methyl |
| Mec | methoxycarbonyl |
| Np | naphthyl |
| Oc | octyl |
| Ph | phenyl |
| Phy | phenylene, e.g. 1,4-Phy = 1,4-phenylene |
| Piv | pivaloyl |
| Piz | piperazinyl |
| Pn | pentyl |
| tPn | t-pentyl |
| Pr | propyl |
| iPr | isopropyl |
| Prn | propionyl |
| Pyry | pyridinediyl |
| TMB | 1,1,3,3-tetramethylbutyl |
| Va | valeryl |

In Tables 3 and 4, in the groups represented by Ar, the lowest numbered position compatible with the appropriate positional numbering system is assigned to the atom in the group Ar attached to the oxygen atom [shown to the left of the group Ar in formula (I-3) or (I-4)].

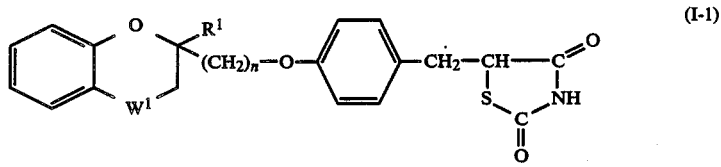
(I-1)

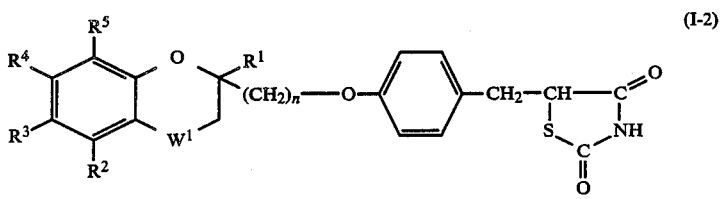
(I-2)

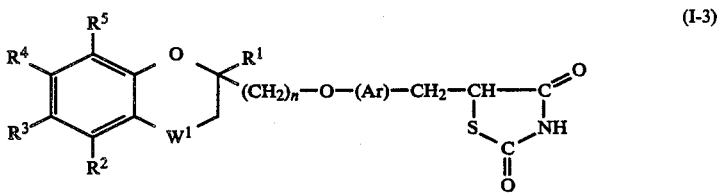
(I-3)

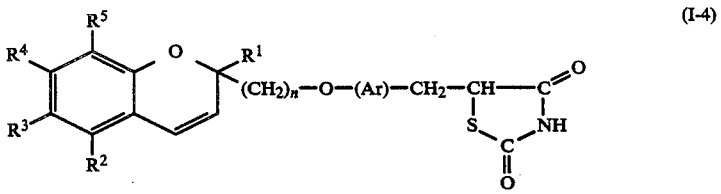
(I-4)

TABLE 1

| Cpd. No. | R¹ | W¹ | n |
|---|---|---|---|
| 1-1 | H | —CH— | 1 |
| 1-2 | H | >C=O | 1 |
| 1-3 | Me | —CH₂— | 1 |
| 1-4 | Me | —CH₂— | 2 |
| 1-5 | Me | >C=O | 1 |
| 1-6 | Me | >C=N—OH | 1 |
| 1-7 | 2-(p-AcOPh)Et | >C=N—OMe | 1 |
| 1-8 | o-MeBz | >C=N—OAc | 1 |
| 1-9 | Me | >C=N—OSO₃H | 1 |
| 1-10 | Me | >C=N—OCH₂COOH | 1 |
| 1-11 | Me | >C=N—OCH₂COOEt | 1 |
| 1-12 | Me | >C=N—O(CH₂)₃COOH | 1 |
| 1-13 | Bu | >C=N—O(CH₂)₆COOH | 1 |
| 1-14 | Me | >C=N—OCMe₂COOH | 1 |
| 1-15 | Me | >C=N—OCMe₂COOEt | 1 |

TABLE 2

| Cpd. No. | R¹ | R² | R³ | R⁴ | R⁵ | W¹ | n |
|---|---|---|---|---|---|---|---|
| 2-1 | H | Me | H | H | H | >C=O | 3 |
| 2-2 | Me | Me | H | H | H | —CH₂— | 1 |
| 2-3 | Me | Me | H | H | H | >C=O | 1 |
| 2-4 | Me | H | Me | H | H | —CH₂— | 1 |
| 2-5 | Me | H | H | Me | H | —CH₂— | 1 |
| 2-6 | Me | H | H | H | Me | —CH₂— | 1 |
| 2-7 | Me | Me | Me | H | H | —CH₂— | 1 |
| 2-8 | Me | H | Me | Me | H | —CH₂— | 1 |
| 2-9 | Me | H | H | Me | Me | —CH₂— | 1 |
| 2-10 | Me | Me | H | Me | H | —CH₂— | 1 |
| 2-11 | Hp | Me | H | Me | H | —CH₂— | 2 |
| 2-12 | Me | Me | H | Me | H | >C=O | 1 |
| 2-13 | Me | Me | H | Me | H | >C=N—OH | 1 |
| 2-14 | Me | Me | H | H | Me | —CH₂— | 1 |
| 2-15 | Me | H | Me | H | Me | —CH₂— | 1 |
| 2-16 | Me | Me | H | Me | Me | —CH₂— | 1 |
| 2-17 | Me | Me | H | Me | Me | >C=O | 1 |
| 2-18 | Me | Me | H | Me | Me | >C=N—OAc | 1 |
| 2-19 | Me | Me | Me | Me | Me | —CH₂— | 1 |
| 2-20 | Me | Me | Me | Me | Me | >C=O | 1 |
| 2-21 | Me | H | Et | H | H | —CH₂— | 1 |
| 2-22 | Me | H | iPr | H | H | —CH₂— | 1 |
| 2-23 | Me | H | H | H | iPr | —CH₂— | 1 |
| 2-24 | Hx | H | Bu | H | H | >C=O | 1 |
| 2-25 | Me | H | sBu | H | H | —CH₂— | 1 |
| 2-26 | Me | H | tBu | H | H | —CH₂— | 1 |
| 2-27 | Me | H | H | tBu | H | —CH₂— | 1 |
| 2-28 | Me | H | H | H | tBu | —CH₂— | 1 |
| 2-29 | Me | Me | H | H | iPr | —CH₂— | 1 |
| 2-30 | H | Me | H | H | iPr | >C=O | 2 |
| 2-31 | Me | iPr | H | H | Me | —CH₂— | 1 |
| 2-32 | Dc | H | Pn | H | H | >C=N—OH | 1 |
| 2-33 | Me | H | tPn | H | H | —CH₂— | 1 |
| 2-34 | Me | Me | H | H | tBu | —CH₂— | 1 |
| 2-35 | p-MeOBz | H | Me | H | tBu | —CH₂— | 1 |
| 2-36 | m-ClBz | H | Hx | H | H | —CH₂— | 1 |
| 2-37 | Me | H | TMB | H | H | —CH₂— | 1 |
| 2-38 | Me | H | tBu | H | tBu | —CH₂— | 1 |
| 2-39 | Pr | Me | tBu | H | tBu | —CH₂— | 1 |
| 2-40 | Me | F | H | H | H | —CH₂— | 1 |
| 2-41 | Me | H | F | H | H | —CH₂— | 1 |
| 2-42 | Me | H | F | H | H | —CH₂— | 2 |
| 2-43 | Me | H | F | H | H | >C=O | 1 |
| 2-44 | Me | H | F | H | H | >C=N—OH | 1 |
| 2-45 | Me | H | Etc | F | H | —CH₂— | 1 |
| 2-46 | Oc | Me | H | H | F | >C=N—OMe | 1 |
| 2-47 | Me | H | Cl | Cl | H | >C=O | 1 |
| 2-48 | Me | H | OH | Cl | H | >C=O | 1 |
| 2-49 | Bz | H | Cl | H | H | —CH₂— | 1 |
| 2-50 | Me | H | H | Cl | H | >C=O | 1 |
| 2-51 | Dc | H | H | H | Br | —CH₂— | 1 |
| 2-52 | Me | H | F | H | F | —CH₂— | 1 |
| 2-53 | iBu | H | F | H | F | —CH₂— | 1 |
| 2-54 | Me | H | F | H | F | >C=O | 1 |
| 2-55 | Me | H | H | F | F | —CH₂— | 1 |
| 2-56 | Me | H | H | F | F | >C=O | 1 |
| 2-57 | Me | H | Cl | F | H | >C=O | 1 |
| 2-58 | H | H | H | OH | H | —CH₂— | 1 |
| 2-59 | Me | H | H | OH | H | —CH₂— | 1 |
| 2-60 | H | H | H | OH | Me | —CH₂— | 1 |
| 2-61 | Me | H | H | OH | Me | —CH₂— | 1 |
| 2-62 | Me | H | H | OH | Me | —CH₂— | 2 |
| 2-63 | Me | H | H | OH | Me | >C=O | 1 |
| 2-64 | Me | H | H | OH | Me | >C=N—OH | 1 |
| 2-65 | Me | H | H | OH | Me | >C=N—OCH₂COOH | 1 |

TABLE 2-continued

| Cpd. No. | R¹ | R² | R³ | R⁴ | R⁵ | W¹ | n |
|---|---|---|---|---|---|---|---|
| 2-66 | Me | H | H | OCH₂COOH | Me | >C=N—OCH₂COOH | 1 |
| 2-67 | Me | H | H | OCH₂COOEt | Me | >C=N—OCH₂COOEt | 1 |
| 2-68 | Me | H | H | OCH₂COOH | Me | —CH₂— | 1 |
| 2-69 | Me | H | H | OCH₂COOEt | Me | —CH₂— | 1 |
| 2-70 | Me | H | H | OCH₂COOH | Me | >C=O | 1 |
| 2-71 | Me | H | H | OCH₂COOtBu | Me | >C=O | 1 |
| 2-72 | Me | H | H | O(CH₂)₃—COOH | Me | —CH₂— | 1 |
| 2-73 | Me | H | H | OCMe₂COOH | Me | —CH₂— | 1 |
| 2-74 | Me | H | H | OCHO | Me | —CH₂— | 1 |
| 2-75 | Me | H | H | OAc | Me | —CH₂— | 1 |
| 2-76 | Me | H | H | OSO₃H | Me | —CH₂— | 1 |
| 2-77 | iPr | H | Me | BozO | Me | —CH₂— | 1 |
| 2-78 | Hx | Me | Me | PhAcO | Bu | —CH₂— | 1 |
| 2-79 | Me | H | H | 3-HOOC—PrnO | Me | —CH₂— | 1 |
| 2-80 | Me | H | tBu | OH | Me | —CH₂— | 1 |
| 2-81 | Me | H | tBu | OH | Me | >C=O | 1 |
| 2-82 | H | H | Ac | OH | H | —CH₂— | 1 |
| 2-83 | Me | H | Ac | OH | H | —CH₂— | 1 |
| 2-84 | Me | H | H | OH | Ac | —CH₂— | 1 |
| 2-85 | Me | H | —CHO | OH | H | —CH₂— | 1 |
| 2-86 | Me | H | Ac | OH | Me | —CH₂— | 1 |
| 2-87 | Me | H | Ac | OH | Me | —CH₂— | 2 |
| 2-88 | Me | H | Ac | OH | Me | >C=O | 1 |
| 2-89 | Me | H | —C(Me)=NOH | OH | Me | >C=N—OH | 1 |
| 2-90 | Me | H | Prn | OH | Me | —CH₂— | 1 |
| 2-91 | Me | H | iByr | OH | Me | —CH₂— | 1 |
| 2-92 | Bu | Me | Hpo | OH | Me | —CH₂— | 1 |
| 2-93 | Me | H | Boz | OH | Me | —CH₂— | 1 |
| 2-94 | Me | H | p-MeBoz | OH | Me | —CH₂— | 1 |
| 2-95 | Me | H | 2-NpCO | OH | Me | —CH₂— | 1 |
| 2-96 | Me | H | Ac | OAc | Pn | —CH₂— | 1 |
| 2-97 | Bz | H | Piv | OBoz | Oc | —CH₂— | 1 |
| 2-98 | Me | H | 3-HOOC—Prn | OH | Me | —CH₂— | 1 |
| 2-99 | Me | H | Ac | OCHO | Me | —CH₂— | 1 |
| 2-100 | Me | H | Ac | OSO₃H | Me | —CH₂— | 1 |
| 2-101 | Me | H | H | H | OMe | —CH₂— | 1 |
| 2-102 | Me | H | H | H | OMe | >C=O | 1 |
| 2-103 | Me | CH₂OH | H | OH | OH | —CH₂— | 1 |
| 2-104 | Me | CH₂OH | H | OH | OH | >C=O | 1 |
| 2-105 | Me | CH₂OAc | H | OAc | OAc | —CH₂— | 1 |
| 2-106 | Me | CHO | H | OH | OH | —CH₂— | 1 |
| 2-107 | Me | COOH | H | OH | OH | —CH₂— | 1 |
| 2-108 | Me | Etc | H | OH | OH | —CH₂— | 1 |
| 2-109 | Me | H | CH₂OH | OH | OH | —CH₂— | 1 |
| 2-110 | Me | H | COOH | OH | OH | —CH₂— | 1 |
| 2-111 | Me | OH | CH₂OH | OH | H | —CH₂— | 1 |
| 2-112 | Me | OH | COOH | OH | H | —CH₂— | 1 |
| 2-113 | Me | H | OH | Ac | H | —CH₂— | 1 |
| 2-114 | Me | H | OH | Ac | H | >C=O | 1 |
| 2-115 | Me | H | OH | COOH | H | —CH₂— | 1 |
| 2-116 | Me | H | H | OMe | H | —CH₂— | 1 |
| 2-117 | Me | OMe | H | OMe | H | —CH₂— | 1 |
| 2-118 | Me | OCH₂—COOH | H | OCH₂—COOH | H | —CH₂— | 1 |
| 2-119 | Me | OCH₂—COOEt | H | OCH₂—COOEt | H | —CH₂— | 1 |
| 2-120 | Pn | H | H | H | CH₂OH | —CH₂— | 2 |
| 2-121 | Me | H | H | H | COOH | >C=O | 1 |
| 2-122 | Me | Me | H | H | CHO | —CH₂— | 1 |
| 2-123 | Me | CHO | H | H | CHO | —CH₂— | 1 |
| 2-124 | Me | H | H | CH₂OH | H | —CH₂— | 1 |
| 2-125 | Me | H | COOH | H | H | —CH₂— | 1 |
| 2-126 | Bz | Mec | H | H | H | —CH₂— | 1 |
| 2-127 | Me | OH | H | H | H | —CH₂— | 1 |
| 2-128 | Me | OH | H | H | H | >C=O | 1 |
| 2-129 | Bu | BozO | H | H | H | —CH₂— | 1 |
| 2-130 | Me | OMe | H | H | H | —CH₂— | 1 |
| 2-131 | Me | OCH₂—COOH | H | H | H | —CH₂— | 1 |
| 2-132 | Me | 2-MeOEt | OH | H | H | —CH₂— | 1 |
| 2-133 | Me | H | OH | Etc | H | —CH₂— | 1 |
| 2-134 | Me | Etc | OH | H | H | —CH₂— | 1 |
| 2-135 | Me | H | COOH | H | H | >C=O | 1 |
| 2-136 | Me | H | Etc | H | H | >C=O | 1 |
| 2-137 | Me | H | Etc | H | H | —CH₂— | 1 |
| 2-138 | Me | H | Ac | OH | Pr | —CH₂— | 1 |
| 2-139 | Me | H | Ac | OH | Pr | >C=O | 1 |

TABLE 2-continued

| Cpd. No. | $R^1$ | $R^2$ | $R^3$ | $R^4$ | $R^5$ | $W^1$ | $n$ |
|---|---|---|---|---|---|---|---|
| 2-140 | Me | H | $NO_2$ | H | H | $-CH_2-$ | 1 |
| 2-141 | Me | H | $NO_2$ | H | H | $>C=O$ | 1 |
| 2-142 | Me | H | $NO_2$ | Me | H | $-CH_2-$ | 1 |
| 2-143 | Me | H | H | H | $NO_2$ | $-CH_2-$ | 1 |
| 2-144 | Me | H | F | H | $NO_2$ | $-CH_2-$ | 1 |
| 2-145 | Me | Me | Me | Me | $NO_2$ | $-CH_2-$ | 2 |
| 2-146 | Me | H | $NH_2$ | H | H | $-CH_2-$ | 1 |
| 2-147 | Me | H | $NMe_2$ | H | H | $>C=O$ | 1 |
| 2-148 | Me | H | 4-Me-1-Piz | H | H | $-CH_2-$ | 1 |
| 2-149 | Me | H | 4-Ac-1-Piz | H | H | $-CH_2-$ | 2 |
| 2-150 | Me | H | H | H | $NH_2$ | $-CH_2-$ | 1 |
| 2-151 | Me | H | H | H | NHAc | $-CH_2-$ | 1 |
| 2-152 | Me | H | NHAc | H | H | $>C=O$ | 1 |
| 2-153 | Me | Me | Me | Me | NHBoz | $-CH_2-$ | 1 |
| 2-154 | Me | H | Etc | H | H | $-CHOH-$ | 1 |

TABLE 3

| Cpd. No. | $R^1$ | $R^2$ | $R^3$ | $R^4$ | $R^5$ | $W^1$ | Ar | $n$ |
|---|---|---|---|---|---|---|---|---|
| 3-1 | H | H | H | H | H | $-CH_2-$ | 3-Me—1,4-Phy | 1 |
| 3-2 | Me | H | H | OH | H | $-CH_2-$ | 5-Me—1,3-Phy | 1 |
| 3-3 | Me | H | Ac | OH | H | $-CH_2-$ | 1,3-Phy | 1 |
| 3-4 | Pr | H | Va | OPrn | H | $-CH_2-$ | 2-Cl—1,4-Phy | 1 |
| 3-5 | Me | H | H | H | H | $-CH_2-$ | 6-Me—1,3-Phy | 1 |
| 3-6 | Me | H | H | H | H | $-CH_2-$ | 6-Me—1,3-Phy | 2 |
| 3-7 | Me | H | H | H | H | $>C=O$ | 6-Me—1,3-Phy | 1 |
| 3-8 | Me | Me | H | H | Me | $>C=O$ | 3-MeO—1,4-Phy | 1 |
| 3-9 | Me | H | H | H | H | $>C=NOH$ | 6-Me—1,3-Phy | 1 |
| 3-10 | Me | H | OH | COOH | H | $-CH_2-$ | 6-Me—1,3-Phy | 1 |
| 3-11 | Me | H | H | H | H | $-CH_2-$ | 2,5-Pyry | 1 |

TABLE 4

| Cpd. No. | $R^1$ | $R^2$ | $R^3$ | $R^4$ | $R^5$ | Ar | $n$ |
|---|---|---|---|---|---|---|---|
| 4-1 | H | H | H | H | H | 1,4-Phy | 1 |
| 4-2 | Me | H | H | H | H | 1,4-Phy | 1 |
| 4-3 | Me | Me | H | Me | H | 1,4-Phy | 1 |
| 4-4 | Me | Me | Me | Me | Me | 1,4-Phy | 1 |
| 4-5 | Me | Me | OH | Cl | Me | 1,4-Phy | 1 |
| 4-6 | Me | H | COOH | H | H | 1,4-Phy | 1 |
| 4-7 | Me | H | Etc | H | H | 1,4-Phy | 1 |
| 4-8 | Me | Me | Etc | H | Me | 5-Me—1,3-Phy | 1 |
| 4-9 | Me | H | H | OH | Me | 1,4-Phy | 1 |
| 4-10 | Me | H | Ac | OH | Me | 1,4-Phy | 1 |
| 4-11 | Me | H | Ac | OH | Pr | 1,4-Phy | 1 |
| 4-12 | Me | H | F | H | H | 1,4-Phy | 1 |
| 4-13 | Me | H | H | $OCH_2COOH$ | Me | 1,4-Phy | 1 |
| 4-14 | Me | Me | Me | $OCMe_2COOH$ | Me | 1,4-Phy | 1 |
| 4-15 | Me | H | $NO_2$ | H | H | 1,4-Phy | 1 |
| 4-16 | Me | H | H | H | $NO_2$ | 1,4-Phy | 1 |
| 4-17 | Me | H | $NH_2$ | H | H | 1,4-Phy | 1 |
| 4-18 | Me | H | $NH_2$ | Me | H | 1,4-Phy | 2 |
| 4-19 | Me | H | H | H | $NH_2$ | 1,4-Phy | 1 |

Of the compounds listed above, the following are preferred: Compounds No. 1-3, 1-5, 2-10, 2-12, 2-19, 2-41, 2-43, 2-48, 2-61, 2-63, 2-68, 2-70, 2-71, 2-73, 2-88, 2-125, 2-135, 2-136, 2-137, 2-139, 2-140, 2-143, 2-146, 2-154 and 4-7, and their pharmaceutically acceptable salts. More preferred compounds are Compounds No. 1-3, 1-5, 2-19, 2-41, 2-61, 2-70, 2-88, 2-125, 2-135, 2-140, 2-143 and 2-146, and their pharmaceutically acceptable salts. The most preferred compounds are Compounds No.:

1-3.  5-[4-(2-Methylchroman-2-ylmethoxy)benzyl]-thiazolidine-2,4-dione
2-19. 5-[4-(2,5,6,7,8-Pentamethylchroman-2-ylmethoxy)benzyl]thiazolidine-2,4-dione
2-70. 2-[4-(2,4-Dioxothiazolidin-5-ylmethy)phenoxymethyl]-2,8-dimethyl-4-oxochroman-7-yloxyacetic acid
2-125. 2-[4-(2,4-Dioxothiazolidin-5-ylmethyl)phenoxymethyl]-2-methylchroman-6-carboxylic acid
2-135. 2-[4-(2,4-Dioxothiazolidin-5-ylmethyl)phenoxymethyl]-2-methyl-4-oxochroman-6-carboxylic acid and their pharmaceutically acceptable salts, most especially Compounds No. 1-3 and 2-125, and their pharmaceutically acceptable salts, particularly the sodium salt of Compound No. 1-3.

Reaction Scheme A

The compounds of the invention may be prepared as illustrated in the following Reaction Scheme A:

Reaction Scheme A

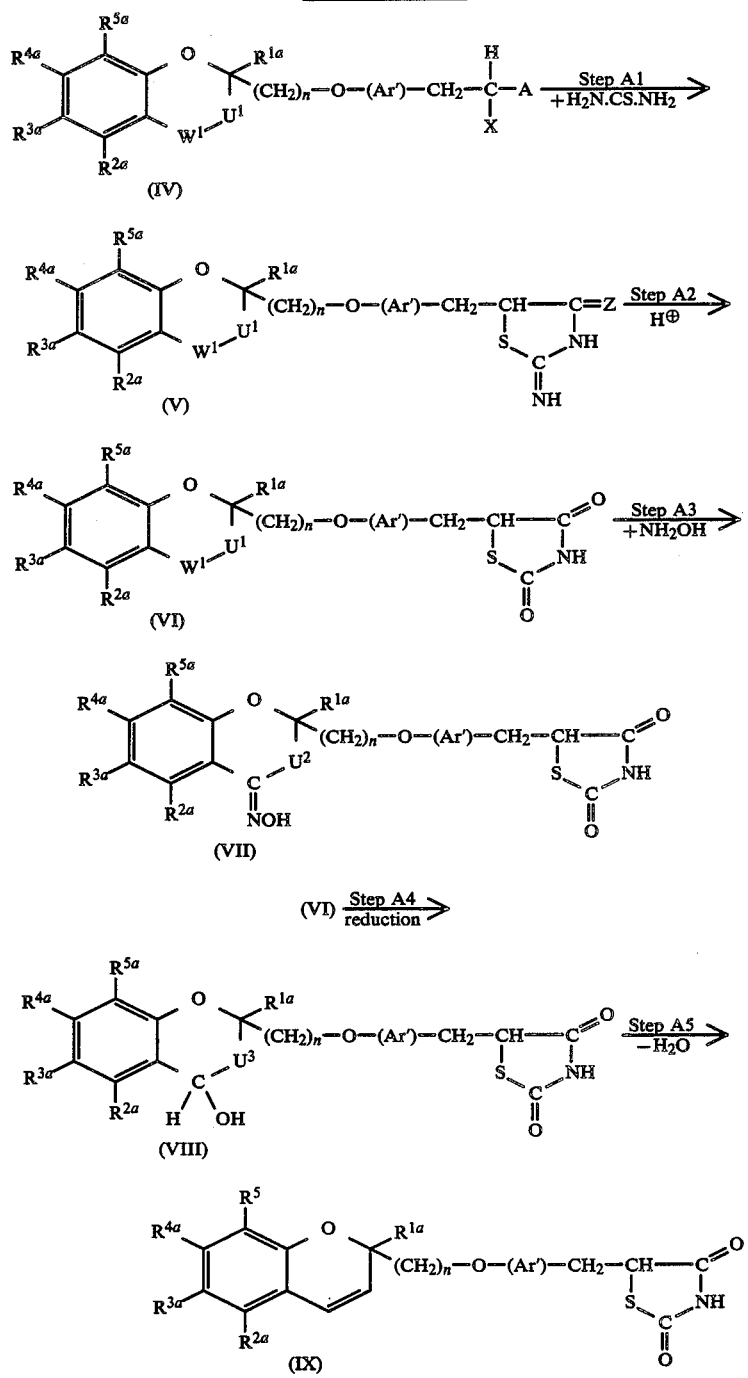

In the above formulae:

n is as defined above;

$R^{1a}$, $R^{2a}$, $R^{3a}$, $R^{4a}$, $R^{5a}$ and Ar' represent any of the groups or atoms hereinbefore defined for $R^1$, $R^2$, $R^3$, $R^4$, $R^5$ and Ar, respectively, except that, if any such group represented by $R^1$, $R^2$, $R^3$, $R^4$, $R^5$ or Ar is or includes a sulfoxy group, an alkoxycarbonyloxy group or an aryloxycarbonyloxy group, then $R^{1a}$, $R^{2a}$, $R^{3a}$, $R^{4a}$, $R^{5a}$ and Ar' do not represent or include any such group;

$W^1$ represents a methylene (—$CH_2$—) group or a carbonyl (>C=O) group]

$U^1$ represents a single bond or a methylene group, or, when $W^1$ represents a carbonyl group, $U^1$ may form a double bond together with $R^{1a}$;

$U^2$ represents a single bond or a methylene group, or $U^2$ may form a double bond together with $R^{1a}$;

$U^3$ represents a single bond or a methylene group;

A represents a cyano group, a carboxy group, a $C_2$-$C_7$ alkoxycarbonyl group (such as a methoxycarbonyl, ethoxycarbonyl, propoxycarbonyl, isopropoxycarbonyl or butoxycarbonyl group), a carbamoyl group or a group of formula —COOM$_{(m)}$ where M represents a cation (such as sodium, potassium, calcium or aluminum) or an equivalent cation (such as ammonium) and m represents the reciprocal of the valence of the cation represented by M;

X represents a halogen atom, such as chlorine, bromine or iodine, and

Z represents an oxygen atom or an imino group.

Step A1

In the first step of this reaction scheme, the compound of formula (IV), used as the starting material in this reaction scheme, is reacted with thiourea, which has the formula:

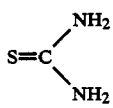

to give the compound of formula (V).

The reaction of the compound of formula (IV) with the thiourea is preferably effected in the presence of a solvent. The nature of the solvent is not critical, provided that it has no adverse effect upon the reaction. Suitable solvents include, for example: alcohols, such as methanol, ethanol, propanol, butanol or ethylene glycol monomethyl ether; ethers, such as tetrahydrofuran or dioxane; ketones, such as acetone; dimethyl sulfoxide; sulfones, such as sulfolane; and amides, such as dimethylformamide.

There is no criticality as to the molar ratio of the compound of formula (IV) to the thiourea and so conventional criteria apply to determine the most suitable proportions. Preferably the two reagents are employed in equimolar amounts or the thiourea is employed in excess, preferably a slight excess. The most suitable molar ratio of thiourea to compound of formula (IV) is from 1:1 to 2:1.

The reaction temperature is not critical to the invention, although the optimum temperature will vary, depending upon the nature of the reagents and the solvent employed. In general, we prefer to carry out the reaction of the boiling point of the solvent or at a temperature within the range from 80 to 150° C. The time required for the reaction may also vary, depending upon many factors, notably the reaction temperature and the nature of the reagents, but a period of from 1 to 20 hours will normally suffice.

If the compound of formula (IV) contains a hydroxy group, for example a phenolic hydroxy group in $R^{1a}$, $R^{2a}$, $R^{3a}$, $R^{4a}$, $R^{5a}$ or Ar', then we prefer that this hydroxy group should be protected prior to the reaction of Step A1, e.g. by reaction with an acyl group. Such reactions may be carried out by means well known per se, and the protecting group may subsequently be removed by equally well known reactions, at any convenient stage in the reaction sequence.

Step A2

This compound of formula (V) produced as described in Step A1 may immediately be hydrolized under the prevailing reaction conditions to give the compound of formula (IV); if it is not, then a separate hydrolysis step is required, to hydrolize the imino group at the 2-position of the thiazolidine ring and, where Z represents an imino group, to hydrolize that imino group also, to an oxygen atom, thereby giving the compound of formula (VI).

Where hydrolysis of the resulting compound of formula (V) is required as a separate step, this may be effected by heating the compound of formula (V) in a suitable solvent in the presence of water and of an acid. The nature of the solvent is not critical, provided that it has no adverse effect upon the reaction and examples of suitable solvents include: sulfolane; and alcohols, such as methanol, ethanol or ethylene glycol monomethyl ether. Suitable acids include such organic acids as acetic acid and such mineral acids as sulfuric acid or hydrochloric acid. The amount of acid added is not critical, but is preferably from 0.1 to 10 moles, more preferably from 0.2 to 3 moles, per mole of the compound of formula (V). The water or aqueous solvent employed in this hydrolysis is preferably added in stoichiometric excess with respect to the compound of formula (V), preferably a large excess. The reaction temperature is not particularly critical, although we prefer to carry out the reaction at a temperature of from 50 to 100° C., at which temperature the reaction will normally be essentially complete within a period of from 2 to 20 hours.

Where the compound of formula (V) contains an acyloxy group, the hydrolysis step will often hydrolize this to a hydroxy group.

Step A3

This step is optional and converts a compound of formula (VI) in which W represents a carbonyl group to a compound of formula (VII), or to a corresponding compound in which the hydroxy group of the hydroxyimino group is replaced by a group of formula $-OV^1$, in which $V^1$ represents any of the groups defined above in respect of V except a hydrogen atom.

The reaction is carried out by reacting the compound of formula (VI) with hydroxylamine or with an acylated or alkylated derivative thereof of formula:

(in which V is as defined above) or a salt thereof.

The nature of the hydroxylamine derivative depends upon the nature of the group =NOV which it is desired to introduce into the compound. The hydroxylamine derivative may be employed in the form of a salt thereof, for example a salt with a mineral acid, such as hydrochloric acid or sulfuric acid.

The reaction may be effected in the presence of an acid-binding agent. Where an acid-binding agent is employed, it is preferably an alkali metal hydroxide (such as potassium hydroxide) or an alkali metal carbonate (such as sodium carbonate or potassium carbonate).

The reaction is preferably effected in the presence of a solvent, the nature of which is not critical, provided that it has no adverse effect upon the reaction. Examples of suitable solvents include: alcohols, such as methanol, ethanol, propanol, butanol or ethylene glycol monomethyl ether; ethers, such as tetrahydrofuran or dioxane; amides, such as dimethylformamide or dimethylacetamide; sulfoxides, such as dimethyl sulfoxide; sulfones, such as sulfolane; organic bases, such as triethylamine or pyridine; water; and mixtures of any two or more thereof.

There is no particular limitation on the molar ratio of the hydroxylamine derivative to the compound of formula (VI) and the reaction will take place at any molar ratio. However, we generally prefer to employ an excess of the hydroxylamine derivative, preferably a large excess, with respect to the compound of formula (VI).

A preferred molar ratio of the hydroxylamine derivative to the compound of formula (VI) is from 1:1 to 50:1.

If an acid addition salt of the hydroxylamine derivative is employed, then we prefer to carry out the reaction in the presence of an acid-binding agent. The amount of acid-binding agent is not critical and an amount less than equimolar with respect to the salt of the hydroxylamine derivative can be employed.

The reaction will take place over a wide range of temperatures and the particular temperature chosen is not critical. We prefer to carry out the reaction at a temperature within the range from 0° C. to 100° C. The time required for the reaction will vary widely, depending upon many factors, notably the nature of the reagents and the reaction temperature, but, at temperatures within the preferred range given above, a period of from 5 minutes to 10 days will normally suffice.

Compounds of formula (I) in which W represents a group of formula $>C=N-O-V^2$ (in which $V^2$ represents any one of the acyl groups defined for V) may also be prepared by reacting the corresponding compound of formula (VII) with an acylating agent, preferably an acid halide or acid anhydride, especially an acid anhydride.

In this reaction, if $R^{2a}$, $R^{3a}$, $R^{4a}$ or $R^{5a}$ in the starting material of formula (VI) is or contains an acyl group, an oxime can be prepared.

Step A4

In this step, which is optional, the compound of formula (VI) in which $W^1$ represents a carbonyl group, prepared as described in Step A2, is reduced, to give a compound of formula (VIII).

The reduction is preferably effected by reaction with a reducing agent, such as sodium borohydride or K-selectride, preferably sodium borohydride.

Reaction of the compound of formula (VI) with the reducing agent is effected in the presence of a solvent. The nature of the solvent is not critical, provided that it has no adverse effect upon the reaction. Suitable solvents include, for example: alcohols, such as methanol, ethanol, propanol, butanol or ethylene glycol monomethyl ether; and ethers, such as tetrahydrofuran or dioxane. There is also no criticality as to the ratio of the compound of formula (VI) to the reducing agent, although an excess of the reducing agent is generally preferred. In general, we prefer to employ a molar ratio of reducing agent to compound of formula (VI) of from 1:1 to 20:1.

The reaction will take place over a wide range of temperatures and the particular reaction temperature chosen is not particularly critical. We generally prefer to carry out the reaction at a temperature of from 0° C. to 100° C. The time required for the reaction will vary widely, depending upon many factors, notably the reaction temperature and the nature of the reducing agent, but a period of from 1 to 20 hours will normally suffice.

Step A5

In this step, which is optional, the compound of formula (VIII), prepared as described in Step A4, is dehydrated, to give the compound of formula (IX).

Elimination of water from the compound of formula (VIII) may be effected by contacting the compound with an acid catalyst in a solvent; alternatively, if an acidic solvent is employed, then no additional acid catalyst is required.

Suitable acid catalysts include: inorganic acids, such as hydrochloric acid or sulfuric acid; organic carboxylic acids, such as acetic acid; and organic sulfonic acids, such as p-toluenesulfonic acid. The nature of the solvent employed is not critical, provided that it has no adverse effect upon the reaction. Suitable solvents include, for example: ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; ketones, such as acetone or methyl ethyl ketone; water; and mixtures of any two or more thereof.

There is no particular restriction on the ratio of the compound of formula (VIII) to the acidic catalyst. However, we generally prefer to employ a molar ratio of said compound to said catalyst of from 1:0.001 to 1:1, more preferably from 1:0.01 to 1:01.

Where an acidic solvent is to be employed, we prefer to use an organic acid, particularly an organic carboxylic acid, such as acetic acid.

The reaction will take place over a wide range of temperatures, although we generally prefer to employ a temperature of from 0° C. to 100° C. The time required for the reaction may vary widely, depending upon many factors, notably the nature of the reagents and the reaction temperature, but a period of from 5 minutes to 20 hours will normally suffice.

Step A6

This step is not shown on the reaction scheme and consists of the conversion of one or more of the hydroxy groups represented by or included in the groups represented by $R^{1a}$, $R^{2a}$, $R^{3a}$, $R^{4a}$, $R^{5a}$ or Ar' to a sulfoxy group, an alkoxycarbonyloxy group or an aryloxycarbonyloxy group, or to other groups included in the definitions of $R^2$, $R^3$, $R^4$, $R^5$ and Ar.

Any derivative in which $R^1$, $R^2$, $R^3$, $R^4$, $R^5$, W and/or Ar has a sulfoxy group can be prepared by treating a compound having the corresponding hydroxy group such as a phenolic hydroxy group or an oxime hydroxy group in any of the compounds of formulae (VI), (VII), (VIII) or (IX) with sulfuric acid or with chlorosulfonic acid.

Also any derivative in which $R^1$, $R^2$, $R^3$, $R^4$, $R^5$, W and/or Ar has an acyloxy group, such as an acetoxy, benzoyloxy, alkoxycarbonyloxy or phenoxycarbonyloxy groups, can be prepared by treating, if desired, a corresponding compound having a hydroxy group, i.e. any of the compounds of formulae (VI), (VII), (VIII) or (IX), with an acylating agent.

Such an acylation reaction may be effected by reaction with an acylating agent, normally an organic acid or reactive derivative thereof. Suitable reactive derivatives include the acid halides and acid anhydrides, especially the acid anhydrides. Where an acid itself is employed, we prefer to carry out the reaction in the presence, as catalyst, of a strong acid, for example a mineral acid (such as hydrochloric acid or sulfuric acid) or an organic sulfonic acid (such as p-toluenesulfonic acid).

Otherwise, the nature of the acylating agent employed depends upon the nature of the acyl group which it is desired to introduce, and these are defined above.

The reaction is preferably effected in the presence of an solvent, the nature of which is not critical, provided that it has no adverse effect upon the reaction. Suitable solvents include, for example: ethers, such as diethyl ether, tetrahydrofuran or dioxane; aromatic hydrocarbons, such as benzene or toluene; aliphatic hydrocarbons, such as hexane, cyclohexane or heptane; halogenated hydrocarbons, especially halogenated aliphatic hydrocarbons, such as methylene chloride or chloroform; ketones, such as acetone or methyl ethyl ketone; amides, such as dimethylformamide or dimethylacetamide; organic bases, such as pyridine or triethylamine; sulfoxides, such as dimethyl sulfoxide; sulfones, such as sulfolane; water; and mixtures of any two or more thereof. There is no particular restriction on the ratio of the compound of formula (VI), (VII), (VIII) or (IX) to the acylating agent, but we generally prefer to employ an excess, suitably a slight excess, of the acylating agent or an equimolar amount of the two reagents. In general, we would employ a molar ratio of acylating agent to compound of formula (VI), (VII), (VIII) or (IX) of from 1:1 to 10:1.

The reaction temperature is not critical and the reaction will take place over a wide range of temperatures; however, we generally prefer to carry out the reaction at a temperature of from 0° C. to 100° C. The time required for the reaction will vary widely, depending upon many factors, notably the nature of the reagents and the reaction temperature, but, at a temperature within the recommended range, a period of from 5 minutes to 20 hours will normally suffice.

Alternatively, if desired, the compound of formula (VI), (VII), (VIII) or (IX) may be reacted with an alkylating agent.

The alkylation reaction is normally effected by contacting a halo compound (in which the halogen atom is preferably a chlorine atom) corresponding to the group which it is desired to introduce, such as methoxymethyl chloride, ethoxycarbonylmethyl bromide, 1-(t-butoxycarbonyl)-1-methylethyl bromide or benzyl chloride with the compound of formula (VI), (VII), (VIII) or (IX) in the presence of a base, such as an alkali metal or alkaline earth metal hydride (e.g. sodium hydride or calcium hydride) or an alkali metal alkoxide (e.g. sodium methoxide, sodium ethoxide or potassium t-butoxide). The reaction is normally carried out in the presence of a solvent, for example: an ether, such as diethyl ether, tetrahydrofuran or dioxane; an aromatic hydrocarbon, such as benzene, toluene or xylene; an aliphatic hydrocarbon, such as hexane or heptane; an amide, such as dimethylformamide or dimethylacetamide; a sulfoxide, such as dimethyl sulfoxide; or a sulfone, such as sulfolane. There is no particular limitation on the molar ratio of compound (VI), (VII), (VIII) or (IX) to the halo compound. In general, we prefer to employ from about 0.8 to 1.2 mole of the halo compound per mole of the compound of formula (VI), (VII), (VIII) or (IX). The reaction conditions, particularly the reaction temperature and time, may vary depending upon a number of factors, especially the natures of the starting material, the halo compound and the solvent, but we normally prefer a reaction temperature of from 0° C. to 50° C. and a time of from several minutes to several tens of minutes.

Other optional steps may also be carried out to convert the compounds of formulae (VI), (VII), (VIII) or (IX) to other derivatives within the definitions given. For example, if it is desired to produce a compound of formula (I) in which one of the groups represented by $R^1$, $R^2$, $R^3$, $R^4$, $R^5$ or Ar is or includes a nitro group, this may be achieved by nitrating the corresponding compound of formula (VI), (VII), (VIII) or (IX). The nitration is preferably effected in the presence of a solvent, the nature of which is not critical, provided that it has no adverse effect on the reaction. Examples of suitable solvents include aromatic nitro compounds, such as nirobenzene or 4-nitrotoluene. The nitrating agent is preferably concentrated nitric acid, preferably in the presence of another strong acid, such as concentrated sulfuric acid.

The reaction temperature is not critical to the invention, although the optimum temperature will vary, depending upon the nature of the reagents and the solvent employed. In general, we prefer to carry out the reaction at a temperature of from −10° C. to 50° C. and more preferably from 0° C. to 10° C. The time required for the reaction may also vary, depending upon many factors, notably the reaction temperature and the nature of the reagents, but a period of from several seconds to several hours, e.g. from 1 minute to 10 minutes, will normally suffice.

The nitro compounds thus obtained may be converted directly or indirectly to other derivatives containing other functional groups, by methods well known to those skilled in the art. For example, the corresponding amino compounds may be prepared by catalytic reduction. The reaction conditions employed for this reduction may be the same as those described hereafter in relation to the reduction in Reaction Scheme B. These amino compounds may also, if desired, be converted to other compounds included within the general formula (I) by other conventional reactions, for example alkylation, acylation and the like.

The thiazolidine derivatives of formula (I) obtained by any of the reactions described above can be separated and purified by conventional means for separation and purification, either after each step in their preparation or after the last such step. For example suitable separation and purification techniques include condensation, condensation under reduced pressure, extraction with a solvent, crystallization and recrystallization, dissolving into another solvent, the various chromatography techniques, notably column chromatography or optical resolution.

The compounds used as starting materials for the preparation of the thiazolidine derivatives of formula (I) of this invention, that is the α-halocarboxylic acid derivatives of formula (IV) and their synthetic intermediates, can be prepared by various processes known per se and described, for example in U.S. Pat. No. 4 572 912 and in U.S. patent application Ser. No. 833 867 filed the 25th day of February 1986.

Reaction Scheme B

Compounds of formula (IV) in which $W^1$ and $U^1$ both represent methylene groups can advantageously be prepared as illustrated by Reaction Scheme B:

Reaction Scheme B

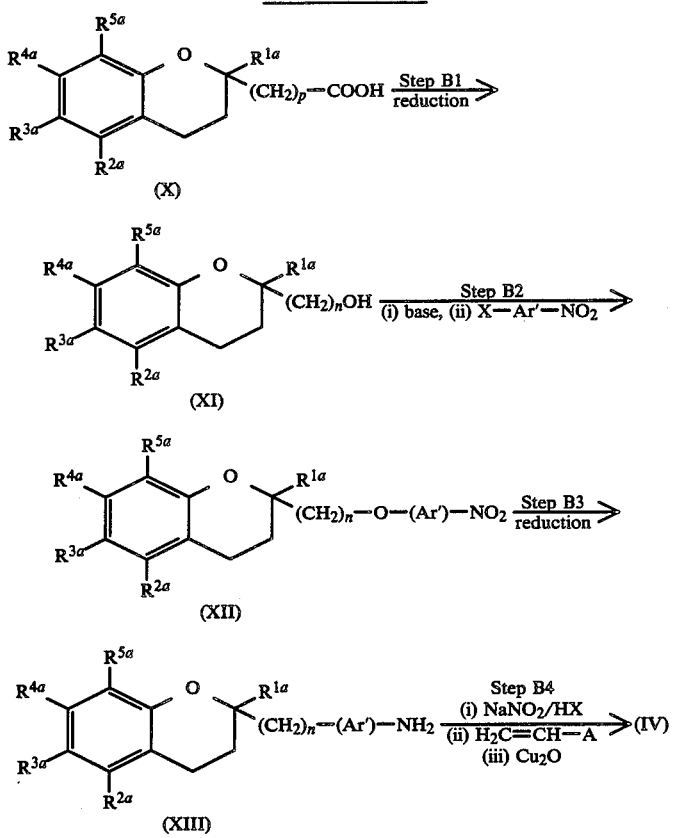

In the above formulae, $R^{1a}$, $R^{2a}$, $R^{3a}$, $R^{4a}$, $R^{5a}$, A, n and Ar' are as defined above; X represents a halogen atom and p=(n-1).

The steps of this reaction scheme correspond exactly with equivalent steps of Method A in U.S. Pat. No. 4 572 912, the disclosure of which is incorporated herein by reference.

In step B2, it is preferred that any free hydroxy group in any of the groups represented by $R^{1a}$, $R^{2a}$, $R^{3a}$, $R^{4a}$, $R^{5a}$ and Ar' should first be protected. The protecting reaction may take place at any convenient point in the reaction sequence prior to Step B2. Examples of suitable protecting groups include optionally substituted alkyl groups, such as the methoxymethyl and 2-tetrahydropyranyl groups. If the group $R^{1a}$, $R^{2a}$, $R^{3a}$, $R^{4a}$, $R^{5a}$ or Ar' represents or includes an acyloxy group, this group may be hydrolyzed, if desired, to the corresponding hydroxy group or hydroxy-containing group, after which it may be protected by any one of the optionally substituted alkyl groups exemplified above.

In Step B3, for the synthesis of the compound of formula (XIII), it is preferred to protect any amino group, when the compound of formula (XI) or (XII) is substituted by an amino or amino-containing group. Examples of suitable protecting groups include alkoxycarbonyl groups, such as the methoxycarbonyl and ethoxycarbonyl groups.

In addition, when synthesizing the compound of formula (XIII), if the compound of formula (XII) is substituted by a hydroxy group protected by any one of the alkyl groups mentioned above or is substituted by a hydroxy-containing group protected by any one of the alkyl groups mentioned above, the protected group may, if desired, be removed, and then the resulting hydroxy group may be protected again with another group, for example, an acyl group, such as an acetyl or benzoyl group.

In Step B3, the compound of formula (XII) is subjected to reduction to give the compound of formula (XIII). A similar reaction may be carried out to convert nitro substituents on the compounds of the present invention to amino groups, as mentioned above.

The reduction may be a catalytic reduction process employing hydrogen or reduction with a metal, such as zinc or iron, and an acid (which may be a mineral acid, such as hydrochloric acid or sulfuric acid, or an organic acid, such as acetic acid), especially a combination of zinc with acetic acid. Preferably a catalytic reduction process is employed. The catalyst employed for this catalytic reduction is preferably palladium-on-carbon, Raney nickel of platinum oxide, of which palladium-on-carbon is particularly preferred. The hydrogen pressure is preferably from 1 to 100 atmospheres (1.01 to 101 bars), more preferably from 1 to 6 atmospheres (1.01 to 6.06 bars). The reaction is preferably effected in the presence of a solvent, the nature of which is not critical, provided that it has no adverse effect on the reaction. Examples of suitable solvents include: alcohols, such as methanol or ethanol; aromatic hydrocarbons, such as benzene or toluene; organic acids, such as acetic acid; amides, such as dimethylformamide; water; or a mixture of any two or more thereof.

The reaction conditions, particularly the reaction temperature and time, may vary depending upon a number of factors, particularly the nature of the starting material, the method employed for reduction and the solvent, but the reaction is normally effected at a temperature from ambient temperature to 50° C. and the period required for the reaction is generally from several minutes to about 20 hours.

In Step B4, the chroman derivative of formula (XIII), prepared as described in step B3 above, is diazotized and then subjected to a Meerwein arylation, to give the desired α-halocarboxylic acid compound of formula (IV). The two reactions are preferably effected sequentially in the same reaction system.

The diazotization reaction comprises reacting the amino compound of formula (XIII) with a nitrite (such as sodium nitrite) in the presence of an acid, such as hydrochloric acid or hydrobromic acid.

The Meerwein arylation reaction comprises reacting the resulting diazonium compound with an acrylic compound of formula $CH_2=CHA$ (in which A is as defined above), e.g. acrylic acid, an acrylic or methacrylic acid ester (such as methyl acrylate, ethyl acrylate or ethyl methacrylate) or another acrylic acid derivative (such as acrylonitrile, acrylamide, methacrylonitrile or methacrylamide), in the presence of a catalytic amount of a cuprous compound (which may be a salt, such as cuprous chloride, or another cuprous compound such as cuprous oxide). The acrylic and methacrylic acid esters are preferred and the preferred cuprous compound is cuprous oxide.

The reactions are preferably effected in the presence of a solvent, the nature of which is not critical, provided that it does not interfere with the reactions. Suitable solvents include: alcohols, such as methanol or ethanol; ketones, such as acetone or methyl ethyl ketone; water; or a mixture of any two or more thereof. The molar ratio of the amino compound of formula (XIII) to the acrylic acid or derivative thereof of formula $CH_2=CHA$ is preferably from 1:1 to 1:15, more preferably from 1:5 or 1:10. The molar ratio of the amino compound (XIII) to the cuprous compound is preferably from 1:0.01 to 1:1, more preferably from 1:0.03 to 1:0.3. The reaction conditions, particularly the reaction temperature and time, may vary depending upon a number of factors, especially the natures of the starting materials and the solvent employed, but the reaction is normally carried out at a temperature from ambient temperature to 100° C., preferably from 30° to 60° C., and the period required for the reaction is normally from about 20 minutes to about 20 hours, more preferably from 30 minutes to 2 hours.

Reaction C

Compounds of formula (IV) in which $W^1$ and $U^1$ both represent methylene groups and n is 2 can advantageously be prepared as illustrated by Reaction C, starting from a phenol of formula (XIV):

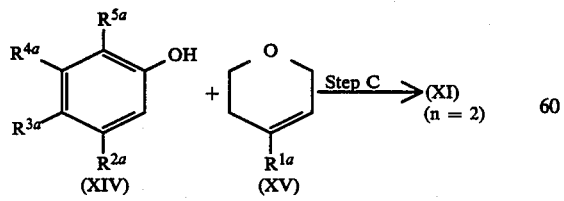

In the above formulae, $R^{1a}$, $R^{2a}$, $R^{3a}$, $R^{4a}$ and $R^{5a}$ are as defined above.

The product is a compound of formula (XI) in which n is 2, which may then be treated as in Reaction Scheme B, Steps B2 to B4, to give the compound of formula (IV). This reaction may be carried out by the method described in Japanese Patent Application Kokai No. 201775/83.

Reaction Scheme D

Compounds of formula (IV) in which $W^1$ and $U^1$ both represent methylene groups, n is 1 and $R^{1a}$ is any group other than a hydrogen atom may advantageously be prepared as illustrated in Reaction Scheme D:

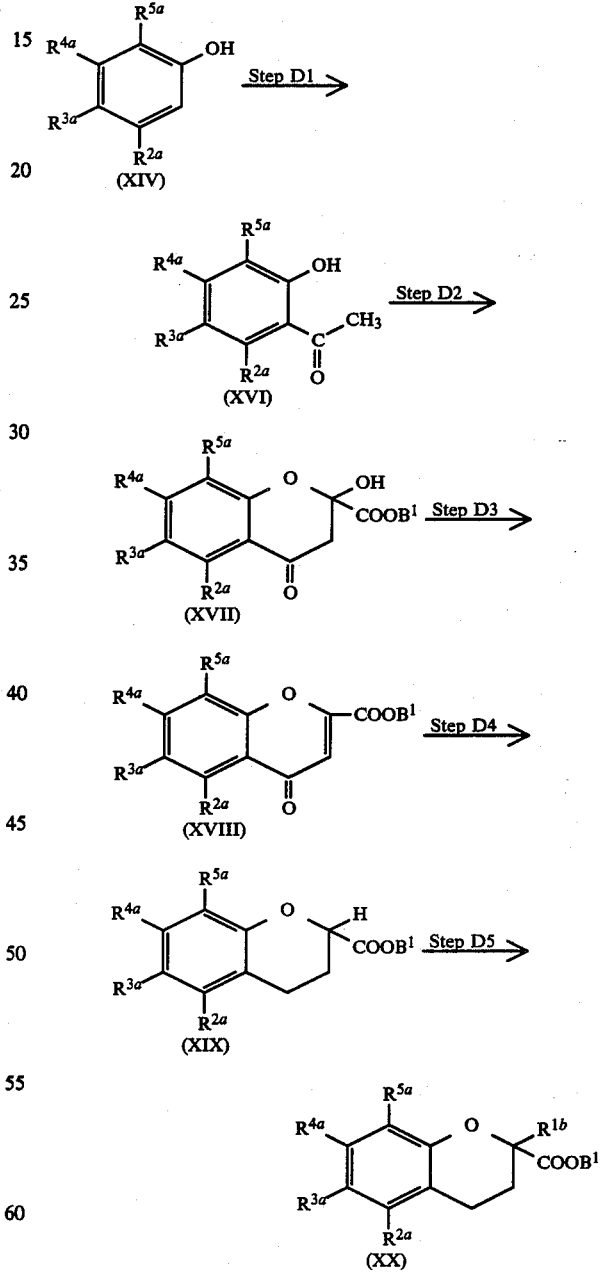

In the above formulae, $R^{2a}$, $R^{3a}$, $R^{4a}$ and $R^{5a}$ are as defined above; $R^{1b}$ represents any one of the groups heretofore defined for $R^{1a}$, other than the hydrogen atom; and $B^1$ represents a hydrogen atom or a carboxy-protecting group, preferably an alkyl, alkenyl, alkynyl, aralkyl or optionally substituted phenyl group, more preferably a $C_1$-$C_4$ alkyl group.

Steps D1–D4

These steps are carried out essentially as described in the Journal of Medicinal Chemistry, 18, 934 (1975).

Step D5

In this step, a chromancarboxylic acid derivative of formula (XX) having a group $R^{1b}$ at the 2-position is prepared. This may be achieved by reacting the compound of formula (XIX) with a base in an inert solvent in order to generate a carbinion and then reacting this carbanion with a compound of formula $R^{1b}X^1$ (in which $R^{1b}$ is as defined above and $X^1$ represents a halogen atom, for example a chlorine, bromine or iodine atom, or a sulfonyloxy group, for example a methanesulfonyloxy, ethanesulfonyloxy, benzenesulfonyloxy or p-toluenesulfonyloxy group).

Any base may be employed in the reaction to generate the carbanion, and examples of such bases include: organic lithium compounds, such as methyllithium, butyllithium, t-butyllithium or phenyllithium, lithium dialkylamides, such as lithium diisopropylamide, lithium dicyclohexylamide or lithium N-isopropyl-N-cyclohexylamide; and alkali metal hydrides, such as lithium hydride, sodium hydride or potassium hydride. Of these, we prefer the organic lithium compounds and lithium dialkylamides.

The reaction is preferably effected in the presence of a solvent, the nature of which is not critical, provided that it has no adverse effect upon the reaction. Suitable solvents include, for example, ethers, such as diethyl ether, tetrahydrofuran or dioxane.

The reaction temperature employed for generation of the carbanion is preferably relatively low, e.g. from $-78°$ C. to room temperature. The temperature employed for reaction of this anion with the compound of formula $R^{1b}X^1$ is preferably somewhat higher, e.g. from $0°$ C. to $60°$ C. The time required for these reactions will vary widely, depending upon many factors, notably the nature of the reagents and the reaction temperature, but a period of from 30 minutes and 2 hours will normally suffice for generation of the carbanion whilst a period of from 1 to 24 hours will normally suffice for the subsequent reaction with the compound $R^{1b}X^1$.

Thereafter, the resulting compound of formula (XX) may be subjected to the same reactions as described in Reaction Scheme B, to give the resulting compound of formula (IV).

Reaction E

This may be used to prepare a compound in which $W^1$ represents a carbonyl group and $U^1$ represents a methylene group, by reacting a compound of formula (XVI) with a compound of formula (XXI) to give a compound of formula (XXII):

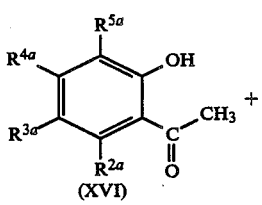

(XVI)

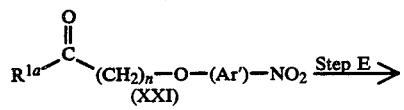

(XXI)

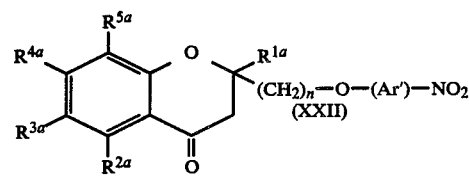

(XXII)

In the above formulae, $R^{1a}$, $R^{2a}$, $R^{3a}$, $R^{4a}$, $R^{5a}$, n an Ar' are as defined above.

This reaction may be carried out following the procedure described as Step B1 of Method B of U.S. Pat. No. 4 572 912. Thereafter, the resulting compound of formula (XXII) may be subjected to the reactions equivalent to those of Steps B3 and B4, to give a compound of formula (IV) in which $W^1$ represents a carbonyl group and $U^1$ represents a methylene group.

Reaction Scheme F

This may be used to prepare a compound in which $W^1$ represents a carbonyl group, $U^1$ represents a methylene group, n is 1 and there is a group $R^{1b}$ at the 2-position of the chroman ring, as shown in the following reaction scheme:

Reaction Scheme F

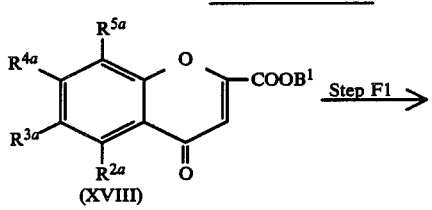

(XVIII)

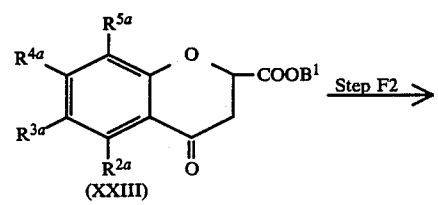

(XXIII)

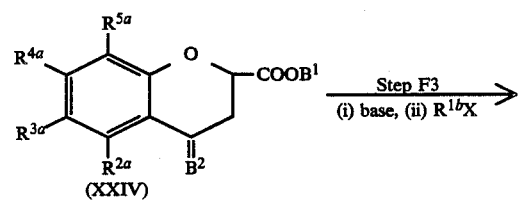

(XXIV)

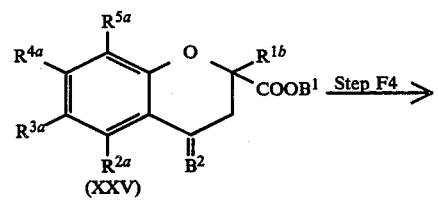

(XXV)

-continued
Reaction Scheme F

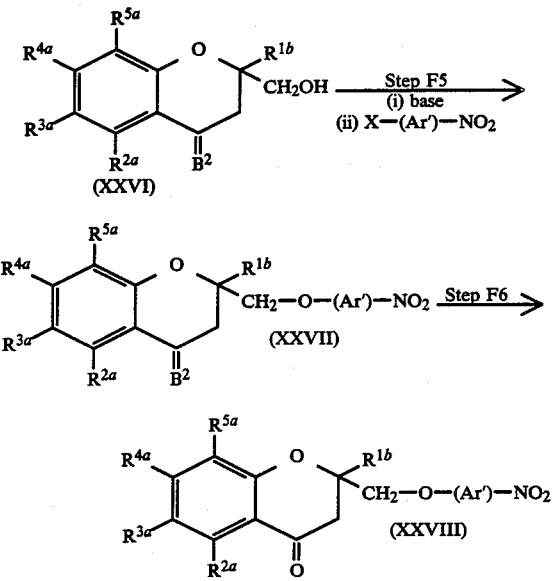

In the above formulae, $R^{1b}$, $R^{2a}$, $R^{3a}$, $R^{4a}$, $R^{5a}$, n, Ar', X and $B^1$ are as defined above; and $B^2$ represents a carbonyl-protecting group, examples of which are described in more detail below.

Step F1

In this step, the starting material of formula (XVIII), which may have been prepared as described in step D3 of Reaction Scheme D, is subjected to reduction, but under milder conditions than employed in step D4, so that only the double bond between the 2- and 3-positions is hydrogenated.

The reaction is preferably effected by catalytic hydrogenation. Suitable catalysts include palladium-on-carbon, Raney nickel and platinum oxide, of which palladium-on-carbon is preferred. The reaction is preferably effected employing a partial pressure of hydrogen of from 1 to 100 atmospheres (about 1 to 101 bars), more preferably from 1 to 6 atmospheres (about 1 to 6 bars). The reaction is preferably effected in the presence of a solvent, the nature of which is not critical, provided that it has no adverse effect upon the reaction. Suitable solvents include, for example: alcohols, such as methanol or ethanol; aromatic hydrocarbons, such as benzene or toluene; ethers, such as tetrahydrofuran; amides, such as dimethylformamide or dimethylacetamide; organic carboxylic acids, such as acetic acid; water; and mixtures of any two or more thereof.

The reaction will take place over a wide range of temperatures, but we prefer to employ a temperature of from room temperature to 50° C., more preferably from room temperature to 40° C. The time required for the reaction will vary widely, depending upon many factors, notably the nature of the reagents and the reaction temperature; however, at a temperature within the preferred range described above, the reaction will normally be complete within a period of from several minutes to several days, commonly from 30 minutes to 20 hours.

Step F2

In this step, the carbonyl group at the 4-position of the chroman compound of formula (XXIII) prepared in step F1 is protected; it is desirable that this protection should be carried out prior to the alkylation reaction of step F3.

There is no particular limitation on the nature of the protecting group employed and any such group commonly used for protecting carbonyl groups may equally well be used in the present invention. For example, the oxo compound may be converted into a protected enol compound, such as an enol ether or enol ester. Alternatively, it may be converted into a ketone acetal having cyclic or non-cyclic side chains or into a ketone dithioacetal. Conversion into a ketone dithioacetal is preferred.

Preferably, $B^2$ represents a group of formula —$B^3$—$B^4$—$B^3$—, where $B^3$ represents an oxygen or sulfur atom (preferably a sulfur atom) and $B^4$ represents a group of fomula —$(CH_2)_2$—, —$(CH_2)_3$—, —$(CH_2)_4$— or ($CH_2$—CH=CH—$CH_2$(cis), preferably —$(CH_2)_2$— or —$(CH_2)_3$— and more preferably —$(CH_2)_3$—. Such a protectd compound may be prepared by reacting the compound of formula (XXIII) with a compound of formula H—$B^3$—$B^4$—$B^3$—H (in which $B^3$ and $B^4$ are as defined above), for example ethylene glycol, 1,3-propanediol, 1,2-ethanedithiol, 1,3-propanedithiol or cis-2-butene-1,4-diol, preferably 1,3-propanedithiol, under dehydrating conditions. The reaction may take place in the presence or absence of a catalyst. Where a catalyst is employed, suitable catalysts include, for example: Lewis acids, such as boron trifluoride (or diethyl ether or acetic acid complexes thereof) or aluminum chloride; inorganic acids, such as hydrogen chloride or sulfuric acid; organic carboxylic acids, such as acetic acid, tartaric acid, fumaric acid or maleic acid; and organic sulfonic acids, such a p-toluenesulfonic acid or methanesulfonic acid. We prefer to use a Lewis acid, more preferably a boron trifluoride acetic acid complex salt.

The reaction does not always require a solvent; however, if a solvent is employed, its nature is not critical, provided that it has no adverse effect upon the reaction. Examples of suitable solvents include: aromatic hydrocarbons, such as benzene or xylene; and halogenated hydrocarbons, especially halogenated aliphatic hydrocarbons, such as chloroform or methylene chloride. Of these, we prefer halogenated hydrocarbons, such as chloroform.

There is no particular limitation on the proportions of the compound of formula (XXIII) to the compound of formula H—$B^3$—$B^4$—$B^3$—H; however, a small excess of the compound H—$B^3$—$B^4$—$B^3$—H is preferred, preferably a molar ratio of the compound H—$B^3$—$B^4$—$B^3$—H to the compound of formula (XXIII) of from 1:1 to 2:1. Equally, there is no particular limitation on the proportions of catalyst employed. However, a molar ratio of catalyst to compound of formula (XXIII) of from 1:1 to 1:4 is preferred.

The reaction will take place over a wide range of temperatures, but we generally prefer to carry out the reaction at a temperature of from 0° to 100° C., more preferably from 10° C. to 40° C. The time required for the reaction may vary widely, depending upon the nature of the reagents and the reaction temperature, but a period of from several minutes to several days, more commonly from 1 hour to 30 hours, will normally suffice.

Step F3

In this step, the compound of formula (XXIV) is converted to a carbanion and then reacted with a compound of formula $R^{1b}X^1$ (in which $R^{1b}$ and $X^1$ are as defined above). This reaction is similar to that described above in relation to step D5 and may be carried out employing the same reagents and under the same reaction conditions as employed in step D5.

If it is desired to prepare a compound in which $R^1$ represents a hydrogen atom, step F3 may be omitted, and the product of step F2 [the compound of formula (XXIV)] may be employed directly in step F4.

Step F4

In this step, the chroman-2-carboxylic acid derivative of formula (XXV) is reduced to the corresponding alcohol of formula (XXVI). This reaction is essentially the same as that described above in step B1 of the Reaction Scheme B and may be carried out under the same conditions and employing the same reagents. However, in this case, we prefer to employ a temperature within the range from $-50°$ C. to $+120°$ C.

Step F5

In this step, a group of formula $—(Ar')—NO_2$ ($Ar'$ being as defined above) is introduced into the compound of formula (XXVI) prepared as described in step F4. This reaction may be effected by reacting the compound of formula (XXVI) with a base to convert it to the corresponding alkoxide, and then reacting this with a compound of formula $X—(Ar')—NO_2$ (in which $X$ and $Ar'$ are as defined above).

Any base capable of forming an alkoxide with the compound of formula (XXVI) may be employed. Examples include: alkali metal and alkaline earth metal hydrides, such as sodium hydride or calcium hydride; and alkali metal alkoxides, such as sodium methoxide, sodium ethoxide or potassium t-butoxide. Of these, we prefer sodium hydride or sodium ethoxide. The proportions of the compound of formula (XXVI) and the base are not particularly critical; however, we prefer to employ a slight excess of the base, preferably a molar ratio of base to compound of formula (XXVI) of from 1:1 to 2:1.

The reactions are preferably effected in the presence of a solvent, the nature of which is not critical, provided that it has no adverse effect upon the reaction. Suitable solvents include, for example: ethers, such as diethyl ether, tetrahydrofuran or dioxane; aromatic hydrocarbons, such as benzene, toulene or xylene; aliphatic hydrocarbons, such as hexane or heptane; amides, such as dimethylformamide or dimethylacetamide; sulfoxides, such as dimethyl sulfoxide; and sulfones, such as sulfolane. Of these, the amides are preferred.

The relative proportions of the compoound of formula $X—(Ar')—NO_2$ to the compound of formula (XXVI) are not particularly critical to the present invention, however, we prefer to employ a slight excess of the compound of formula $X—(Ar')—NO_2$, preferably a molar ratio of said compound of formula $X—(Ar')—NO_2$ to compound of formula (XXVI) of from 1:1 to 10:1.

The reaction will take place over a wide range of temperatures, but we generally prefer to employ a temperature of from 30° C. to 100° C. The time required for the reaction may vary widely, depending upon many factors, notably the nature of the reagents and the reaction temperature. A period of from several minutes to several hours will normally suffice.

Step F6

The nitro compound of formula (XXVII) thus obtained may then be converted to the desired compound of formula (XXVIII) by deprotecting the protected carbonyl group at the 4-position of the chroman system.

Any conventional reaction employed to deprotect a protected carbonyl group may be employed in this step. For example, the protected compound may be reacted with: a protonic acid, such as hydrochloric acid or sulfuric acid; a Lewis acid, such as boron trifluoride (or an ether, e.g. diethyl ether, or acetic acid complex thereof) or aluminum chloride; when $B^3$ represents a sulfur atom, a heavy metal salt, heavy metal oxide, heavy metal peroxide or a mixture of any two or three of these, for example a silver, cadmium, mercurous, mercuric, cuprous or thallic chloride, bromide, iodide, nitrate, perchlorate, oxide or peroxide; iodine; a sulfuryl halide, such as sulfuryl chloride; or an N-haloimide, such as N-chlorosuccinimide or N-bromosuccinimide. Of these, we prefer mercuric chloride, mercuric oxide or a mixture thereof, more preferably a mixture of mercuric chloride and mercuric oxide.

The reaction is preferably effected in the presence of a solvent, the nature of which is not critical, provided that it has no adverse effect upon the reaction. Suitable solvents include, for example: alcohols, such as methanol, ethanol, propanol or isopropanol; ketones, such as acetone or methyl ethyl ketone; halogenated hydrocarbons, especially halogenated aliphatic hydrocarbons, such as chloroform, methylene chloride or 1,2-dichloroethane; ethers, such as tetrahydrofuran or dioxane; organic carboxylic acids, such as acetic acid; nitriles, such as acetonitrile; water; and mixtures of any two or more thereof.

The proportions of the compound of formula (XXVII) or other protected compound to the deprotecting agent are not critical. However, we prefer to employ a slight excess of the deprotecting agent, e.g. a molar ratio of deprotecting agent to compound of formula (XXVII) or other protected compound of from 1:1 to 10:1, more preferably from 1:1 to 4:1.

The reaction will take place over a wide range of temperatures, but we generally find it convenient to carry out the reaction at a temperature within the range from room temperature to 100° C., more preferably from 40° C. to 80° C. The time required for the reaction will vary, depending upon many factors, notably the nature of the reagents and the reaction temperature; however, at a temperature within the ranges mentioned above, a period of from several minutes to several hours, more commonly from 30 minutes to 4 hours, will normally suffice.

Reaction Scheme G

A particularly preferred process for preparing compounds of formula (IV) in which both $W^1$ and $U^1$ represent methylene groups includes the steps illustrated in the following reaction scheme:

Reaction Scheme G

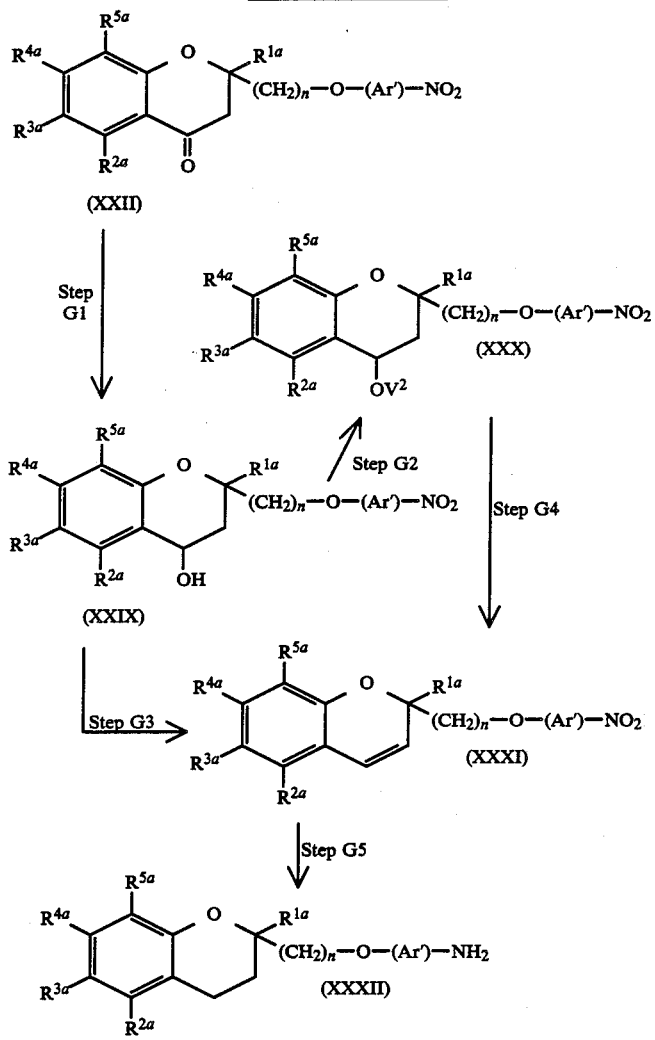

In the above formulae, $R^{1a}$, $R^{2a}$, $R^{3a}$, $R^{4a}$, $R^{5a}$, $V^2$, n and Ar' are as defined above.

Step G1

In this step, a 4-oxochroman derivative of formula (XXII), which may have been prepared by a variety of the methods described above, e.g. Reaction E, is reduced to the corresponding 4-hydroxy compound of formula (XXIX). Any reducing agent capable of reducing an oxo group on a saturated ring system to a hydroxy group may be employed. We generally prefer to employ sodium borohydride or K-selectride, of which sodium borohydride is particularly preferred.

The reaction is preferably effected in the presence of a solvent, the nature of which is not critical, provided that it has no adverse effect upon the reaction. Suitable solvents include, for example: alcohols, such as methanol, ethanol, propanol, butanol or ethylene glycol monomethyl ether; and ethers, such as tetrahydrofuran or dioxane.

There is no particular limitation on the relative proportions of the compound of formula (XXII) to the reducing agent, e.g. sodium borohydride, but we generally prefer to employ an excess, preferably a slight excess, of the reducing agent. In general, we would use a molar ratio of reducing agent to compound of formula (XXII) of from 1:1 to 20:1.

The reaction will take place over a wide range of temperatures and the exact temperature chosen is not particularly critical. A temperature within the range from 0° C. to 100° C. is generally preferred. The time required for the reaction may vary widely, depending upon many factors, notably the nature of the reagents and the reaction temperature. However, a period of from 1 to 20 hours will normally suffice.

Step G2

In this optional step, the compound of formula (XXIX) prepared as described in step G1 is acylated. The acylating agent employed is preferably an acid halide or acid anhydride.

The reaction is preferably carried out in the presence of a solvent, the nature of which is not critical, provided that it does not interfere with the reaction. Suitable solvents include, for example: ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; organic bases, such as pyridine or triethylamine; amides, such as dimethylformamide or dimethylacetamide; sulfoxides, such as dimethyl sulfoxide; and sulfones, such as sulfolane.

There is no particular limitation on the proportions of compound of formula (XXIX) to the acylating agent, but we generally prefer to use equimolar amounts or a slight excess of acylating agent. In general, a molar ratio of acylating agent to compound of formula (XXIX) of from 1:1 to 10:1 is preferred.

The reaction will take place over a wide range of temperatures and the particular temperature chosen is not critical. We generally prefer to carry out the acylation reaction at a temperature within the range from 0° C. to 100° C. The time required for the reaction may vary over a wide range, depending upon many factors, notably the nature of the reagents and the reaction temperature; however, at a temperature within the preferred range, a period of from 5 minutes to 20 hours will normally suffice.

Step G3

In this step, which is an alternative to step G2, a 2H-chromene compound of formula (XXXI) is prepared by dehydrating the 4-hydroxychroman (XXIX).

The dehydration reaction may be achieved in the presence or absence of a dehydrating agent or dehydrating catalyst. Suitable dehydrating agents and catalysts include, for example: inorganic acids, such as hydrochloric acid, sulfuric acid, nitric acid or phosphoric acid; organic carboxylic acids, such as acetic acid, tartaric acid or maleic acid; organic sulfonic acids, such as p-toluenesulfonic acid, naphthalenesulfonic acid or methanesulfonic acid; inorganic salts, such as ammonium chloride or calcium chloride; phosphorus pentoxide; polyphosphoric acid; silica gel; and alumina. Of these, we prefer an organic carboxylic acid such as acetic acid or an organic sulfonic acid, such as p-toluenesulfonic acid.

It is not always necessary to employ a solvent in this reaction; however, where a solvent is used, its nature is not particularly critical, provided that it does not interfere with the reaction. Examples of suitable solvents include: alcohols, such as methanol, ethanol or isopropanol; ketones, such as acetone or methyl ethyl ketone; ethers, such as diethyl ether, tetrahydrofuran or dioxane; aromatic hydrocarbons, such as benzene, toulene or xylene; aliphatic hydrocarbons, such as hexane, cyclohexane or heptane; halogenated hydrocarbons, especially halogenated aliphatic hydrocarbons, such as methylene chloride or chloroform; organic carboxylic acids, such as acetic acid or propionic acid; organic bases, such as pyridine or triethylamine; amides, such as dimethylformamide or dimethylacetamide; sulfoxides, such as dimethyl sulfoxide; sulfones, such as sulfolane; water; and mixtures of any two or more thereof. Of these, we prefer aromatic hydrocarbons, such as benzene, or organic acids, such as acetic acid.

If a dehydrating agent or catalyst is employed, the relative proportion of such agent or catalyst to the compound of formula (XXIX) is not critical, but we prefer to employ a molar ratio of said agent or catalyst to said compound of formula (XXIX) of from 0.01:1 to 10:1, more preferably from 0.1:1 to 3:1.

The reaction will take place over a wide range of temperatures and the exact temperature chosen is not particularly critical; however, we generally prefer to carry out the reaction at a temperature in the range from 0° C. to 100° C. The time required for the reaction will vary, depending upon many factors, notably the nature of the reagents and the reaction temperature; however, at temperatures within the preferred range indicated above, a period of from several minutes to 20 hours will normally suffice.

Step G4

In this step, the 2H-chromene compound of formula (XXXI) is prepared from the 4-acyloxychroman of formula (XXX) by elimination of an acid of formula $V^2OH$ (in which $V^2$ is as defined above).

This elimination reaction can be carried out in the presence or absence of an acid-binding agent or catalyst. Examples of suitable such agents and catalysts include: inorganic acids, such as hydrochloric acid, sulfuric acid, nitric acid or phosphoric acid; organic carboxylic acids, such as acetic acid, tartaric acid or maleic acid; organic sulfonic acids, such as p-toluenesulfonic acid, napthalenesulfonic acid or methanesulfonic acid; inorganic salts, such as ammonium chloride or calcium chloride; organic bases, such as pyridine or triethylamine; silica gel; and alumina. Of these, we prefer an organic carboxylic or sulfonic acid, such as acetic acid or p-toluenesulfonic acid.

It is not always necessary to employ a solvent for this elimination reaction and, where a solvent is employed, its nature is not critical, provided that it has no adverse effect on the reaction. Suitable solvents include, for example: alcohols, such as methanol, ethanol or isopropanol; ketones, such as acetone or methyl ethyl ketone; ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, such as methylene chloride or chloroform; organic acids, such as acetic acid or propionic acid; organic bases, such as pyridine or triethylamine; amides, such as dimethylformamide or dimethylacetamide; sulfoxides, such as dimethyl sulfoxide; sulfones, such as sulfolane; and water. Of these, we prefer aromatic hydrocarbons (such as benzene) or organic acids (such as acetic acid).

Where an acid-binding agent or catalyst is employed, the relative proportions of such agent or catalyst and the compound of formula (XXX) are not particularly critical. We generally prefer to employ the agent or catalyst and the compound of formula (XXX) in a molar ratio of from 0.01:1 to 10:1, more preferably from 0.1:1 to 3:1.

The reaction will take place over a wide range of temperatures and the exact temperature chosen is not particularly critical. In general, we prefer to carry out the reaction at a temperature within the range from 0° C. to 120° C., more preferably from 40° C. to 100° C. The time required for the reaction may vary widely, depending upon many factors, notably the nature of the reagents and the reaction temperature; however, at a temperature within the preferred ranges indicated above, a period of from several minutes to several days, commonly from 10 minutes to 10 hours, will normally suffice.

Step G5

In this step, the chroman derivative of formula (XXXII) is prepared by the reductive hydrogenation of the 2H-chromene derivative of formula (XXXI).

Catalytic hydrogenation is preferably employed. Suitable catalysts include, for example, palladium-oncarbon, Raney nickel or platinum oxide, of which palladium-on-carbon is preferred. The partial pressure of hydrogen may vary widely, for example from 1 to 100 atmospheres (about 1 to 101 bars), more preferably from 1 to 6 atmospheres (about 1 to 6 bars). The reaction is preferably effected in the presence of a solvent, the nature of which is not critical, provided that it does not interfere with the reaction. Suitable solvents include, for example: alcohols, such as methanol or ethanol; aromatic hydrocarbons, such as benzene or toluene; ethers, such as tetrahydrofuran; organic acids, such as acetic acid; water; or a mixture of any two or more thereof.

The reaction will take place over a wide range of temperatures and the exact temperature chosen is not particularly critical; however, we generally prefer to carry out the reaction at a temperature from room temperature to 50° C. The time required for the reaction may vary widely, depending upon many factors, notably the nature of the reagents and the reaction temperature; however, at a temperature within the indicated range, a period of from several minutes to 20 hours will normally suffice.

Reaction H

Other intermediates can be obtained by modification of intermediates obtained as described in the above Reaction Schemes B to G according to suitable known reactions. For example, a compound of formula (XXXIV) wherein any one of $R^{2a}$, $R^{4a}$ and $R^{5a}$ represents a hydroxy group, and any other one of $R^{2a}$, $R^{3a}$, $R^{4a}$ and $R^{5a}$ represents an acyl group such as an acetyl group can be obtained by acylation of a nitro compound having a phenolic hydroxy group, for example the compound of formula (XXXIII), according to conventional means followed by a Fries rearrangement reaction, as illustrated in the following reaction H:

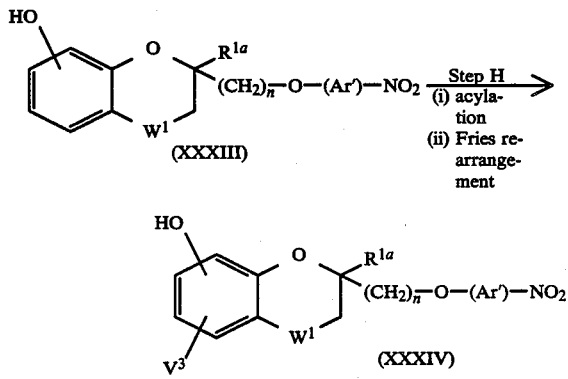

In these formulae, $R^{1a}$, $W^1$, n and Ar' are as defined above; and $V^3$ represents an acyl group, for example an acetyl group.

Also, a compound having an optionally protected phenolic hydroxy group and a substituent $R^{2a}$, $R^{3a}$, $R^{4a}$ or $R^{5a}$ possessing 1 carbon-containing group such as a halomethyl group, a hydroxymethyl group, an alkoxymethyl group, an acyloxymethyl group, a formyl group, a carboxy group or an alkoxycarbonyl group, for example the compound of formula (XVI), may be prepared from the corresponding compound having an optionally protected phenolic hydroxy group and, additionally, a methyl group or a halogen atom at $R^{2a}$, $R^{3a}$, $R^{4a}$ or $R^{5a}$ by conventional means.

The above compounds having a substituent possessing 1 carbon-containing group can be changed to each other by known reactions such as oxidation, reduction, halogenation, esterification and hydrolysis, if desired. Any compound having a phenolic hydroxy group and a substituent possessing 1 carbon-containing group obtained as described above, for example the compound of formula (XVI) [which can be prepared from the compound of formula (XIV) by acylation followed by a Fries rearrangement] in Reaction Scheme D, can be converted by conventional means into a nitro compound, for example the compound of formula (XXII) in Step E, according to, for example, a similar reaction to that described in Reaction Scheme D or Step E. In this reaction, a substituent possessing 1 carbon-containing group may be subjected as desired to protecting or deprotecting reactions, and, if desired, subjected to the conversion reactions as mentioned above.

When preparing the desired compound of formula (I) or its intermediates, the corresponding starting compound may be a crude product, if desired, or it may be a mixture, provided that it does not affect the reaction. Further, the starting compound may be a mixture in a certain ratio of two or more compounds which can afford the same target compound.

In the thiazolidine derivatives of formula (I), when W represents a methylene group, a carbonyl group, a group of formula $>C=N-OV$ (in which V is a defined above) or W forms, together with V, a carbon-carbon double bond, each of the carbon atoms at the 2-position of the chroman ring and at the 5-position of the thiazolidine ring is an asymmetric carbon atom. In the thiazolidine derivatives of formula (I), when W represents a group having the formula $>CH-OY$ (in which Y is as defined above), each of the carbon atoms at the 2-position and 4-position, and the carbon atom at the 5-position of thiazolidine ring is an asymmetric carbon atom. In the thiazolidine derivatives of formula (I), when W represents a carbonyl group or a group having the general formula $>C=N-OV$ (in which V is a defined above), or U, together with $R^1$, forms a double bond, the carbon atom at the 5-position of the thiazolidine ring is an asymmetric carbon atom.

The compounds of the present invention can therefore exist in the form of various isomers. Although all such isomers are represented herein by a single formula only, the present invention envisages both the individual isolated isomers and mixtures thereof. The compounds of the invention may be produced in the form of individual isomers by using an isolated isomer as the starting material or by stereospecific synthesis techniques. Alternatively, the compounds may be produced as a mixture of such isomers, in which case they may be employed in the form of such a mixture or the individual isomers may be separated by conventional resolution techniques.

A compound of formula (I) in which W represents a group of formula $>C=N-OV$ (in which V is as defined above), or an oxime, oxime-ether, or oxime-ester type compound, may be in either the anti-form or the syn-form. The present invention covers both isomers.

The compounds of formula (I) of the present invention can be changed to their pharmaceutically acceptable non-toxic salts by conventional means.

Oxime-type compounds, as mentioned above, can also be changed to salts by conventional means. If the salts are formed with cations, examples include alkali metal ions such as the sodium or potassium ion, alkaline earth metal ions such as the calcium ion and trivalent metal ions such as the aluminum ion.

When the compounds of formula (I) of the present invention possess a basic group, it can be changed to salts as mentioned above. Suitable salts include inorganic salts such as the hydrochloride, sulfate, nitrate or phosphate; and organic salts such as the acetate, succinate, maleate, fumarate, malate, glutamate, aspartate, p-toluesulfonate or methanesulfonate.

Biological Activity

The compounds of the present invention have demonstrated a variety of valuable pharmacological effects, for example as follows. The compounds have shown the ability to lower blood glucose levels in a test using genetically diabetic KK mice, and have shown the ability to inhibit aldose reductase in a test using bovine crystalline lens. The blood glucose lowering effect is of very long duration and is accompanied by a lipid lowering effect. The compounds have a very low toxicity to experimental animals, such as rats. The anoretic effect, inhibitory effect on body weight increase and, in particular, the hypertrophic effect on the liver of the compounds are very weak.

Accordingly, it is considered that the compounds of the present invention will be useful for the therapeutic treatment of human hyperlipemia, diabetes mellitus, and complications thereof, such as diabetic-induced cataracts, neuropathy or nephropathy. The compounds of the invention may be administered orally, for example in the form of tablets, capsules, powders or granules, or parenterally, for example by injection (intravenous, subcutaneous or intramuscular) or in the form of a suppository. Alternatively, they may be formulated for topical administration, e.g. to the eyes. For example, for administration to the eye mucosa, it is preferred that the compounds of the invention should be administered in the form of eye drops or eye ointments, the formulation of which is well known in the art.

The recommended dosage will, of course, vary depending upon the age and body weight of the patient as well as the nature and severity of the disease, and the intended route of administration. However, for an adult human patient, a daily dose of from 5.0 mg to 5 g (which may be administered in a single dose or in divided doses) is recommended in the treatment of hyperlipaemia, diabetes mellitus and complications thereof, when administered orally or parenterally.

The following Examples illustrate the preparation of various of the compounds of the present invention. Preparation of various of the starting materials employed in these Examples is illustrated in the subsequent Preparations. The subsequent Test Example illustrates the valuable biological properties of these compounds.

In the nuclear magnetic resonance spectra reported in the Examples and Preparations, the abbreviation "nd" means that precise identification of the signal was not possible because of overlap by other signals or the absorption of the solvent.

EXAMPLE 1

5-[4-(2-Methylchroman-2-ylmethoxy)benzyl]thiazolidine-2,4-dione

A mixture of 330 mg of ethyl 2-chloro-3-[4-(2-methylchroman-2-ylmethoxy)phenyl]propionate (prepared as described in Preparation 5), 100 mg of thiourea and 1 ml of sulfolane was heated at 130° C. for 5 hours. At the end of this time, 2 ml of ethylene glycol monomethyl ether and 1.5 ml of 2N aqueous hydrochloric acid were added to the reaction mixture, which was then heated under reflux for 4.5 hours. The reaction mixture was then poured into water and extracted with ethyl acetate. The extract was dried over anhydrous magnesium sulfate, and the solvent was distilled off under reduced pressure. The resulting residue was subjected to silica gel column chromatography eluted with a 2:1 by volume mixture of hexane and ethyl acetate. The oily substance thereby obtained was washed with warm water and dried, to give 230 mg of the title compound as a pale yellow glass, softening at 42°-50° C.

Nuclear Magnetic Resonance Spectrum (CDCl$_3$) δ ppm:
1.44 (3H, singlet);
1.7-2.3 (2H, multiplet);
2.77 (2H, triplet, J=7 Hz);
3.06 (1H, doublet of doublets, J=9 and 14 Hz);
3.43 (1H, doublet of doublets, J=4 and 14 Hz);
3.88 and 3.97 (2H, AB-type, J=9 Hz);
4.47 (1H, doublet of doublets, J=4 and 9 Hz);
6.7-7.25 (8H, multiplet);
8.33 (1H, broad singlet, disappeared on adding D$_2$O).
Mass Spectrum (m/e): 383 (M$^+$).

EXAMPLE 2

5-[4-(2-Methyl-4-oxochroman-2-ylmethoxy)benzyl]-thiazolidine-2,4-dione

Following a procedure similar to that described in Example 1, 410 mg of the title compound, softening at 52°-60° C., were obtained from 900 mg of ethyl 2-chloro-3-[4-(2-methyl-4-oxochroman-2-ylmethoxy)-phenyl]propionate (prepared as described in Preparation 7), 270 mg of thiourea, 1 ml of sulfolane, 4 ml of ethylene glycol monomethyl ether and 3 ml of 2N aqueous hydrochloric acid.

Nuclear Magnetic Resonance Spectrum (CDCl$_3$) δ ppm:
1.54 (3H, singlet);
2.73 (1H, doublet, J=16.5 Hz);
3.09 (1H, doublet of doublets, J=9 and 14 Hz);
3.13 (1H, doublet, J=16.5 Hz);
3.43 (1H, doublet of doublets, J=4 and 14 Hz);
3.98 and 4.13 (2H, AB-type, J=10 Hz);
4.48 (1H, doublet of doublets, J=4 and 9 Hz);
6.75-7.2 (6H, multiplet);
7.49 (1H, doublet of triplets, J=2 and 7.5 Hz);
7.9 (1H, doublet of doublets, J=2 and 9 Hz);
8.35-8.8 (1H, broad, disappeared on adding D$_2$O).
Mass Spectrum (m/e): 397 (M$^+$).

EXAMPLE 3

5-[4-(6-Fluoro-2-methylchroman-2-ylmethoxy)benzyl]-thiazolidine-2,4-dione

Following a procedure similar to that described in Example 1, 1.38 g of the title compound were obtained from 1.9 g of ethyl 2-chloro-3-[4-(6-fluoro-2-methylchroman-2-ylmethoxy)phenyl]propionate (prepared as described in Preparation 12), 540 mg of thiourea, 2 ml of sulfolane, 8 ml of ethylene glycol monomethyl ether, 4 ml of concentrated aqueous hydrochloric acid and 5 ml of water. The title compound was a pale yellow powder.

Nuclear Magnetic Resonance Spectrum (CDCl$_3$) δ ppm:
1.44 (3H, singlet);
1.7-2.35 (2H, multiplet);
2.77 (2H, triplet, J=7 Hz);

3.08 (1H, doublet of doublets, J=9 and 14 Hz);
3.46 (1H, doublet of doublets, J=4 and 14 Hz);
3.91 and 3.98 (2H, AB-type, J=10 Hz);
4.49 (1H, doublet of doublets, J=4 and 9 Hz);
6.7–7.0 (5H, nd);
7.17 (2H, doublet, J=9 Hz);
8.45–9.1 (1H, broad, disappeared on adding D$_2$O).
Mass Spectrum (m/e): 401 (M+).

EXAMPLE 4

5-[4-(6-Fluoro-2-methyl-4-oxochroman-2-ylmethoxy)-benzyl]thiazolidine-2,4-dione

Following a procedure similar to that described in Example 1, 430 mg of the title compound were obtained from 600 mg of ethyl 2-chloro-3-[4-(6-fluoro-2-methyl-4-oxochroman-2-ylmethoxy)phenyl]propionate (prepared as described in Preparation 14), 170 mg of thiourea, 1 ml of sulfolane, 3 ml of ethylene glycol monomethyl ether and 2 ml of 2N aqueous hydrochloric acid. The compound was a pale brown powder.

Nuclear Magnetic Resonance Spectrum (CDCl$_3$) δ ppm:
1.52 (3H, singlet);
2.74 (1H, doublet, J=16.5 Hz);
2.97 (1H, doublet of doublets, J=9 and 14 Hz);
3.13 (1H, doublet, J=16.5 Hz);
3.43 (1H, doublet of doublets, J=4 and 14 Hz);
3.98 and 4.12 (2H, AB-type, J=10 Hz);
4.47 (1H, doublet of doublets, J=4 and 9 Hz);
6.83 (2H, doublet, J=9 Hz);
6.93 (1H, doublet of doublets, J=4 and 9 Hz);
7.05–7.4 (1H, nd);
7.16 (2H, doublet, J=9 Hz);
7.55 (1H, doublet of doublets, J=3 and 8 Hz);
8.2–8.7 (1H, broad singlet, disappeared on adding D$_2$O).
Mass Spectrum (m/e): 415 (M+).

EXAMPLE 5

5-[4-(7-Hydroxy-2,8-dimethyl-4-oxochroman-2-ylmethoxy)benzyl]thiazolidine-2,4-dione Following a procedure similar to that described in Example 1, 290 mg of the title compound were obtained from 354 mg of ethyl 2-chloro-3-[4-(7-hydroxy-2,8-dimethyl-4-oxochroman-2-ylmethoxy)phenyl]propionate (prepared as described in Preparation 20), 125 mg of thiourea, 1 ml of sulfolane, 1.5 ml of ethylene glycol monomethyl ether and 1.5 ml of 2N aqueous hydrochloric acid. The compound was a pale brown powder.

Nuclear Magnetic Resonance Spectrum (hexadeuterated acetone) δ ppm:
1.52 (3H, singlet);
2.03 (3H, singlet);
2.63 (1H, doublet, J=16.5 Hz);
3.02 (1H, doublet, J=16.5 Hz);
3.08 (1H, doublet of doublets, J=9 and 14 Hz);
3.43 (1H, doublet of doublets, J=4 and 14 Hz);
4.17 (2H, singlet);
4.74 (1H, doublet of doublets, J=4 and 9 Hz);
6.58 (1H, doublet, J=9 Hz);
6.96 (2H, doublet, J=9 Hz);
7.23 (2H, doublet, J=9 Hz);
7.59 (2H, doublet, J=9 Hz);
9.1–10.2 (1H, broad).
Mass Spectrum (m/e): 427 (M+).

EXAMPLE 6

5-[4-(6-Acetyl-7-hydroxy-2,8-dimethyl-4-oxochroman-2-ylmethoxy)benzyl]thiazolidine-2,4-dione Following a procedure similar to that described in Example 1, 100 mg of the title compound were obtained from 200 mg of a mixture of ethyl 3-[4-(7-acetoxy-6-acetyl-2,8-dimethyl-4-oxochroman-2-ylmethoxy)-phenyl]-2-chloropropionate and ethyl 3-[4-(6-acetyl-7-hydroxy-2,8-dimethyl-4-oxochroman-2-ylmethoxy)-phenyl]-2-chloropropionate (prepared, as described in Preparation 23, as a crude product in which both compounds were present in nearly equal amounts), 38 mg of thiourea, 1 mg of thiourea, 1 ml of sulfolane, 2 ml of 2N aqueous hydrochloric acid and 2 ml of ethylene glycol monomethyl ether.

Nuclear Magnetic Resonance Spectrum (CDCl$_3$) δ ppm:
1.56 (3H, singlet);
2.07 (3H, singlet);
2.62 (3H, singlet);
2.74 (1H, doublet, J=16.5 Hz);
3.08 (1H, doublet of doublets, J=9 and 14 Hz);
3.10 (1H, doublet, J=16.5 Hz);
3.43 (1H, doublet of doublets, J=4 and 14 Hz);
4.02 and 4.14 (2H, AB-type, J=10 Hz);
4.47 (1H, doublet of doublets, J=4 and 9 Hz);
6.84 (2H, doublet, J=9 Hz);
7.16 (2H, doublet, J=9 Hz);
8.2–8.65 (1H, broad);
8.33 (1H, singlet);
13.26 (1H, singlet).
Mass Spectrum (m/e): 469 (M+).

EXAMPLE 7

5-[4-(2,5,7-Trimethylchroman-2-ylmethoxy)benzyl]-thiazolidine-2,4-dione

Following a procedure similar to that described in Example 1, but using 1.52 g of ethyl 2-chloro-3-[4-(2,5,7-trimethylchroman-2-ylmethoxy)phenyl]propionate (prepared as described in Preparation 27), 0.83 g of thiourea, 5 ml of sulfolane, 15 ml of ethylene glycol monomethyl ether and 4 ml of 3N aqueous hydrochloric acid, 1.18 g of the title compound were obtained as a pale yellow powder, softening at 85°–108° C.

Nuclear Magnetic Resonance Spectrum (hexadeuterated acetone) δ ppm:
1.37 (3H, singlet);
1.75–2.2 (2H, multiplet);
2.15 (3H, singlet);
2.17 (3H, singlet);
2.63 (2H, broad triplet, J=7 Hz);
3.09 (1H, doublet of doublets, J=14 and 9 Hz);
3.42 (1H, doublet of doublets, J=14 and 4 Hz);
3.97 (2H, singlet);
4.73 (1H, doublet of doublets, J=9 and 4 Hz);
6.45 (1H, broad singlet);
6.54 (1H, broad singlet);
6.93 (2H, doublet, J=8 Hz);
7.23 (2H, doublet, J=8 Hz).
Mass spectrum (m/e): 411 (M+).

EXAMPLE 8

5-[4-(2,5,7-Trimethyl-4-oxochroman-2-ylmethoxy)benzyl]thiazolidine-2,4-dione

Following a procedure similar to that described in Example 1, but using 1.5 g of ethyl 2-chloro-3-[4-(2,5,7-trimethyl-4-oxochroman-2-ylmethoxy)phenyl]propionate (prepared as described in Preparation 29), 0.4 g of thiourea, 1.5 ml of sulfolane, 10 ml of ethylene glycol monomethyl ether and 5 ml of 2N aqueous hydrochloric acid, 1.13 g of the title compound were obtained as a pale yellow powder.
Nuclear Magnetic Resonance Spectrum (CDCl$_3$) δ ppm:
 1.50 (3H, singlet);
 2.27 (3H, singlet);
 2.60 (3H, singlet);
 2.67 (1H, doublet, J=16.5 Hz);
 3.07 (1H, doublet, J=16.5 Hz);
 3.08 (1H, doublet of doublets, J=14 and 9 Hz);
 3.44 (1H, doublet of doublets, J=14 and 4 Hz);
 3.96 and 4.08 (2H, AB-type, J=9 Hz);
 4.48 (1H, doublet of doublets, J=9 and 4 Hz);
 6.63 (2H, broad singlet);
 6.85 (2H, doublet, J=9 Hz);
 7.16 (2H, doublet, J=9 Hz).
 8.35–8.75 (1H, broad).
Mass Spectrum (m/e): 425 (M+).

EXAMPLE 9

5-[4-(2,5,6,7,8-Pentamethylchroman-2-ylmethoxy)benzyl]thiazolidine-2,4-dione

Following a procedure similar to that described in Example 1, but using 361 mg of ethyl 2-chloro-3-[4-(2,5,6,7,8-pentamethylchroman-2-ylmethoxy)phenyl]-propionate (prepared as described in Preparation 33), 309 mg of thiourea, 3 ml of sulfolane, 10 ml of ethylene glycol monomethyl ether and 5 ml of 3N aqueous hydrochloric acid, 290 mg of the title compound were obtained as a white powder, softening at 62°–64° C.
Nuclear Magnetic Resonance Spectrum (hexadeuterated acetone) δ ppm:
 1.40 (3H, singlet);
 1.75–2.3 (2H, nd);
 2.07 (3H, singlet);
 2.13 (9H, singlet);
 2.68 (2H, broad triplet, J=7 Hz);
 3.10 (1H, doublet of doublets, J=14 and 9 Hz);
 3.43 (1H, doublet of doublets, J=14 and 4 Hz);
 4.00 (2H, singlet);
 4.75 (1H, doublet of doublets, J=9 and 4 Hz);
 6.93 (2H, doublet, J=9 Hz);
 7.23 (2H, doublet, J=9 Hz).
Mass Spectrum (m/e): 439 (M+).

EXAMPLE 10

5-[4-(7-Chloro-6-hydroxy-2-methyl-4-oxochroman-2-ylmethoxy)benzyl]thiazolidine-2,4-dione Following a procedure similar to that described in Example 1, but using 780 mg of ethyl 3-[4-(6-acetoxy-7-chloro-2-methyl-4-oxochroman-2-ylmethoxy)phenyl]-2-chloropropionate (prepared as described in Preparation 37), 360 mg of thiourea, 3 ml of sulfolane, 10 ml of ethylene glycol monomethyl ether and 5 ml of 3N aqueous hydrochloric acid, 286 mg of the title compound were obtained as a greyish white powder, softening at 195°–206° C.
Nuclear Magnetic Resonance Spectrum (hexadeuterated acetone) δ ppm:
 1.51 (3H, singlet);
 2.76 (1H, doublet, J=16 Hz);
 3.09 (1H, doublet, J=16 Hz);
 3.11 (1H, doublet of doublets, J=14 and 9 Hz);
 3.43 (1H, doublet of doublets, J=14 and 4 Hz);
 4.13 and 4.20 (2H, AB-type, J=11 Hz);
 4.76 (1H, doublet of doublets, J=9 and 4 Hz);
 6.91 (2H, doublet , J=9 Hz);
 7.01 (1H, singlet);
 7.23 (2H, doublet, J=9 Hz)
 7.40 (1H singlet).
Mass Spectrum (m/e): 447 (M+).

EXAMPLE 11

5-[4-(7-Hydroxy-2,8-dimethylchroman-2-ylmethoxy)-benzyl]thiazolidine-2,4-dione

Following a procedure similar to that described in Example 1, but using 1 g of ethyl 3-[4-(7-acetoxy-2,8-dimethylchroman-2-ylmethoxy)phenyl]-2-chloropropionate (prepared as described in Preparation 41), 0.22 g of thiourea, 1.5 ml of sulfolane, 10 ml of ethylene glycol monomethyl ether and 4 ml of 3N aqueous hydrochloric acid, 586 mg of the title compound were obtained as a pale yellow powder, softening at 68°–71° C.
Nuclear Magnetic Resonance Spectrum (CDCl$_3$) δ ppm:
 1.43 (3H, singlet);
 1.65–2.3 (2H, nd);
 2.03 (3H, singlet);
 2.71 (2H, broad triplet, J=7 Hz);
 3.07 (1H, doublet of doublets, J=9 and 14 Hz);
 3.43 (1H, doublet of doublets, J=4 and 14 Hz);
 3.90 and 3.98 (2H, AB-type, J=10 Hz);
 4.48 (1H, doublet of doublets, J=4 and 9 Hz);
 4.5–5.1 (1H, broad);
 6.35 (1H, doublet, J=8 Hz);
 6.78 (1H, doublet, J=8 Hz);
 6.87 (2H, doublet, J=8 Hz);
 7.15 (2H, doublet, J=8 Hz);
 8.0–9.0 (1H, broad).
Mass Spectrum (m/e): 413 (M+).

EXAMPLE 12 t-Butyl 2-[4-(2,4-dioxothiazolidin-5-ylmethyl)phenoxymethyl]-2,8-dimethyl-4-oxochroman-7-yloxyacetate 60 mg of sodium hydride (as a 55% w/w dispersion in mineral oil) were added to a solution of 280 mg of 5-[4-(7-hydroxy-2,8-dimethyl-4-oxochroman-2-ylmethoxy)-benzyl]thiazolidine-2,4-dione (prepared as described in Example 5) dissolved in 4 ml of dimethylformamide. The mixture was stirred at room temperature for 30 minutes, after which 140 mg of t-butyl bromocetate were added dropwise to it, whilst ice-cooling, and the resulting mixture was stirred at room temperature over a period of 30 minutes. The reaction mixture was then poured into ice-water and extracted with benzene. The extract was washed with water and dried over anhydrous sodium sulfate. The solvent was then removed by distillation under reduced pressure. The residue was purified by column chromatography through silica gel, eluted with a 4:1 by volume mixture of benzene and ethyl acetate, to afford 111 mg of the title compound.
Nuclear Magnetic Resonance Spectrum (hexadeuterated acetone) δ ppm:
 1.46 (9H, singlet);
 1.54 (3H, singlet);
 2.09 (3H, singlet);
 2.71 (1H, doublet, J=16.5 Hz);
 3.06 (1H, doublet, J=16.5 Hz);
 3.11 (1H, doublet of doublets, J=9 and 14 Hz);
 3.44 (1H, doublet of doublets, J=4 and 14 Hz);
 4.17 and 4.24 (2H, AB-type, J=10 Hz);
 4.73 (2H, singlet);
 4.7–4.85 (1H, nd);

6.62 (1H, doublet, J=9 Hz);
6.96 (2H, doublet, J=9 Hz).
7.25 (2H, doublet, J=9 Hz);
7.69 (1H, doublet, J=9 Hz).

EXAMPLE 13

2-[4-(2,4-Dioxothiazolidin-5-ylmethyl)phenoxymethyl]-2,8-dimethyl-4-oxochroman-7-yloxyacetic acid A mixture of 100 mg of t-butyl 2-[4-(2,4-dioxothiazolidin-5-ylmethyl)phenoxymethyl]-2,8-dimethyl-4-oxochroman-7-yloxyacetate (prepared as described in Example 12) and 2 ml of a 4N solution of hydrogen chloride in dioxane was allowed to stand overnight at room temperature. At the end of this time, the solvent was removed from the reaction mixture by evaporation under reduced pressure. The resulting residue was washed with water, to afford 84 mg of the title compound as a pale orange powder, softening at 176°–179° C.

Nuclear Magnetic Resonance Spectrum (hexadeuterated acetone) δ ppm:
1.54 (3H, singlet);
2.09 (3H, singlet);
2.70 (1H, doublet, J=16.5 Hz);
3.06 (1H, doublet, J=16.5 Hz);
3.10 (1H, doublet of doublets, J=9 and 14 Hz);
3.43 (1H, doublet of doublets, J=4 and 14 Hz);
4.17 and 4.24 (2H, AB-type, J=11 Hz);
4.75 (1H, doublet of doublets, J=4 and 9 Hz);
4.84 (2H, singlet);
5.0–6.60 (1H, broad, disappeared on adding D$_2$O);
6.65 (1H, doublet, J=9 Hz);
6.93 (2H, doublet, J=9 Hz);
7.24 (2H, doublet, J=9 Hz);
7.69 (1H, doublet, J=9 Hz);
10.2–11.0 (1H, broad, disappeared on adding D$_2$O).
Mass Spectrum (m/e): 485 (M+).

EXAMPLE 14

Ethyl 2-[4-(2,4-dioxothiazolidin-5-ylmethyl)phenoxymethyl]-2-methyl-4-oxochroman-6-carboxylate A procedure similar to that described in Example 1 was repeated, except that 4.7 g of methyl 2-[4-(2-chloro-2-ethoxycarbonylethyl)phenoxymethyl]-2-methyl-4-oxochroman-6-carboxylate (prepared as described in Preparation 45), 1 g of thiourea, 10 ml of sulfolane, 15 ml of acetic acid and 15 ml of 3N aqueous hydrochloric acid were used, to afford a crude 6-carboxylic acid corresponding to the title compound. This acid was treated, without purification, with 20 ml of ethanol and 2 ml of a 4N solution of hydrogen chloride in dioxane, following a procedure similar to that described in Preparation 43, to afford 2.7 g of the title compound as a pale yellow glassy substance.

Nuclear Magnetic Resonance Spectrum (CDCl$_3$) δ ppm:
1.39 (3H, triplet, J=7 Hz);
1.56 (3H, singlet);
2.75–3.05 (1H, nd);
2.80 (1H, doublet, J=16 Hz);
3.10 (1H, doublet, J=16 Hz);
3.43 (1H, doublet of doublets, J=4 and 14 Hz);
4.00 and 4.17 (2H, AB-type, J=10 Hz);
4.37 (2H, quartet, J=7 Hz);
4.4–4.6 (1H, nd);
6.81 (2H, doublet, J=9 Hz);
7.00 (1H, doublet, J=9 Hz);
7.15 (2H, doublet, J=9 Hz);
8.16 (1H, doublet of doublets, J=2 and 9 Hz);
8.4–9.3 (1H, broad);
8.59 (1H, doublet, J=2 Hz).
Mass Spectrum (m/e): 469 (M+).

EXAMPLE 15

2-[4-(2,4-Dioxothiazolidin-5-ylmethyl)phenoxymethyl]-2-methyl-4-oxochroman-6-carboxylic acid A mixture of 530 mg of ethyl 2-[4-(2,4-dioxothiazolidin-5-ylmethyl) phenoxymethyl]-2-methyl-4-oxochroman-6-carboxylate (prepared as described in Example 14), 4 ml of acetic acid and 2 ml of 3N aqueous hydrochloric acid was heated under reflux for 5 hours. At the end of this time, the solvent was removed from the reaction mixture by evaporation under reduced pressure, and the residue was dissolved in diethyl ether. The resulting solution was washed with a saturated aqueous solution of sodium chloride and dried over anhydrous sodium sulfate; the solvent was then removed by evaporation under reduced pressure. The resulting residue was washed with warm water to afford 342 mg of the title compound as a pale yellow powder, softening at 105°–108° C.

Nuclear Magnetic Resonance Spectrum (hexadeuterated acetone) δ ppm:
1.58 (3H, singlet);
2.86 (1H, doublet, J=17 Hz);
2.9–3.55 (2H, nd);
3.20 (1H, doublet, J=17 Hz);
4.17 and 4.26 (2H, AB-type, J=10 Hz);
4.71 (1H, doublet of doublets, J=4 and 9 Hz);
6.86 (2H, doublet, J=9 Hz);
7.04 (1H, doublet, J=9 Hz);
7.23 (2H, doublet, j=9 Hz);
8.14 (1H, doublet of doublets, J=2 and 9 Hz);
8.54 (1H, doublet, J=2 Hz).
Mass Spectrum (m/e): 441 (M+).

EXAMPLE 16

Ethyl 2-[4-(2,4-dioxothiazolidin-5-ylmethyl)phenoxymethyl]-2-methyl-2H-chromene-6-carboxylate A procedure similar to that described in Preparation 2 was repeated, except that 2.7 g of ethyl 2-[4-(2,4-dioxothiazolidin-5-ylmethyl)phenoxymethyl]-2-methyl-4-oxochroman-6-carboxylate (prepared as described in Example 14), 0.33 g of sodium borohydride and 40 ml of ethanol were used, to prepare the 4-hydroxy compound corresponding to the title compound. Using a procedure similar to that described in Preparation 3, this hydroxy compound was treated, without purification, with 0.1 g of p-toluenesulfonic acid monohydrate, 30 ml of benzene and 5 ml of dioxane, to afford 2.25 g of the title compound as a pale yellow glassy substance.

Nuclear Magnetic Resonance Spectrum (hexadeuterated acetone) δ ppm:
1.33 (3H, triplet, J=7 Hz);
1.56 (3H, singlet);
3.07 (1H, doublet of doublets, J=9 and 14 Hz);
3.41 (1H, doublet of doublets, J=4 and 14 Hz);
4.09 (2H, singlet);
4.29 (2H, quartet, J=7Hz);
4.71 (1H, doublet of doublets, J=4 and 9 Hz);
5.86 (1H, doublet, J=10 Hz);
6.63 (1H, doublet, J=10 Hz);
6.7–6.95 (1H, nd);
6.85 (2H, doublet, J=9 Hz);
7.19 (2H, doublet, J=9 Hz);
7.65–7.85 (2H, nd).

Mass Spectrum (m/e): 4.53 (M+).

EXAMPLE 17

Ethyl 2-[4-(2,4-dioxothiazolidin-5-ylmethyl)phenoxymethyl]-2-methylchroman-6-carboxylate 2.1 g of ethyl 2-[4-(2,4-dioxothiazolidin-5-ylmethyl)-phenoxymethyl]-2-methyl-2H-chromene-6-carboxylate (prepared as described in Example 16) were dissolved in 20 ml of acetic acid and hydrogenated for 20 hours under atmospheric pressure at 80° C. in the presence of 2 g of 10% w/w palladium-on-carbon. The catalyst was then removed by filtration, and the filtrate was freed from the solvent by evaporation under reduced pressure. The residue was purified by column chromatography through silica gel, eluted with a 4:1 by volume mixture of benzene and ethyl acetate, to afford 1.17 g of the title compound as a white powder.

Nuclear Magnetic Resonance Spectrum (hexadeuterated acetone) δ ppm:
  1.33 (3H, triplet, J=7 Hz);
  1.46 (3H, singlet);
  1.9–2.3 (2H, nd);
  2.89 (2H, broad triplet, J=7 Hz);
  3.10 (1H, doublet of doublets, J=9 and 14 Hz);
  3.43 (1H, doublet of doublets, J=4 and 14 Hz);
  4.05 (2H, singlet)
  4.28 (2H, quartet, J=7 Hz);
  4.74 (1H, doublet of doublets, J=4 and 9 Hz);
  6.81 (1H, doublet, J=9 Hz);
  6.93 (2H, doublet, J=9 Hz);
  7.23 (2H, doublet, J=9 Hz);
  7.65–7.85 (2H, nd).

Mass Spectrum (m/e): 455 (M+).

EXAMPLE 18

2-[4-(2,4-Dioxothiazolidin-5-ylmethyl)phenoxymethyl]-2-methylchroman-6-carboxylic acid A procedure similar to that described in Example 15 was repeated, except that 1.1 g of ethyl 2-[4-(2,4-dioxothiazolidin-5-ylmethyl)phenoxymethyl]-2-methylchroman-6-carboxylate (prepared as described in Example 17), 10 ml of acetic acid and 5 ml of 3N aqueous hydrochloric acid were used, to afford 814 mg of the title compound as colorless crystals, melting at 223°–225° C.

Nuclear Magnetic Resonance Spectrum (hexadeuterated dimethyl sulfoxide) δ ppm:
  1.38 (3H, singlet);
  1.7–2.3 (2H, multiplet);
  2.84 (2H, broad triplet, J=7 Hz);
  3.04 (1H, doublet of doublets, J=9 and 14 Hz);
  3.33 (1H, doublet of doublets, J=4 and 14 Hz);
  4.03 (2H, singlet)
  4.86 (1H, doublet of doublets, J=4 and 9 Hz);
  6.82 (1H, doublet, J=8 Hz);
  6.93 (2H, doublet, J=9 Hz);
  7.18 (2H, doublet, J=9 Hz);
  7.6–7.85 (2H, nd);
  11.5–13.0 (1H, broad).

Mass Spectrum (m/e): 427 (M+).

EXAMPLE 19

5-[4-(2-Methylchroman-2-ylmethoxy)benzyl]thiazolidine-2,4-dione sodium salt 48.6 ml of a 0.507N solution of sodium hydroxide in methanol were added to a solution of 9.44 g of 5-[4-(2-methylchroman-2-ylmethoxy)benzyl]thiazolidine-2,4-dione (prepared as described in Example 1) in 50 ml of methanol. When the reaction was complete, the mixture was freed from the solvent by evaporation under reduced pressure, to afford a powdery residue. This was washed with a 5:1 by volume mixture of diethyl ether and methanol and then with diethyl ether and dried, to afford 9.53 g of the title compound as a white powder, melting at 275°–285° C. (with decomposition).

EXAMPLE 20

(1) 5-[4-(2-Methyl-8-nitrochroman-2-ylmethoxy)benzyl]thiazolidine-2,4-dione and (2) 5-[4-(2-Methyl-6-nitrochroman-2-ylmethoxy)benzyl]thiazolidine-2,4-dione A mixture of 0.5 ml of concentrated sulfuric acid and 0.5 ml of concentrated nitric acid was added dropwise at 3°–7° C. to a solution of 0.5 g of 5-[4-(2-methylchroman-2-ylmethoxy)benzyl]thiazolidine-2,4-dione (prepared as described in Example 1) in 5 ml of nitrobenzene. Immediately the dropwise addition was complete, the reaction mixture was poured into water. The crude products were extracted with a mixture of benzene and ethyl acetate in a volume ratio of about 1:1. The extract was then washed with a saturated aqueous solution of sodium bicarbonate and then with a saturated aqueous solution of sodium chloride, after which it was dried over anhydrous sodium sulfate. The solvent was then distilled off in vacuo, and the residue was subjected to silica gel column chromatography eluted with a 7:1 by volume mixture of benzene and ethyl acetate, to give a viscous oil. This oil was subjected to reverse phase chromatography (RP-18) using a 3:2 by volume mixture of acetonitrile and water as eluent, to yield first 122 mg of a colorless glassy solid, softening at 43°–49° C., which was the title compound (1), and then 240 mg of a colorless glassy solid, softening at 52°–58° C., which was the title compound (2).

(1) Nuclear Magnetic Resonance Spectrum (270 MHz, hexadeuterated acetone) δ ppm:
  1.49 (3H, singlet);
  2.0–2.08 (2H, nd);
  2.2–2.32 (2H, multiplet);
  2.97 (2H, broad triplet, J=7 Hz);
  3.14 (1H, doublet of doublets, J=14 and 9 Hz);
  3.43 (1H, doublet of doublets, J=14 and 4 Hz);
  4.05 and 4.13 (2H, AB-type, J=9.8 Hz);
  4.77 (1H, doublet of doublets, J=9 and 4 Hz);
  6.94 (2H, doublet, J=8.8 Hz);
  6.95–7.0 (1H, nd);
  7.22 (1H, doublet, J=8.8 Hz);
  7.41 (1H, doublet of doublets, J=8.3 and 1.5 Hz);
  7.62 (1H, doublet of doublets, J=8.3 and 1.5 Hz);
  10.0–11.1 (1H, broad).

Mass Spectrum (m/e): 428 (M+).

(2) Nuclear Magnetic Resonance Spectrum (270 MHz, hexadeuterated acetone) δ ppm:
  1.50 (3H, singlet);
  2.0–2.08 (2H, nd);
  2.2–2.3 (2H, multiplet);
  3.01 (2H, broad triplet, J=7 Hz);
  3.15 (1H, doublet of doublets, J=14 and 9 Hz);
  3.43 (1H, doublet of doublets, J=14 and 4.4 Hz);
  4.09 and 4.14 (2H, AB-type, J=9.8 Hz);
  4.78 (1H, doublet of doublets, J=9 and 4.4 Hz);
  6.93 (1H, doublet, J=8.8 Hz);
  6.95 (2H, doublet, J=8.8 Hz);
  7.23 (2H, doublet, J=8.8 Hz);
  8.00 (1H, doublet of doublets, J=8.8 and 3 Hz);

8.07 (1H, doublet J=3 Hz);
10.3–10.9 (1H, broad).
Mass Spectrum (m/e): 428 (M+).

EXAMPLE 21

5-[4-(6-Amino-2-methylchroman-2-ylmethoxy)benzyl]-thiazolidine-2,4-dione

Following a procedure similar to that described in Preparation 4, 52 mg of the title compound were obtained by hydrogenation from 82 mg of 5-[4-(2-methyl-6-nitrochroman-2-ylmethoxy)benzyl]thiazolidine-2,4-dione (prepared as described in Example 20), using 110 mg of 10% w/w palladium-on-carbon and 15 ml of methanol. The compound was a pale brown powder.
Nuclear Magnetic Resonance Spectrum (270 MHz, $CD_3OD$) δ ppm:
1.37 (3H, singlet);
1.78–1.92 (1H, multiplet);
2.0–2.15 (1H, multiplet);
2.67–2.77 (2H, multiplet);
3.05 (1H, doublet of doublets, J=9.2 and 14.3 Hz);
3.37 (1H, doublet of doublets, J=4 and 14.3 Hz);
3.89 and 3.95 (2H, AB-type, J=9.5 Hz);
4.62 (1H, doublet of doublets, J=4 and 9.2 Hz);
6.48–6.55 (3H, nd);
6.87 (2H, doublet, J=8.8 Hz);
7.16 (2H, doublet, J=8.8 Hz).
Mass Spectrum (m/e): 398 (M+).

PREPARATION 1

2-Methyl-2-(4-nitrophenoxymethyl)-4-oxochroman 2 g of o-hydroxyacetophenone, 2.85 g of 4-nitrophenoxyacetone, 2 g of pyrrolidine and 280 mg of p-toluenesufonic acid monohydrate were dissolved in 10 ml of toluene, and the mixture was heated under reflux for 3 hours in apparatus equipped with a water separator. At the end of this time, the reaction mixture was washed with a saturated aqueous solution of sodium chloride and dried over anhydrous magnesium sulfate. The solvent was then distilled off under reduced pressure. The residue was subjected to silica gel column chromatography eluted with a 3:1 by volume mixture of benzene and ethyl acetate, to afford 2.5 g of the title compound as a pale yellow oily substance.
Nuclear Magnetic Resonance Spectrum ($CDCl_3$) δ ppm:
1.57 (3H, singlet);
2.76 (1H, doublet, J=17 Hz);
3.13 (1H, doublet, J=17 Hz);
4.12 and 4.25 (2H, AB-type, J=10 Hz);
6.85–7.15 (2H, nd);
6.98 (2H, doublet, J=10 Hz);
7.50 (1H, doublet of triplets, J=2 and 8 Hz);
7.91 (1H, doublet of doublets, J=2 and 7 Hz);
8.20 (2H, doublet, J=10 Hz).
Mass Spectrum (m/e): 313 (M+).

PREPARATION 2

4-Hydroxy-2-methyl-2-(4-nitrophenoxymethyl)chroman 120 mg of sodium borohydride were added gradually to a mixture of 1 g of 2-methyl-2-(4-nitrophenoxymethyl)-4-oxochroman (prepared as described in Preparation 1), 10 ml of methanol and 10 ml of tetrahydrofuran, in an ice bath. The resulting reaction mixture was stirred for 30 minutes in the ice bath, after which it was stirred for a further 30 minutes at room temperature. At the end of this time, dilute aqueous hydrochloric acid was added to the reaction mixture to acidify it, and then the mixture was extracted with ethyl acetate. The organic extract was dried over anhydrous magnesium sulfate, and then the organic solvent was removed by distillation under reduced pressure. The residue was subjected to silica gel column chromatography eluted with a 10:1 by volume mixture of benzene and ethyl acetate, to afford 710 mg of the title compound as a pale yellow oily substance.
Nuclear Magnetic Resonance Spectrum ($CDCl_3$) δ ppm:
1.57 (3H, singlet);
1.85–2.3 (1H, multiplet);
2.53 (1H, doublet of doublets, J=6 and 14 Hz);
3.99 and 4.08 (2H, AB-type, J=9 Hz);
4.75–5.1 (1H, multiplet);
6.75–7.55 (4H, multiplet);
6.96 (2H, doublet, J=9 Hz);
8.20 (2H, doublet, J=9 Hz).
Mass Spectrum (m/e): 315 (M+).

PREPARATION 3

2-Methyl-2-(4-nitrophenoxymethyl)-2H-chromene

A mixture of 1 g of 4-hydroxy-2-methyl-2-(4-nitrophenoxymethyl)chroman (prepared as described in Preparation 2), 70 mg of p-toluenesulfonic acid monohydrate and 10 ml of benzene was heated under reflux for 45 minutes. At the end of this time, the reaction mixture was washed with a saturated aqueous solution of sodium bicarbonate and then with a saturated aqueous solution of sodium chloride, after which it was dried over anhydrous magnesium sulfate. The solvent was then distilled off under reduced pressure. The residue was subjected to silica gel column chromatography eluted with a 20:1 by volume mixture of hexane and ethyl acetate, to afford 800 mg of the title compound as a pale yellow oily substance.
Nuclear Magnetic Resonance Spectrum ($CDCl_3$) δ ppm:
1.59 (3H, singlet);
4.12 (2H, singlet);
5.67 (1H, doublet, J=10 Hz);
6.52 (1H, doublet, J=10 Hz);
6.7–7.1 (3H, multiplet);
6.95 (2H, doublet, J=9 Hz);
7.18 (1H, doublet of doublets, J=2 and 7 Hz);
8.18 (2H, doublet, J=9 Hz).
Mass Spectrum (m/e): 297 (M+).

PREPARATION 4

2-(4-Aminophenoxymethyl)-2-methylchroman 780 mg of 2-methyl-2-(4-nitrophenoxymethyl)-2H-chromene (prepared as described in Preparation 3) were dissolved in 20 ml of methanol, and 160 mg of 10% w/w palladium-on-carbon were added to the solution. The solution was then hydrogenated at room temperature at a hydrogen pressure of about one atmosphere for about 10 hours. At the end of this time, the catalyst was filtered off, and the solvent was distilled off under reduced pressure. The residue was subjected to silica gel column chromatography eluted with a 2:1 by volume mixture of hexane and ethyl acetate, to afford 500 mg of the title compound as a pale yellow oily substance.
Nuclear Magnetic Resonance Spectrum ($CDCl_3$) δ ppm:
1.44 (3H, singlet);

1.7–2.3 (2H, multiplet);
2.77 (2H, triplet, J=7 Hz);
3.38 (2H, broad singlet, disappeared on adding $D_2O$);
3.83 and 3.93 (2H, AB-type, J=9 Hz);
6.55–7.3 (8H, multiplet).
Mass Spectrum (m/e): 269 (M+).

PREPARATION 5

Ethyl 2-chloro-3-[4-(2-methylchroman-2-ylmethoxy)-phenyl]propionate 0.7 ml of concentrated aqueous hydrochloric acid was dropped, whilst ice-cooling, into a solution of 500 mg of 2-(4-aminophenoxymethyl)-2-methylchroman (prepared as described in Preparation 4) in 5 ml of acetone, and then a solution of 170 mg of sodium nitrite in 2 ml of water was added dropwise to the resulting mixture. When the dropwise additon was complete, 2 ml of ethyl acrylate were added, and the reaction mixture was heated to 40° C. 10 mg of cuprous oxide were then added gradually, and the mixture was stirred for 30 minutes. At the end of this time, the acetone was distilled off under reduced pressure, and the residue was extracted with benzene. The benzene extract was dried over anhydrous magnesium sulfate. The solvent was then distilled off under reduced pressure. The residue was subjected of silica gel column chromatography eluted with a 10:1 dy volume mixture of hexane and ethyl acetate, to afford 350 mg of the title compound as a pale yellow oily substance.

Nuclear Magnetic Resonance Spectrum ($CDCl_3$) δ ppm:
1.23 (3H, triplet, J =7 Hz);
1.44 (3H, singlet);
1.7–2.3 (2H, multiplet);
2.77 (2H, triplet, J=7 Hz);
3.06 (1H, doublet of doublets, J=7 and 14 Hz);
3.32 (1H, doublet of doublets, J=7 and 14 Hz);
3.88 and 3.97 (2H, AB-type, J=9 Hz);
4.17 (2H, quartet, J=7 Hz);
4.36 (1H, triplet, J=7 Hz);
6.7–7.3 (8H, multiplet).
Mass Spectrum (m/e): 388 (M+).

PREPARATION 6

2-(4-Aminophenoxymethyl)-2-methyl-4-oxochroman

Following a procedure similar to that described in Preparation 4, 1.15 g of the title compound were obtained by hydrogenation from 1.46 g of 2-methyl-2-(4-nitrophenoxymethyl)-4-oxochroman (prepared as described in Preparation 1), 300 mg of 10% w/w palladium-on-carbon, 3 ml of methanol and 20 ml of benzene. The compound was a pale yellow oily substance.

Nuclear Magnetic Resonance Spectrum ($CDCl_3$) δ ppm:
1.50 (3H, singlet);
2.69 (1H, doublet, J=16.5 Hz);
3.13 (1H, doublet, J=16.5 Hz);
3.4 (2H, broad singlet, disappeared on adding $D_2O$);
3.92 and 4.04 (2H, AB-type, J=10 Hz);
6.5–7.1 (6H, multiplet);
7.46 (1H, doublet of triplets, J=2 and 7.5 Hz);
7.88 (1H, doublet of doublets, J=2 and 9 Hz).
Mass Spectrum (m/e): 283 (M+).

PREPARATION 7

Ethyl 2-chloro-3-[4-(2-methyl-4-oxochroman-2-ylmethoxy)-phenyl]propionate

Following a procedure similar to that described in Preparation 5, 910 mg of the title compound were obtained from 1.15 g of 2-(4-aminophenoxymethyl)-2-methyl-4-oxochroman (prepared as described in Preparation 6), 360 mg of sodium nitrite, 1.2 ml of concentrated aqueous hydrochloric acid, 4.1 ml of ethyl acrylate, 60 mg of cuprous oxide, 10 ml of acetone and 0.5 ml of water. The compound was a pale yellow oily substance.

Nuclear Magnetic Resonance Spectrum ($CDCl_3$) δ ppm:
1.23 (3H, triplet, J=7 Hz);
1.52 (3H, singlet);
2.72 (1H, doublet, J=16.5 Hz);
2.9–3.45 (2H, multiplet);
3.12 (1H, doublet, J=16.5 Hz);
3.96 and 4.11 (2H, AB-type , J=10 Hz);
4.17 (2H, quartet, J=7 Hz);
4.35 (1H, triplet, J=7 Hz);
6.75–7.3 (6H, multiplet);
7.35–7.6 (1H, multiplet);
7.8–8.0 (1H, multiplet).
Mass Spectrum (m/e): 402 (M+).

PREPARATION 8

6-Fluoro-2-methyl-2-(4-nitrophenoxymethyl)-4-oxochroman

Following a procedure similar to that described in Preparation 1, 6.28 g of the title compound were obtained from 5 g of 5-fluoro-2-hydroxyacetophenone, 6.33 g of 4-nitrophenoxyacetone, 4.5 g of pyrrolidine, 1.3 g of p-toluenesulfonic acid monohydrate and 70 ml of toluene. The compound was obtained as pale yellow crystals, melting at 132°–134° C.

Nuclear Magnetic Resonance Spectrum ($CDCl_3$) δ ppm:
1.57 (3H, singlet);
2.76 (1H, doublet, J=16.5 Hz);
3.14 (1H, doublet, J=16.5 Hz);
4.10 and 4.26 (2H, AB-type, J=10 Hz);
6.85–7.1 (1H, nd);
6.97 (2H, doublet, J=9 Hz);
7.1–7.4 (1H, multiplet);
7.57 (1H, doublet of doublets, J=3 and 8 Hz);
8.23 (2H, doublet, J=9 Hz).
Mass Spectrum (m/e): 331 (M+).

PREPARATION 9

6-Fluoro-4-hydropxy-2-methyl-2-(4-nitrophenoxymethyl)chroman

Following a procedure similar to that described in Preparation 2, 2.8 g of the title compound were obtained from 3 g of 6-fluoro-2-methyl-2-(4-nitrophenoxymethyl)-4-oxochroman (prepared as described in Preparation 8), 0.84 g of sodium borohydride, 30 ml of methanol and 10 ml of tetrahydrofuran. The compound was a pale yellow oily substance.

Nuclear Magnetic Resonance Spectrum ($CDCl_3$) δ ppm:
1.56 (3H, singlet);
1.97 (1H, doublet of doublets, J=8 and 13 Hz);
2.54 (1H, doublet of doublets, J=6 and 13 Hz);
3.97 and 4.07 (2H, AB-type, J=9 Hz);
4.75–5.05 (1H, multiplet);
6.65–7.1 (2H, nd);
6.96 (2H, doublet, J=9 Hz);
7.16 (1H, doublet of doublets, J=2 and 8 Hz);

8.21 (2H, doublet, J=9 Hz).
Mass Spectrum (m/e): 333 (M+).

PREPARATION 10

6-Fluoro-2-methyl-2-(4-nitrophenoxymethyl)-2H-chromene

Following a procedure similar to that described in Preparation 3, 2.3 g of the title compound were obtained from 2.7 g of 6-fluoro-4-hydroxy-2-methyl-2-(4-nitrophenoxymethyl)chroman (prepared as described in Preparation 9), 170 mg of p-toluenesulfonic acid monohydrate and 30 ml of benzene. The compound was obtained in the form of pale yellow crystals, melting at 95-98° C.

Nuclear Magnetic Resonance Spectrum (CDCl$_3$) δ ppm:
1.57 (3H, singlet);
4.11 (2H, singlet);
5.74 (1H, doublet, J=10 Hz);
6.45 (1H, doublet, J=10 Hz);
6.55-7.05 (3H, multiplet);
6.95 (2H, doublet, J=9 Hz);
8.20 (2H, doublet, J=9 Hz);
Mass Spectrum (m/e): 315 (M+).

PREPARATION 11

2-(4-Aminophenoxymethyl)-6-fluoro-2-methylchroman

Following a procedure similar to that described in Preparation 4, 1.44 g of the title compound were obtained by hydrogenation from 2.2 g of 6-fluoro-2-methyl-2-(4-nitrophenoxymethyl)-2H-chromene (prepared as described in Preparation 10), 450 mg of 10% w/w palladium-on-carbon, 15 ml of methanol and 5 ml of tetrahydrofuran. The compound was a pale yellow oily substance.

Nuclear Magnetic Resonance Spectrum (CDCl$_3$) δ ppm:
1.42 (3H, singlet);
1.65-2.3 (2H, multiplet);
2.76 (2H, triplet, J=7 Hz);
3.15-3.7 (2H, broad, disappeared on adding D$_2$O);
3.83 and 3.91 (2H, AB-type, J=10 Hz);
6.55-6.9 (7H, multiplet).
Mass Spectrum (m/e): 287 (M+).

PREPARATION 12

Ethyl 2-chloro-3-[4-(6-fluoro-2-methylchroman-2-ylmethoxy)phenyl]propionate

Following a procedure similar to that described in Preparation 5, 1.9 g of the title compound were obtained from 2 g of 2-(4-aminophenoxymethyl)-6-fluoro-2-methylchroman (prepared as described in Preparation 11), 630 mg of sodium nitrile, 2 ml of concentrated aqueous hydrochloric acid, 7.5 ml of ethyl acrylate, 100 mg of cuprous oxide, 20 ml of acetone and 2 ml of water. The compound was a pale yellow oily substance.

Nuclear Magnetic Resonance Spectrum (CDCl$_3$) δ ppm:
1.23 (3H, triplet, J=7 Hz);
1.42 (3H, singlet);
1.7-2.3, (2H, multiplet);
2.76 (2H, triplet, J=7 Hz);
3.07 (1H, doublet of doublets, J=7 and 14 Hz);
3.31 (1H, doublet of doublets, J=7 and 14 Hz);
3.89 and 3.96 (2H, AB-type, J=10 Hz);
4.18 (2H, quartet, J=7 Hz);
4.37 (1H, triplet, J=7 Hz);
6.7-6.95 (5H, nd),
7.15 (2H, doublet, J=9 Hz);
Mass Spectrum (m/e): 406 (M+).

PREPARATION 13

2-(4-Aminophenoxymethyl)-6-fluoro-2-methyl-4-oxochroman

Following a procedure similar to that described in Preparation 4, 570 mg of the title compound were obtained by hydrogenation from 0.9 g of 6-fluoro-2-methyl-2-(4-nitrophenoxymethyl)-4-oxochroman (prepared as described in Preparation 8), 180 mg of 10% w/w palladium-on-carbon, 10 ml of methanol and 10 ml of benzene. The compound was a pale yellow oily substance.

Nuclear Magnetic Resonance Spectrum (CDCl$_3$) δ ppm:
1.50 (3H, singlet);
2.71 (1H, doublet, J=16.5 Hz);
3.11 (1H, doublet, J=16.5 Hz);
3.29 (2H, broad singlet, disappeared on adding D$_2$O);
3.90 and 4.06 (2H, AB-type, J=10 Hz);
6.55-6.8 (4H, multiplet);
6.92 (1H, doublet of doublets, J=4 and 9 Hz);
7.05-7.35 (1H, multiplet);
7.54 (1H, doublet of doublets, J=3 and 8 Hz.
Mass Spectrum (m/e): 301 (M+).

PREPARATION 14

Ethyl 2-chloro-3-[4-(6-fluoro-2-methyl-4-oxochroman-2-ylmethoxy)phenyl]propionate Following a procedure similar to that described in Preparation 5, 610 mg of the title compound were obtained from 800 mg of 2-(4-aminophenoxymethyl)-6-fluoro-21-methyl-4-oxochroman (prepared as described in Preparation 13), 240 mg of sodium nitrite, 1 ml of concentrated aqueous hydrochloric acid, 2.8 ml of ethyl acrylate, 40 mg of cuprous oxide, 10 ml of acetone and 1 ml of water. The compound was a pale yellow oily substance.

Nuclear Magnetic Resonance Spectrum (CDCl$_3$) δ ppm:
1.24 (3H, triplet, J=7 Hz);
1.52 (3H, singlet);
2.74 (1H, doublet, J=16.5 Hz);
3.08 (1H, doublet of doublets, J=7 and 14 Hz);
3.12 (1H, doublet, J=16.5 Hz);
3.31 (1H, doublet of doublets, J=7 and 14 Hz);
3.97 and 4.14 (2H, AB-type, J=9 Hz);
4.18 (2H, quartet, J=7 Hz);
4.37 (1H, triplet, J=7 Hz);
6.82 (2H, doublet, J=9 Hz);
6.93 (1H, doublet of doublets, J=4 and 9 Hz);
7.05-7.35 (1H, nd);
7.16 (2H, doublet, J=9 Hz);
7.57 (1H, doublet of doublets, J=3 and 8 Hz);
Mass Spectrum (m/e): 420 (M+).

PREPARATION 15

7-Benzyloxy-2,8-dimethyl-2-(4-nitrophenoxymethyl)-4-oxochroman

Following a procedure similar to that described in Preparation 1, 13.5 g of the title compound were obtained from 11 g of 4-benzyloxy-2-hydroxy-3-methylacetophenone, 14 g of 4-nitrophenoxyacetone, 6.1 g of pyrrolidine, 2 g of p-toluenesulfonic acid monohydrate and 150 ml of benzene. The compound was a pale yellow oily substance.

Nuclear Magnetic Resonance Spectrum (CDCl$_3$) δ ppm:
1.57 (3H, singlet);
2.11 (3H, singlet);
2.70 (1H, doublet, J=16.5 Hz);
3.06 (1H, doublet, J=16.5 Hz):
4.13 and 4.23 (2H, AB-type, J=10 Hz);
5.15 (2H, singlet);
6.65 (1H, doublet, J=9 Hz);
6.98 (2H, doublet, J=9 Hz);
7.42 5H, singlet);
7.78 (1H, doublet, J=9 Hz);
8.18 (2H, doublet, J=9 Hz).

Mass Spectrm (m/e): 433 (M+).

PREPARATION 16

7-Hydroxy-2,8-dimethyl-2-(4-nitrophenoxymethyl)-4-oxochroman

A mixture of 13.5 g or 7-benzyloxy-2,8-dimethyl-2-(4-nitrophenoxymethyl)-4-oxochroman (prepared as described in Preparation 15, 40 ml of concentrated aqueous hydrochloric acid and 80 ml of acetic acid was heated under reflux for 3 hours. At the end of this time, the reaction mixture was poured into water and extracted with benzene. The benzene solution was washed with water and then dried over anhydrous sodium sulfate. The solvent was then distilled off under reduced pressure. Cyclohexane was added to the residue to crystallize it. 9.55 g of the title compound were obtained as a pale red powdery substance.

Nuclear Magnetic Resonance Spectrum; (hexadeuterated acetone) δ ppm:
1.57 (3H, singlet);
2.03 (3H, singlet);
2.70 (1H, doublet, J=16.5 Hz);
3.05 (1H, doublet, J=16.5 Hz);
4.41 (2H, singlet);
6.60 (1H, doublet, J=8 Hz);
7.22 (2H, doublet, J=9 Hz);
7.57 (1H, doublet, J=8 Hz);
8.23 (2H, doublet, J=9 Hz).

Mass Spectrum (m/e): 343 (M+).

PREPARATION 17

7-Acetoxy-2,8-dimethyl-2-(4-nitrophenoxymethyl)-4-oxochroman 3.3 g of acetic anhydride were added to a mixture of 9.3 g of 7-hydroxy-2,8-dimethyl-2-(4-nitrophenoxymethyl)-4-oxochroman (prepared as described in Preparation 16), 50 ml of pyridine and 50 ml of benzene and allowed to stand overnight. The reaction mixture was then poured into water and extracted with benzene. The benzene extract was washed with 5% w/v aqueous hydrochloric acid and then with water, after which it was dried over anhydrous sodium sulfate. The solvent was then distilled off under reduced pressure. The residue was subjected to silica gel column chromatography eluted with a 20:1 by volume mixture of benzene and ethyl acetate, to obtain 9.7 g of the title compound as a pale yellow oily substance.

Nuclear Magnetic Resonance Spectrum (CDCl$_3$) δ ppm:
1.58 (3H, singlet);
2.00 (3H, singlet);
2.32 (3H, singlet);
2.73 (1H, doublet, J=16.5 Hz);
3.10 (1H, doublet, J=16.5 Hz);
4.14 and 4.25 (2H, AB-type, J=10 Hz);
6.73 (1H, doublet, J=9 Hz);
6.97 (2H, doublet, J=9 Hz);
7.78 (1H, doublet, J=9 Hz);
8.20 (2H, doublet, J=9 Hz);

Mass Spectrum (m/e): 385 (M+).

PREPARATION 18

7-Acetoxy-2-(4-aminophenoxymethyl)-2,8-dimethyl-4-oxochroman

Following a procedure similar to that described in Preparation 4, 1.31 g of the title compound were obtained from 2.3 g of 7-acetoxy-2,8-dimethyl-2-(4-nitrophenoxymethyl)-4-oxochroman (prepared as described in Preparation 17), 500 mg of 10% w/w palladium-on-carbon, 10 ml of methanol and 10 ml of benzene. The compound was a pale red oily substance.

Nuclear Magnetic Resonance Spectrum (CDCl$_3$) δ ppm:
1.50 (3H, singlet);
2.02 (3H, singlet);
2.31 (3H, singlet);
2.68 (1H, doublet, J=16.5 Hz);
3.10 (1H, doublet, J=16.5 Hz);
3.2–3.9 (2H, broad);
3.94 and 4.06 (2H, AB-type, J=10 Hz);
6.5–6.9 (5H, multiplet);
7.79 (1H, doublet, J=9 Hz).

Mass Spectrum (m/e): 355 (M+).

PREPARATION 19

2-(4-Aminophenoxymethyl)-7-hydroxy-2,8-dimethyl-4-oxochroman

In the silica gel column chromatography described in Preparation 18, 490 mg of the title compound were obtained as a pale red oily substance from the fraction eluted after that containing the 7-acetoxy compound.

Nuclear Magnetic Resonance Spectrum (CDCl$_3$) δ ppm:
1.50 (3H, singlet);
2.07 (3H, singlet);
2.66 (1H, doublet, J=16.5 Hz);
3.05 (1H, doublet, J=16.5 Hz);
3.6–4.6 (2H, broad);
3.94 and 4.04 (2H, AB-type, J=10 Hz);
6.44 (1H, doublet, J=8 Hz);
6.5–6.85 (4H, multiplet);
7.66 (1H, doublet, J=8 Hz).

Mass Spectrum (m/e): 313 (M+).

PREPARATION 20

Ethyl 2-chloro-3-[4-(7-hydroxy-2,8-dimethyl-4-oxochroman-2-ylmethoxy)phenyl]propionate Following a procedure similar to that described in Preparation 5, 380 mg of the title compound were obtained from 1.8 g of a mixture of 7-acetoxy-2-(4-aminophenoxymethyl)-2,8-dimethyl-4-oxochroman and 2-(4-aminophenoxymethyl)-7-hydroxy-2,8-dimethyl-4-oxochroman (which can be obtained as a crude mixture in a ratio of about 5:2 by the procedure described in Preparation 18), 450 mg of sodium nitrite, 1.8 ml of concentrated aqueous hydrochloric acid, 5.4 ml of ethyl acrylate, 15 ml of acetone, 100 mg of cuprous oxide and 1 ml of water. The compound was a pale yellow oily substance.

Nuclear Magnetic Resonance Spectrum (CDCl$_3$) δ ppm:
1.23 (3H, triplet, J=7 Hz);
1.54 (3H, singlet);
2.08 (3H, singlet);
2.69 (1H, doublet, J=16.5 Hz);
2.96–3.2 (1H, nd);
3.07 (1H, doublet, J=16.5 Hz);
3.32 (1H, doublet of doublets, J=7 and 14 Hz);
4.02 and 4.11 (2H, AB-type, J=10 Hz);
4.20 (2H, quartet, J=7 Hz);
4.38 (1H, triplet, J=7 Hz);
6.52 (1H, doublet, J=9 Hz);
6.63 (1H, broad singlet);
6.85 (2H, doublet, J=9 Hz);
7.16 (2H, doublet, J=9 Hz);
7.71 (1H, doublet, J=9 Hz).
Mass Spectrum (m/e): 432 (M+).

PREPARATION 21

6-Acetyl-7-hydroxy-2,8-dimethyl-2-(4-nitrophenoxymethyl)-4-oxochroman

A mixture of 2.1 g of 7-acetoxy-2,8-dimethyl-2-(4-nitrophenoxymethyl)-4-oxochroman (prepared as described in Preparation 17) and 10 ml of a boron trifluoride-acetic acid complex (40%) was heated, whilst stirring, for 8 hours at 110° C. At the end of this time, the reaction mixture was poured into ice water and extracted with benzene. The benzene extract was washed with water and dried over anhydrous sodium sulfate. The solvent was then distilled off under reduced pressure. The residue was recrystallized from ethyl acetate to give 1.2 g of the title compound in the form of pale yellow crystals, melting at 215°–220° C. (with decomposition).

Nuclear Magnetic Resonance Spectrum (hexadeuterated dimethyl sulfoxide) δ ppm:
1.52 (3H, singlet);
1.96 (3H, singlet);
2.68 (3H, singlet);
2.87 (1H, doublet, J=16.5 Hz);
3.15 (1H, doublet, J=16.5 Hz);
4.41 (2H, broad singlet);
7.16 (2H, doublet, J=9 Hz);
8.19 (2H, doublet, J=9 Hz);
8.26 (1H, singlet);
13.26 (1H, broad singlet).
Mass Spectrum (m/e): 385 (M+).

PREPARATION 22

7-Acetoxy-6-acetyl-2,8-dimethyl-2-(4-nitrophenyoxymethyl)-4-oxochroman

Following a procedure similar to that described in Preparation 17, 810 mg of the title compound were obtained from 1 g of 6-acetyl-7-hydroxy-2,8-dimethyl-2-(4-nitrophenoxymethyl)-4-oxochroman (prepared as described in Preparation 21), 0.32 g of acetic anhydride and 5 ml of pyridine.

Nuclear Magnetic Resonance Spectrum (CDCl$_3$) δ ppm:
1.61 (3H, singlet);
2.04 (3H, singlet);
2.37 (3H, singlet);
2.55 (3H, singlet);
2.79 (1H, doublet, J=16.5 Hz);
3.16 (1H, doublet, J=16.5 Hz);
4.15 and 4.27 (2H, AB-type, J=10 Hz);
6.97 (2H, doublet, J=9 Hz);
8.22 (2H, doublet, J=9 Hz);
8.32 (2H, singlet).
Mass Spectrum (m/e): 427 (M+).

PREPARATION 23

Ethyl 3-[4-(6-acetyl-7-hydroxy-2,8-dimethyl-4-oxochroman-2-ylmethoxy)phenyl]-2-chloropropionate Following a procedure similar to that described in Preparation 4, 0.8 g of 7-acetoxy-6-acetyl-2,8-dimethyl-2-(4-nitrophenoxymethyl)-4-oxochroman (prepared as described in Preparation 22) was hydrogenated by using 0.2 g of 10% w/w/ palladium-on-carbon, 8 ml of methanol and 1 ml of benzene. The product was then reacted with 135 mg of sodium nitrite, 0.6 ml of concentrated aqueous hydrochloric acid, 1.6 ml of ethyl acrylate, 30 mg of cuprous oxide, 6 ml of acetone and 0.5 ml of water, following a procedure similar to that described in Preparation 5, to give the title compound in admixture with its 7-acetoxy compound in a ratio of about 1:1. The mixture was subjected to silica gel column chromatography eluted with a 10:1 by volume mixture of benzene and ethyl acetate, to afford the title compound as a pale yellow oily substance.

Nuclear Magnetic Resonance Spectrum (CDCl$_3$) δ ppm:
1.23 (3H, triplet, J=7 Hz);
1.55 (3H, singlet);
2.07 (3H, singlet);
2.6–3.2 (3H, nd);
2.61 (3H, singlet);
3.30 (1H, doublet of doublets, J=7 and 14 Hz);
3.9–4.2 (2H, nd);
4.17 (2H, quartet, J=7 Hz);
4.36 (1H, triplet, J=7 Hz);
6.82 (2H, doublet, J=9 Hz);
7.15 (2H, doublet, J=9 Hz);
8.32 (1H, singlet);
13.24 (1H, singlet).
Mass Spectrum (m/e): 474 (M+).

PREPARATION 24

2,5,7-Trimethyl-2-(4-nitrophenoxymethyl)-4-oxochroman

A procedure similar to that described in Preparation 1 was repeated, except that 10 g of 2-hydroxy-4,6-dimethylacetophenone, 12 g of 4-nitrophenoxyacetone, 6 ml of pyrrolidine, 3 g of p-toluenesulfonic acid monohydrate and 200 ml of benzene were reacted, to afford 6.36 g of the title compound, colored a pale yellow and melting at 86°–88.5° C.

Nuclear Magnetic Resonance Spectrum (CDCl$_3$) δ ppm:
1.52 (3H, singlet);
2.26 (3H, singlet);
2.59 (3H, singlet);
2.68 (1H, doublet, J=16.5 Hz);
3.07 (1H, doublet, J=16.5 Hz);
4.07 and 4.19 (2H, AB-type, J=10 Hz);
6.63 (2H, singlet);
6.96 (2H, doublet, J=9 Hz);
8.18 (2H, doublet, J=9 Hz);
Mass Spectrum (m/e): 341 (M+).

PREPARATION 25

2,5,7-Trimethyl-2-(4-nitrophenoxymethyl)-2H-chromene

A procedure similar to that described in Preparation 2 was repeated except that 3 g of 2,5,7-trimethyl-2-(4-nitrophenoxymethyl)-4-oxochroman (prepared as described in Preparation 24) 1 g of sodium borohydride, 10 ml of methanol and 20 ml of tetrahydrofuran were used, to afford the corresponding 4-hydroxy compound. This was dehydrated, without purification, by adding 30 mg of p-tuluenesulfonic acid monohydrate and 30 ml of benzene, following a procedure similar to that described in Preparation 3, to afford 2.2 g of the title compound, colored a pale yellow and melting at 116°–117.5° C.

Nuclear Magnetic Resonance Spectrum (CDCl$_3$) δ ppm:
1.55 (3H, singlet);
2.21 (3H, singlet);
2.25 (3H, singlet);
4.08 (2H, singlet);
5.63 (1H, doublet, J=10 Hz);
6.47 (1H, broad singlet);
6.55 (1H, broad singlet);
6.67 (1H, doublet, J=10 Hz);
6.95 (2H, doublet, J=9 Hz);
8.17 (2H, doublet, J=9 Hz).
Mass Spectrum (m/e): 325 (M+).

PREPARATION 26

2-(4-Aminophenoxymethyl)-2,5,7-trimethylchroman

Following a procedure similar to that described in Preparation 4, 2.1 g of 2,5,7-trimethyl-2-(4-nitrophenoxymethyl)-2H-chromene (prepared as described in Preparation 25) were hydrogenated at atmospheric pressure, using 200 mg of 10% w/w/ palladium-on-carbon, 20 ml of methanol and 50 ml of benzene, to afford 1.44 g of the title compound.

Nuclear Magnetic Resonance Spectrum (hexadeuterated acetone) δ ppm:
1.37 (3H, singlet);
1.75–2.2 (2H, multiplet);
2.15 (2H, singlet);
2.17 (3H, singlet);
2.4–3.05 (2H, broad);
2.62 (2H, broad triplet, J=7 Hz);
3.80 and 3.94 (2H, AB-type, J=10 Hz);
6.4–7.0 (6H, multiplet).
Mass Spectrum (m/e); 297 (M+).

PREPARATION 27

Ethyl 2-chloro-3-[4-(2,5,7-trimethylchroman-2-ylmethoxy)phenyl]propionate

A procedure similar to that described in Preparation 5 was repeated, except that 2.0 g of 2-(4-aminophenoxymethyl)-2,5,7-trimethylchroman (prepared as described in Preparation 26), 2 ml of concentrated aqueous hydrochloric acid, 560 mg of sodium nitrite, 15 ml of acetone, 3.5 ml of ethyl acrylate, 90 mg of cuprous oxide and 2 ml of water were reacted, to afford 1.53 g of the title compound as a pale yellow oil.

Nuclear Magnetic Resonance Spectrum (CDCl$_3$) δ ppm:
1.22 (3H, triplet, J=7 Hz);
1.41 (3H, singlet);
1.75–2.3 (2H, nd);
2.17 (3H, singlet);
2.23 (3H, singlet);
2.59 (2H, broad triplet, J=7 Hz);
3.07 (1H, doublet of doublets, J=14 and 7 Hz);
3.30 (1H, doublet of doublets, J=14 and 7 Hz);
3.86 and 3.95 (2H, AB-type, J=9 Hz);
4.17 (2H, quartet, J=7 Hz);
4.36 (1H, triplet, J=7 Hz);
6.55 (1H, broad singlet);
6.57 (1H, broad singlet);
6.85 (2H, doublet, J=9 Hz);
7.14 (2H, doublet, J=9 Hz).
Mass Spectrum (m/e): 416 (M+).

PREPARATION 28

2-(4-Aminophenoxymethyl)-2,5,7-trimethyl-4-oxochroman

Following a procedure similar to that described in Preparation 4, 2.0 g of 2,5,7-trimethyl-2-(4-nitrophenoxymentyl)-4-oxochroman (prepared as described in Preparation 24) were hydrogenated at atmospheric pressure, using 400 mg of 10% w/w/ palladium-on-carbon, 5 ml of methanol and 15 ml of benzene, to afford 1.5 g of the title compound as a pale yellow oil.

Nuclear Magnetic Resonance Spectrum (CDCl$_3$) δ ppm:
1.47 (3H, singlet);
2.26 (3H, singlet);
2.60 (3H, singlet);
2.63 (1H, doublet, J=16.5 Hz);
3.07 (1H, doublet, J=16.5 Hz);
3.40 (2H, broad singlet);
3.90 and 4.01 (2H, AB-type, J=10 Hz);
6.5–6.9 (6H, multiplet).
Mass Spectrum (m/e): 311 (M+).

PREPARATION 29

Ethyl 2-chloro-3-[4-(2,5,7-trimethyl-4-oxochroman-2-ylmethoxy)phenyl]propionate

A procedure similar to that described in Preparation 5 was repeated, except that 1.8 g of 2-(4-aminophenoxymethyl)-2,5,7-trimethyl-4-oxochroman (prepared as described in Preparation 28), 2 ml of concentrated aqueous hydrochloric acid, 520 mg of sodium nitrite, 6 ml of ethyl acrylate, 83 mg of cuprous oxide, 20 ml of acetone and 1 ml of water were reacted, to afford 1.52 g of the title compound as a pale yellow oil.

Nuclear Magnetic Resonance Spectrum (CDCl$_3$) δ ppm:
1.25 (3H, triplet, J=7 Hz);
1.51 (3H, singlet);
2.29 (3H, singlet);
2.62 (3H, singlet);
2.68 (1H, doublet, J=16 Hz);
3.08 (1H, doublet, J=16 Hz);
3.09 (1H, doublet of doublets, J=15 and 7 Hz);
3.32 (1H, doublet of doublets, J=15 and 7 Hz);
3.96 and 4.08 (2H, AB-type, J=9 Hz);
4.20 (2H, quartet, J=7 Hz);
4.38 (1H, triplet, J=7 Hz);
6.65 (2H, broad singlet);
6.86 (2H, doublet, J=9 Hz);
7.17 (2H, doublet, J=9 Hz).
Mass Spectrum (m/e): 430 (M+).

PREPARATION 30

2,5,6,7,8-Pentamethyl-2-(4-nitrophenoxymethyl)-4-oxochroman

Following a procedure similar to that described in Preparation 1, a mixture of 1.44 g of 2-hydroxy-3,4,5,6-tetramethylacetophenone, 1.46 g of 4-nitrophenoxyacetone, 1.3 ml of pyrrolidine and 15 ml of methanol was heated under reflux for 4.5 hours. The mixture was then cooled, after which it was acidified by the addition of 3N aqueous hydrochloric acid, and then the methanol was removed by distillation under reduced pressure. The residue was extracted with benzene. The extract was washed with water, dried and concentrated by evaporation under reduced pressure. The residue was subjected to column chromatography through silica gel, eluted with a 50:1 by volume mixture of benzene and ethyl acetate, to afford 1.83 g of the title compound as an orange oil.

Nuclear Magnetic Resonance Spectrum (CDCl$_3$) δ ppm:
 1.54 (3H, singlet);
 2.12 (3H, singlet);
 2.18 (3H, singlet);
 2.24 (3H, singlet);
 2.60 (3H, singlet);
 2.71 (1H, doublet, J=16 Hz);
 3.05 (1H, doublet, J=16 Hz);
 4.13 and 4.20 (2H, AB-type, J=11 Hz);
 6.98 (2H, doublet, J=9 Hz);
 8.20 (2H, doublet, J=9 Hz).

Mass Spectrum (m/e): 369 (M+).

PREPARATION 31

2,5,6,7,8-Pentamethyl-2-(4-nitrophenoxymethyl)-2H-chromene

A procedure similar to that described in Preparation 25 was repeated, except that 1 g of 2,5,6,7,8-pentamethyl-2-(4-nitrophenoxymethyl)-4-oxochroman (prepared as described in Preparation 30) 300 mg of sodium borohydride, 5 ml of methanol and 10 ml of tetrahydrofuran were reacted, to afford the corresponding 4-hydroxy compound. This was then dehydrated using 20 mg of p-toluenesulfonic acid monohydrate and 20 ml of benzene, to afford 800 mg of the title compound as crystals, melting at 142°–145° C.

Nuclear Magnetic Resonance Spectrum (CDCl$_3$) δ ppm:
 1.57 (3H, singlet);
 2.07 (3H, singlet);
 2.17 (6H, singlet);
 2.23 (3H, singlet);
 4.03 and 4.13 (2H, AB-type, J=10 Hz);
 5.66 (1H, doublet, J=10 Hz);
 6.79 (1H, doublet, J=10 Hz);
 6.94 (2H, doublet, J=9 Hz);
 8.17 (2H, doublet, J=9 Hz).

Mass Spectrum (m/e): 353 (M+).

PREPARATION 32

2-(4-Aminophenoxymethyl)-2,5,6,7,8-pentamethylchroman

Following a procedure similar to that described in Preparation 4, 760 mg of 2,5,6,7,8-pentamethyl-2-(4-nitrophenoxymethyl)-2H-chromene (prepared as described in Preparation 31) were hydrogenated, using 100 mg of 10% w/w palladium-on-carbon, 20 ml of methanol and 70 ml of benzene, at atmospheric pressure, to afford 520 mg of the title compound as a pale yellow oil.

Nuclear Magnetic Resonance Spectrum (CDCl$_3$) δ ppm:
 1.41 (3H, singlet);
 1.7–2.3 (2H, nd);
 2.14 (6H, singlet);
 2.17 (3H, singlet);
 2.20 (3H, singlet);
 2.66 (2H, broad triplet, J=7 Hz);
 3.12 (2H, broad singlet);
 3.78 and 3.94 (2H, AB-type, J=10 Hz);
 6.55–6.9 (4H, multiplet).

Mass Spectrum (m/e): 325 (M+).

PREPARATION 33

Ethyl 2-chloro-3-[4-(2,5,6,7,8-pentamethylchroman-2-ylmethoxy)phenyl]propionate

A procedure similar to that described in Preparation 5 was repeated, except that 734 mg of 2-(4-aminophenoxymethyl)-2,5,6,7,8-pentamethylchroman (prepared as described in Preparation 32), 1 ml of concentrated aqueous hydrochloric acid, 190 mg of sodium nitrite, 1.2 ml of ethyl acrylate, 70 mg of cuprous oxide, 10 ml of acetone and 2 ml of water were reacted, to afford 390 mg of the title compound as a pale yellow oil.

Nuclear Magnetic Resonance Spectrum (CDCl$_3$) δ ppm:
 1.23 (3H, triplet, J=7 Hz);
 1.42 (3H, singlet);
 1.7–2.3 (2H, nd);
 2.14 (6H, singlet);
 2.17 (3H, singlet);
 2.19 (3H, singlet);
 2.66 (2H, broad triplet, J=7 Hz);
 3.06 (1H, doublet of doublets, J=14 and 7 Hz);
 3.31 (1H, doublet of doublets, J=14 and 7 Hz);
 3.86 and 3.97 (2H, AB-type, J=9 Hz);
 4.17 (2H, quartet, J=7 Hz);
 4.36 (1H, triplet, J=7 Hz);
 6.85 (2H, doublet, J=9 Hz);
 7.13 (2H, doublet, J=9 Hz).

Mass Spectrum (m/e): 444 (M+).

PREPARATION 34

7-Chloro-6-hydroxy-2-methyl-2-(4-nitrophenoxymethyl)-4-oxochroman

A procedure similar to that described in Preparation 1 was repeated, except that 2 g of 4-chloro-2,5-dihydroxyacetophenone, 2 g of 4-nitrophenoxyacetone, 1.2 ml of pyrrolidine, 0.6 g of p-toluenesulfonic acid monohydrate and 30 ml of benzene were reacted, to afford 2.86 g of the title compound.

Nuclear Magnetic Resonance Spectrum (CDCl$_3$) δ ppm:
 1.53 (3H, singlet);
 2.75 (1H, doublet, J=16.5 Hz);
 3.12 (1H, doublet, J=16.5 Hz);
 4.08 and 4.23 (2H, AB-type, J=10 Hz);
 5.8–6.5 (1H, broad);
 6.96 (2H, doublet, J=9 Hz);
 6.99 (1H, singlet);
 7.51 (1H, singlet);
 8.18 (2H, doublet, J=9 Hz).

Mass Spectrum (m/e): 363 (M+).

PREPARATION 35

6-Acetoxy-7-chloro-2-methyl-2-(4-nitrophenoxymethyl)-4-oxochroman

A procedure similar to that described in Preparation 17 was repeated, except that 550 mg of 7-chloro-6-hydroxy-2-methyl-2-(4-nitrophenoxymethyl)-4-oxochroman (prepared as described in Preparation 34), 1 ml of acetic anhydride and 10 ml of pyridine were reacted, to afford 580 mg of the title compound as a pale yellow glassy substance.

Nuclear Magnetic Resonance Spectrum (CDCl$_3$) δ ppm:
1.56 (3H, singlet);
2.32 (3H, singlet);
2.75 (1H, doublet, J=17 Hz);
3.12 (1H, doublet, J=17 Hz);
4.08 and 4.24 (2H, AB-type, J=9 Hz);
6.95 (2H, doublet, J=9 Hz);
7.08 (1H, singlet);
7.65 (1H, singlet);
8.21 (2H, doublet, J=9 Hz).
Mass Spectrum (m/e): 405 (M+).

PREPARATION 36

6-Acetoxy-2-(4-aminophenoxymethyl)-7-chloro-2-methyl-4-oxochroman 1 g of zinc powder was added in portions to a solution of 740 mg of 6-acetoxy-7-chloro-2-methyl-2-(4-nitrophenoxymethyl)-4-oxochroman (prepared as described in Preparation 35) dissolved in 15 ml of acetic acid. The reaction mixture was stirred for 2 hours, after which it was poured into a saturated aqueous solution of sodium bicarbonate whilst ice-cooling, and the mixture was then extracted with benzene. The extract was washed with water and dried over anhydrous sodium sulfate, after which the solvent was removed by evaporation under reduced pressure. The residue was subjected to column chromatography through silica gel, eluted with a 1:1 by volume mixture of benzene and ethyl acetate, to afford 280 mg of the title compound as a pale yellow oil.

Nuclear Magnetic Resonance Spectrum (CDCl$_3$) δ ppm:
1.50 (3H, singlet);
2.32 (3H, singlet);
2.70 (1H, doublet, J=16 Hz);
3.10 (1H, doublet, J=16 Hz);
3.1–3.9 (2H, broad);
3.90 and 4.05 (2H, AB-type, J=10 Hz);
6.5–6.8 (4H, multiplet);
7.09 (1H, singlet);
7.64 (1H, singlet).
Mass Spectrum (m/e): 375 (M+).

PREPARATION 37

Ethyl 3-[4-(6-acetoxy-7-chloro-2-methyl-4-oxochroman-2-ylmethoxy)phenyl]-2-chloropropionate A procedure similar to that described in Preparation 5 was repeated, except that 1.44 g of 6-acetoxy-2-(4-aminophenoxymethyl)-7-chloro-2-methyl-4-oxochroman (prepared as described in Preparation 36), 1.8 ml of concentrated aqueous hydrochloric acid, 330 mg of sodium nitrite, 18 ml of acetone, 3.7 ml of ethyl acrylate, 330 mg of cuprous oxide and 3 ml of water were reacted, to afford 600 mg of the title compound as a pale yellow oil.

Nuclear Magnetic Resonance Spectrum (CDCl$_3$) δ ppm:
1.24 (3H, triplet, J=7 Hz);
1.53 (3H, singlet);
2.32 (3H, singlet);
2.73 (1H, doublet, J=16 Hz);
3.07 (1H, doublet of doublets, J=14 and 7 Hz);
3.12 (1H, doublet, J=16 Hz);
3.31 (1H, doublet of doublets, J=14 and 7 Hz);
3.97 and 4.11 (2H, AB-type, J=10 Hz);
4.18 (2H, quartet, J=7 Hz);
4.36 (1H, triplet, J=7 Hz);
6.82 (2H, doublet, J=9 Hz);
7.08 (1H, singlet);
7.14 (2H, doublet, J=9 Hz);
7.64 (1H, singlet).
Mass Spectrum (m/e): 494 (M+).

PREPARATION 38

7-Acetoxy-4-hydroxy-2,8-dimethyl-2-(4-nitrophenoxymethyl)chroman

A procedure similar to that described in Preparation 2 was repeated, except that 5 g of 7-acetoxy-2,8-dimethyl-2-(4-nitrophenoxymethyl)-4-oxochroman (prepared as described in Preparation 17), 980 mg of sodium borohydride and 20 ml of methanol were reacted, to afford 2.77 g of the title compound as a pale yellow oil.

Nuclear Magnetic Resonance Spectrum (CDCl$_3$) δ ppm:
1.57 (3H, singlet);
1.9–2.25 (1H, nd);
1.95 (3H, singlet);
2.29 (3H, singlet);
2.47 (1H, doublet of doublets, J=6 and 14 Hz);
3.98 and 4.07 (2H, AB-type, J=10 Hz);
4.18 (1H, broad singlet);
4.7–5.0 (1H, multiplet);
6.66 (1H, doublet, J=9 Hz);
6.96 (2H, doublet, J=10 Hz);
7.26 (1H, doublet, J=9 Hz);
8.18 (2H, doublet, J=10 Hz).
Mass Spectrum (m/e): 387 (M+).

PREPARATION 39

7-Acetoxy-2,8-dimethyl-2-(4-nitrophenoxymethyl)-2H-chromene

A procedure similar to that described in Preparation 3 was repeated, except that 4.1 g of 7-acetoxy-4-hydroxy-2,8-dimethyl-2-(4-nitrophenoxymethyl)chroman (prepared as described in Preparation 38), 220 mg of p-toluenesulfonic acid monohydrate and 50 ml of benzene were reacted, to afford 2.66 g of the title compound as a pale yellow oil.

Nuclear Magnetic Resonance Spectrum (CDCl$_3$) δ ppm:
1.58 (3H, singlet);
1.91 (3H, singlet);
2.27 (3H, singlet);
4.10 (2H, singlet);
5.63 (1H, doublet, J=10 Hz);
6.47 (1H, doublet, J=10 Hz);
6.58 (1H, doublet, J=7 Hz);
6.86 (1H, doublet, J=7 Hz);
6.93 (2H, doublet, J=9 Hz);
8.18 (2H, doublet, J=9 Hz).
Mass Spectrum (m/e): 369 (M$^{30}$).

PREPARATION 40

7-Acetoxy-2-(4-aminophenoxymethyl)-2,8-dimethylchroman

Following a procedure similar to that described in Preparation 4, 1.6 g of 7-acetoxy-2,8-dimethyl-2-(4-nitrophenoxymethyl)-2H-chromene (prepared as described in Preparation 39) was hydrogenated, using 0.2 g of 10% w/w palladium-on-carbon and 15 ml of methanol, to afford 1.35 g of the title compound as a pale brown oil.

Nuclear Magnetic Resonance Spectrum (CDCl$_3$) δ ppm:
1.43 (3H, singlet);
1.7–2.3 (2H, nd);
1.97 (3H, singlet);
2.29 (3H, singlet);
2.74 (2H, broad triplet, J=7 Hz);
3.1–3.7 (2H, broad);
3.83 and 3.93 (2H, AB-type, J=9 Hz);
6.45–7.0 (6H, multiplet).
Mass Spectrum (m/e): 341 (M+).

PREPARATION 41

Ethyl 3-[4-(7-acetoxy-2,8-dimethylchroman-2-ylmethoxy)-phenyl]-2-chloropropionate A procedure similar to that described in Preparation 5 was repeated, except that 1.3 g of 7-acetoxy-2-(4-aminophenoxymethyl)-2,8-dimethylchroman (prepared as described in Preparation 40), 340 mg of sodium nitrite, 1.3 ml of concentrated aqueous hydrochloric acid, 4 ml of ethyl acrylate, 60 mg of cuprous oxide, 10 ml of acetone and 0.5 ml of water were reacted, to afford 1.0 g of the title compound as a pale yellow oil.

Nuclear Magnetic Resonance Spectrum (CDCl$_3$) δ ppm:
1.23 (3H, triplet, J=7 Hz);
1.44 (3H, singlet);
1.7–2.3 (2H, nd);
1.96 (3H, singlet);
2.28 (3H, singlet);
2.74 (2H, broad triplet, J=7 Hz);
3.06 (1H, doublet of doublets, J=7 and 14 Hz);
3.31 (1H, doublet of doublets, J=7 and 14 Hz);
3.88 and 3.98 (2H, AB-type, J=9 Hz);
4.17 (2H, quartet, J=7 Hz);
4.25–4.5 (1H, nd);
6.53 (1H, doublet, J=8 Hz);
6.86 (2H, doublet, J=9 Hz);
6.90 (1H, doublet, J=8 Hz);
7.15 (2H, doublet, J=9 Hz).
Mass Spectrum (m/e): 460 (M+).

PREPARATION 42

2-Methyl-2-(4-nitrophenoxymethyl)-4-oxochroman-6-carboxylic acid

A procedure similar to that described in Preparation 1 was repeated, except that 10 g of 3-acetyl-4-hydroxybenzoic acid, 13 g of 4-nitrophenoxyacetone, 7.9 g of pyrrolidine, 2.6 g of p-toluenesulfonic acid monohydrate and 150 ml of benzene were reacted, to afford 17.6 g of the title compound as pale brown crystals, melting at 227°–235° C.

Nuclear Magnetic Resonance Spectrum (hexadeuterated dimethyl sulfoxide) δ ppm:
1.51 (3H, singlet);
2.95 (1H, doublet, J=17 Hz);
3.21 (1H, doublet, J=17 Hz);
4.39 (2H, singlet);
7.09 (1H, doublet, J=9 Hz);
7.13 (2H, doublet, J=9 Hz);
8.07 (1H, doublet of doublets, J=2 and 9 Hz);
8.21 (2H, doublet, J=9 Hz);
8.36 (1H, doublet, J=2 Hz).
Mass Spectrum (m/e): 357 (M+).

PREPARATION 43

Methyl 2-methyl-2-(4-nitrophenoxymethyl)-4-oxochroman-6-carboxylate

A mixture of 22 g of 2-methyl-2-(4-nitrophenoxymethyl)-4-oxochroman-6-carboxylic acid (prepared as described in Preparation 42), 100 ml of methanol and 200 ml of a 4N solution of hydrogen chloride in dioxane was allowed to stand overnight at room temperature. At the end of this time, the solvent was stripped from the reaction mixture by evaporation under reduced pressure. The residue was then dissolved in benzene, and the resulting solution was washed with water and dried over anhydrous sodium sulfate. The solvent was then removed by evaporation under reduced pressure. The residue was purified by column chromatography through silica gel, eluted with a 20:1 by volume mixture of benzene and ethyl acetate, to afford 16.1 g of the title compound, melting at 144°–145° C.

Nuclear Magnetic Resonance Spectrum (hexadeuterated acetone) δ ppm:
1.60 (3H, singlet);
2.91 (1H, doublet, J=16.5 Hz);
3.25 (1H, doublet, J=16.5 Hz);
3.87 (3H, singlet);
4.40 and 4.50 (2H, AB-type, J=10 Hz);
7.07 (1H, doublet, J=9 Hz);
7.16 (2H, doublet, J=9 Hz);
8.11 (1H, doublet of doublets, J=2 and 9 Hz);
8.21 (2H, doublet, J=9 Hz);
8.48 (1H, doublet, J=2 Hz).
Mass Spectrum (m/e): 371(M+).

PREPARATION 44

Methyl 2-(4-aminophenoxymethyl)-2-methyl-4-oxochroman-6-carboxylate

Following a procedure similar to that described in Preparation 4, 10 g of methyl 2-methyl-2-(4-nitrophenoxymethyl)-4-oxochroman-6-carboxylate (prepared as described in Preparation 43) were hydrogenated, using 2 g of 10% w/w palladium-on-carbon, 100 ml of methanol and 200 ml of benzene, to afford 7.3 g of the title compound as a pale yellow oil.

Nuclear Magnetic Resonance Spectrum (CDCl$_3$) δ ppm:
1.52 (3H, singlet);
2.75 (1H, doublet, J=17 Hz);
3.16 (1H, doublet, J=17 Hz);
3.42 (2H, broad singlet);
3.91 (3H, singlet);
3.93 and 4.09 (2H, AB-type, J=10 Hz);
6.5–6.8 (4H, multiplet);
6.99 (1H, doublet, J=9 Hz);
8.15 (1H, doublet of doublets, J=2 and 9 Hz);
8.60 (1H, doublet, J=2 Hz);
Mass Spectrum (m/e): 341 (M+).

PREPARATION 45

Methyl 2-[4-(2-chloro-2-ethoxycarbonylethyl)phenoxyemthyl]-2-methyl-4-oxochroman-6-carboxylate A procedure similar to that described in Preparation 5 was repeated, except that 7.2 g of methyl 2-(4-aminophenoxymethyl)-2-methyl-4-oxochroman-6-carboxylate (prepared as described in Preparation 44), 1.9 g of sodium nitrite, 7.2 ml of concentrated aqueous hydrochloric acid, 22.5 ml of ethyl acrylate, 0.3 g of cuprous oxide, 70 ml of acetone and 5 ml of water were reacted, to afford 7.2 g of the title compound as a pale yellow oil.

Nuclear Magnetic Resonance Spectrum (CDCl$_3$) δ ppm:
1.26 (1H, triplet, J=7 Hz);
1.54 (3H, singlet);
2.77 (1H, doublet, J=16 Hz);
2.9-3.45 (2H, nd);
3.15 (1H, doublet, J=16 Hz);
3.90 (3H, singlet);
3.9-4.2 (2H, nd);
4.17 (2H, quartet, J=7 Hz);
4.36 (1H, triplet, J=6 Hz);
6.79 (2H, doublet, J=8 Hz);
7.00 (1H, doublet, J=9 Hz);
7.14 (2H, doublet, J=8 Hz);
8.15 (1H, doublet of doublets, J=2 and 9 Hz);
8.6 (1H, doublet, J=2 Hz).

Mass Spectrum (m/e): 460 (M+).

Test Example

BIOLOGICAL ACTIVITY

Effect on Hyperglycemia

The test animals employed were genetically diabetic male mice of the KK strain, aged about 4 months. The animals were employed in groups of 3 (test compound) or 5 (control) for each test.

The test compound (Compound No. 1-3, the compound prepared as described in Example 1) was suspended in a 0.5% w/v aqueous solution of carboxymethylcellulose and administered to a dose of 50 mg/kg body weight. A control group was tested similarly, except that the test compound was omitted. The animals were observed for several days after administration.

It was found that the blood glucose level in the animals to which the test compound was administered decreased by approximately 40 to 50% as compared with that of the control group. Moreover, the effect lasted, at its best, for 48 hours and was accompanied by a reduction in blood lipid levels.

We claim:

1. A compound of formula (I):

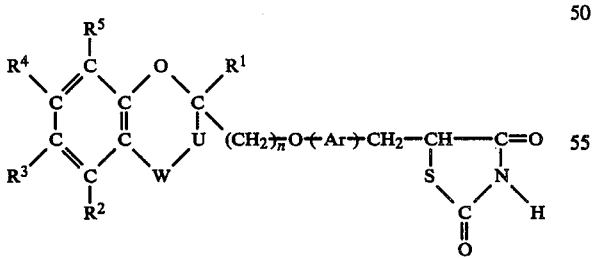

in which:

R$^1$ represents a hydrogen atom, a C$_1$-C$_{25}$ alkyl group, an aralkyl group, a C$_3$-C$_{10}$ cycloalkyl group or a substituted C$_3$-C$_{10}$ cycloalkyl group having at least one substituent selected from the group consisting of C$_1$-C$_6$ alkyl groups;

R$^2$, R$^4$ and R$^5$ are independently selected from the group consisting of: hydrogen atoms; C$_1$-C$_{25}$ alkyl groups; substituted C$_1$-C$_{25}$ alkyl groups having at least one substituent selected from the group consisting of substituents (a); aralkyl groups; C$_3$-C$_{10}$ cycloalkyl groups; substituted C$_3$-C$_{10}$ cycloalkyl groups having at least one substituent selected from the group consisting of C$_1$-C$_6$ alkyl groups; aryl groups; halogen atoms; hydroxy groups; protected hydroxy groups in which the protecting group is selected from the group consisting of substituents (b); C$_1$-C$_7$ alkanoyl groups; substituted C$_2$-C$_7$ alkanoyl groups having at least one substituent selected from the group consisting of substituents (c); arylcarbonyl groups; cycloalkylcarbonyl groups in which the cycloalkyl part is C$_3$-C$_{10}$; substituted cycloalkylcarbonyl groups in which the cycloalkyl part is C$_3$-C$_{10}$ and has at least one substituent selected from the group consisting of C$_1$-C$_6$ alkyl groups; carboxy groups; C$_2$-C$_7$ alkoxycarbonyl groups; aryloxycarbonyl groups; aralkyloxycarbonyl groups; nitro groups; groups of formula (II):

in which R$^7$ and R$^8$ are independently selected from the group consisting of hydrogen atoms, C$_1$-C$_6$ alkyl groups, aralkyl groups, C$_3$-C$_{10}$ cycloalkyl groups, aryl groups, C$_1$-C$_7$ alkanoyl groups, aralkanoyl groups, arylcarbonyl groups and C$_2$-C$_7$ alkoxycarbonyl groups, or R$^7$ and R$^8$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms, and groups of formula (III):

in which R$^{7'}$ and R$^{8'}$ are independently selected from the group consisting of hydrogen atoms, C$_1$-C$_6$ alkyl groups, aralkyl groups, C$_3$-C$_{10}$ cycloalkyl groups and aryl groups or R$^{7'}$ and R$^{8'}$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms;

R$^3$ represents a hydrogen atom, a C$_1$-C$_{25}$ alkyl group, a substituted C$_1$-C$_{25}$ alkyl group having at least one substituent selected from the group consisting of substituents (a), an aralkyl group, a C$_3$-C$_{10}$ cycloalkyl group, a substituted C$_3$-C$_{10}$ cycloalkyl group having at least one substituent selected from the group consisting of C$_1$-C$_6$ alkyl groups, an aryl group, a halogen atom, a C$_1$-C$_7$ alkanoyl group, a substituted C$_2$-C$_7$ alkanoyl group having at least one substituent selected from the group consisting of substituents (c), an arylcarbonyl group, a cycloalkylcarbonyl group in which the cycloalkyl part is $C_3$–$C_{10}$, a substituted cycloalkylcarbonyl group in which the cycloalkyl part is $C_3$–$C_{10}$ and has at least one substituent selected from the group consisting of $C_1$–$C_6$ alkyl groups, a carboxy group, a $C_2$–$C_7$ alkoxycarbonyl group, an aryloxycarbonyl group, an aralkyloxycarbonyl group, a nitro group, a group of formula (II) as defined above or a group of formula (III) as defined above;

Ar represents a divalent aromatic carbocyclic group or a divalent aromatic heterocyclic group;

W represents a methylene group, a carbonyl group, a group of formula $>CH-Oy$ in which Y represents a hydrogen atom, a $C_1$–$C_7$ alkanoyl group or an arylcarbonyl group, or a group of formula $>C=N-OV$ in which V represents a hydrogen atom, a $C_1$–$C_6$ alkyl group, a substituted $C_1$–$C_6$ alkyl group having at least one substituent selected from the group consisting of substituents (c), a $C_1$–$C_7$ alkanoyl group or an arylcarbonyl group;

U represents a single bond or a methylene group; or, when W represents a carbonyl group or said group of formula $>C=N-OV$, U, $R^1$ and the carbon atom to which $R^1$ is attached may together represent a group of formula $-CH=C<$;

or W-U may represent a carbon-carbon double bond; and n represents an integer from 1 to 10;

said aralkyl groups have an alkyl portion containing from 1 to 6 carbon atoms and an aryl portion as defined below, the alkyl portion being unsubstituted or having at least one substituent selected from the group consisting of substituents (c);

substituents (a):
hydroxy groups; protected hydroxy groups in which the protecting group is selected from the group consisting of substituents (b); $C_1$–$C_7$ aliphatic carboxylic acyl groups; $C_2$–$C_7$ aliphatic carboxylic acyl groups having at least one substituent selected from the group consisting of substituents (c); arylcarbonyl groups; cycloalkylcarbonyl groups in which the cycloalkyl part is $C_3$–$C_{10}$; substituted cycloalkylcarbonyl groups in which the cycloalkyl part is $C_3$–$C_{10}$ and having at least one substituent selected from the group consisting of $C_1$–$C_6$ alkyl groups; carboxy groups; $C_2$–$C_7$ alkoxycarbonyl groups; aryloxycarbonyl groups; aralkyloxycarbony groups; hydroxyimino groups; protected hydroxyimino groups in which the protecting group is selected from the group consisting of substituents (b); groups of formula (II) as defined above; and groups of formula (III) as defined above;

substituents (b);
$C_1$–$C_6$ alkyl groups, substituted $C_1$–$C_6$ alkyl groups having at least one substituent selected from the group consisting of substituents (c), $C_1$–$C_7$ aliphatic carboxylic acyl groups, substituted $C_2$–$C_7$ aliphatic carboxylic acyl groups having at least one substituent selected from the group consisting of substituents (c), arylcarbonyl groups, $C_2$–$C_7$ alkoxycarbonyl groups, aryloxycarbonyl groups, groups of formula (III) as defined above and sulfo groups;

substituents (c)
carboxy groups, $C_2$–$C_7$ alkoxycarbonyl groups and aryl groups;

said aryl groups and the aryl parts of said aralkyl arylcarbonyl, aryloxycarbonyl, aralkyloxycarbonyl and divalent aromatic groups being $C_6$–$C_{14}$ carbocyclic aryl groups which are unsubstituted or have at least one substituent selected from the group consisting of substituents (d);

said heterocyclic groups, heterocyclic parts of said heterocyclic acyl and acyloxy groups and said divalent heterocyclic aromatic groups have from 5 to 14 ring atoms, of which from 1 to 5 are heteroatoms selected from the group consisting of nitrogen, oxygen and sulfur hetero-atoms, said heterocyclic groups being unsubstituted or having at least one substituent selected from the group consisting of substituents (d) and substituents (e);

substituents (d)
$C_1$–$C_6$ alkyl groups, $C_1$–$C_6$ alkoxy groups, hydroxy groups, sulfoxy groups, halogen atoms, nitro groups, groups of formula (II), as defined above, $C_1$–$C_7$ aliphatic carboxylic acyl groups, $C_7$–$C_{11}$ aromatic carboxylic acyl groups, $C_1$–$C_7$ aliphatic carboxylic acylocy groups and $C_7$–$C_{11}$ arylcarbonyloxy groups in which the aryl part is unsubstituted or has at least one substituent selected from the group consisting of $C_1$–$C_6$ alkyl groups, $C_1$–$C_6$ alkoxy groups and halogen atoms;

substituents (e)
aryl groups and oxygen atoms; and pharmaceutically acceptable salts thereof.

2. A compound as claimed in claim 1, wherein:
$R^1$ represents a hydrogen atom or a $C_1$–$C_{10}$ alkyl group;

$R^2$, $R^4$ and $R^5$ are independently selected from the group consisting of: hydrogen atoms; $C_1$–$C_{10}$ alkyl groups; substituted $C_1$–$C_{10}$ alkyl groups having at least one substituent selected from the group consisting of substituents (a); aralkyl groups; aryl groups; halogen atoms; hydroxy groups; protected hydroxy groups in which the protecting group is selected from the group consisting of substituents (b); $C_1$–$C_6$ alkanoyl groups, substituted $C_2$–$C_6$ alkanoyl groups having at least one substituent selected from the group consisting of substituents (c); arylcarbonyl groups; carboxy groups; $C_2$–$C_7$ alkoxycarbonyl groups; nitro groups; groups of formula (II), as defined in claim 1, and groups of formula (III), as defined in claim 1.

$R^3$ represents a hydrogen atom, a $C_1$–$C_{10}$ alkyl group, a substituted $C_1$–$C_{10}$ alkyl group having at least one substituent selected from the group consisting of substituents (a), an aralkyl group, an aryl group, a halogen atom, a $C_1$–$C_6$ alkanoyl group, a substituted $C_2$–$C_6$ alkanoyl group having at least one substituent selected from the group consisting of substituents (c), an arylcarbonyl group, a carboxy group, a $C_2$–$C_7$ alkoxycarbonyl group, a nitro group, a group of formula (II) as defined in claim 1 or a group of formula (III) as defined in claim 1;

$R^7$ and $R^8$ are independently selected from the group consisting of hydrogen atoms, $C_1$–$C_6$ alkyl groups, aralkyl groups, aryl groups, $C_1$–$C_5$ alkanoyl groups and arylcarbonyl groups, or $R^7$ and $R^8$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms;

$R^{7'}$ and $R^{8'}$ are independently selected from the group consisting of hydrogen atoms, $C_1-C_6$ alkyl groups, aralkyl groups and aryl groups or $R^{7'}$ and $R^{8'}$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms, said heterocyclic group being unsubstituted or having at least one substituent selected from the group consisting of $C_1-C_6$ alkanoyl groups and arylcarbonyl groups;

Ar represents a phenylene group;

W represents a methylene group, a carbonyl group, a group of formula $>CH-OY$, in which Y is as defined in claim 1, or a group of formula $>C=N-OV$, in which V is as defined in claim 1;

U represents a methylene group;

or, when W represents a carbonyl group or said group of formula $>C=N-OV$, U, $R^1$ and the carbon atom to which $R^1$ is attached may together represent a group of formula $-CH=C<$;

or W-U may represent a carbon-carbon double bond; and n represents the integer 1, 2 or 3.

3. A compound as claimed in claim 1, wherein:
$R^1$ represents a $C_1-C_4$ alkyl group;
$R^2$, $R^4$ and $R^5$ are independently selected from the group consisting of: hydrogen atoms; $C_1-C_4$ alkyl groups; halogen atoms; hydroxy groups; protected hydroxy groups in which the protecting group is selected from the group consisting of substituents (b); $C_1-C_5$ alkanoyl groups; benzoyl groups; carboxy groups; $C_2-C_7$ alkoxycarbonyl groups; nitro groups; and amino groups;
$R^3$ represents a hydrogen atom, a $C_1-C_4$ alkyl group, a halogen atom, a $C_1-C_5$ alkanoyl group, a benzoyl group, a carboxy group, a $C_2-C_7$ alkoxycarbonyl group, a nitro group or an amino group;
Ar represents a phenylene group;
W represents a methylene group, a carbonyl group or a group of formula $>CH-OH$;
U represents a methylene group;
or W-U may represent a carbon-carbon double bond; and
n represents the integer 1, 2 or 3.

4. A compound as claimed in claim 1, wherein:
$R^1$ represents a $C_1-C_4$ alkyl group;
$R^2$, $R^4$ and $R^5$ are independently selected from the group consisting of: hydrogen atoms; $C_1-C_4$ alkyl groups; halogen atoms; hydroxy groups; protected hydroxy groups in which the protecting group is selected from the group consisting of substituents (f); $C_1-c_5$ alkanoyl groups; carboxy groups; $C_2-C_5$ alkoxycarbonyl groups; and nitro groups;
$R^3$ represents a hydrogen atom, a $C_1-C_4$ alkyl group, a halogen atom, a $C_1-C_5$ alkanoyl group, a carboxy group, a $C_2-C_5$ alkoxycarbonyl group or a nitro group;
Ar represents an unsubstituted 1,4-phenylene group;
W represents a methylene group or a carbonyl group;
U represents a methylene group;
or W-U may represent a carbon-carbon double bond; and
n represents the integer 1 or 2;
substituents (f):

$C_1-C_4$ alkyl groups having a single substituent selected from the group consisting of carboxy groups and $C_2C_5$ alkoxycarbonyl groups, $C_1-C_5$ alkanoyl groups and benzoyl groups.

5. A compound as claimed in claim 1, wherein:
$R^1$ represents a hydrogen atom or a $C_1-C_4$ alkyl group;
$R^2$ represents a hydrogen atom or a $C_1-C_4$ alkyl group;
$R^3$ represents a hydrogen atom, a $C_1-C_4$ alkyl group, a halogen atom, a $C_1-C_5$ alkanoyl group, a benzoyl group, a carboxy group, a $C_2-C_5$ alkoxycarbonyl group, or a nitro group;
$R^4$ represents a hydrogen atom, a $C_1-C_4$ alkyl group, a halogen atom, a hydroxy group or a protected hydroxy group in which the protecting group is selected from the group consisting of substituents (f);
$R^5$ represents a hydrogen atom, a $C_1-C_4$ alkyl group or a nitro group;
Ar represents a phenylene group;
W represents a methylene group or a carbonyl group;
U represents a methylene group;
or W-U may represent a carbon-carbon double bond; and
n represents the integer 1, 2 or 3;
substituents (f):
$C_1-C_4$ alkyl groups having a single substituent selected from the group consisting of carboxy groups and $C_2-C_5$ alkoxycarbonyl groups, $C_1-C_5$ alkanoyl groups and benzoyl groups.

6. A compound as claimed in claim 5, wherein:
$R^1$ represents a $C_1-C_4$ alkyl group; $R^2$ represents a hydrogen atom or a $C_1-C_4$ alkyl group;
$R^3$ represents a hydrogen atom, a $C_1-C_4$ alkyl group, a halogen atom, a $C_2-C_5$ alkanoyl group, a carboxy group, or a $C_2-C_5$ alkoxycarbonyl group;
$R^4$ represents a hydrogen atom, a $C_1-C_4$ alkyl group, a hydroxy group or a protected hydroxy group in which the protecting group is selected from the group consisting of substituents (f), defined in claim 5;
$R^5$ represents a hydrogen atom or a $C_1-C_4$ alkyl group;
Ar represents a phenylene group;
W represents a methylene group or a carbonyl group;
U represents a methylene group;
or W-U may represent a carbon-carbon double bond; and
n represents the integer 1 or 2.

7. A compound as claimed in claim 5, wherein: $R^1$ represents a $C_1-C_4$ alkyl group;
$R^2$ represents a hydrogen atom or a $C_1-C_4$ alkyl group;
$R^3$ represents a hydrogen atom, a $C_1-C_4$ alkyl group, a halogen atom, a $C_2-C_5$ alkanoyl group, a carboxy group or a $C_2-C_5$ alkoxycarbonyl group;
$R^4$ represents a hydrogen atom, a $C_1-C_4$ alkyl group, a hydroxy group or a protected hydroxy group in which the protecting group is selected from the group consisting of substituents (f), defined in claim 5;
$R^5$ represents a hydrogen atom or a $C_1-C_4$ alkyl group;
Ar represents an unsubstituted 1,4-phenylene group;
W represents a methylene group or a carbonyl group;
U represents a methylene group;

or W-U may represent a carbon-carbon double bond; and n represents the integer 1 or 2;

8. A compound as claimed in claim 1, selected from the group consisting of 5-[4-(2-methylchroman-2-ylmethoxy)-benzyl]thiazolidine-2,4-dione and pharmaceutically acceptable salts thereof.

9. A compound as claimed in claim 1, selected from the group consisting of 5-[4-(2,5,6,7,8-pentamethylchroman-2-ylmethoxy)benzyl]thiazolidine-2,4-dione and pharmaceutically acceptable salts thereof.

10. A compound as claimed in claim 1, selected from the group consisting of 2-[4-(2,4-dioxothiazolidin-5-ylmethyl)phenoxymethyl]-2,8-dimethyl-4-oxochroman-7-yloxyacetic acid and pharmaceutically acceptable salts thereof.

11. A compound as claimed in claim 1, selected from the group consisting of 2-[4-(2,4-dioxothiazolidin-5-ylmethyl)phenoxymethl]-2-methylchroman-6-carboxylic acid and pharmaceutically acceptable salts thereof.

12. A compound as claimed in claim 1, selected from the group consisting of 2-[4-(2,4-dioxothiazolidin-5-ylmethyl)phenoxymethyl]-2-methyl-4-oxochroman-6-carboxylic acid and pharmaceutically acceptable salts thereof.

13. A pharmaceutical composition comprising a pharmaceutically acceptable carrier or diluent and an amount effective to reduce blood lipid and blood glucose levels, of a compound of the formula (I):

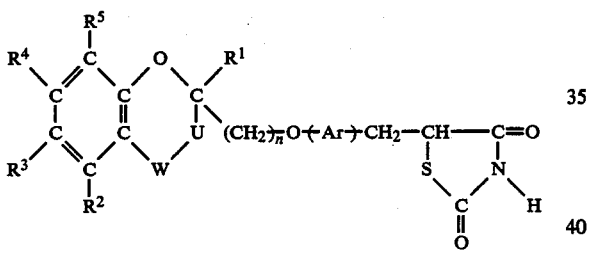

in which:

R$^1$ represents a hydrogen atom, a C$_1$-C$_{25}$ alkyl group, an aralkyl group, a C$_3$-C$_{10}$ cycloalkyl group or a substituted C$_3$-C$_{10}$ cycloalkyl group having at least one substituent selected from the group consisting of C$_1$-C$_6$ alkyl groups;

R$^2$, R$^4$ and R$^5$ are independently selected from the group consisting of: hydrogen atoms; C$_1$-C$_{25}$ alkyl groups; substituted C$_1$-C$_{25}$ alkyl groups having at least one substituent selected from the group consisting of substituents (a); aralkyl groups; C$_3$-C$_{10}$ cycloalkyl groups; substituted C$_3$-C$_{10}$ cycloalkyl groups having at least one substituent selected from the group consisting of C$_1$-C$_6$ alkyl groups; aryl groups; halogen atoms; hydroxy groups; protected hydroxy groups in which the protecting group is selected from the group consisting of substituents (b); C$_1$-C$_7$ alkanoyl groups; substituted C$_2$-C$_7$ alkanoyl groups having at least one substituent selected from the group consisting of substituents (c); arylcarbonyl groups; cycloalkylcarbonyl groups in which the cycloalkyl part is C$_3$-C$_{10}$; substituted cycloalkylcarbonyl groups in which the cycloalkyl part is C$_3$-C$_{10}$ and has at least one substituent selected from the group consisting of C$_1$-C$_6$ alkyl groups; carboxy groups; C$_2$-C$_7$ alkoxycarbonyl groups; aryloxycarbonyl groups; aralkyloxycarbonyl groups; nitro groups; groups of formula (II):

in which R$^7$ and R$^8$ are independently selected from the group consisting of hydrogen atoms, C$_1$-C$_6$ alkyl groups, aralkyl groups, C$_3$-C$_{10}$ cyclalkyl groups, aryl groups, C$_1$-C$_7$ alkanoyl groups, aralkanoyl groups, arylcarbonyl groups and C$_2$-C$_7$ alkoxycarbonyl groups, or R$^7$ and R$^8$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms, and groups of formula (III):

in which R$^{7'}$ and R$^{8'}$ are independently selected from the group consisting of hydrogen atoms, C$_1$-C$_6$ alkyl groups, aralkyl groups, C$_3$-C$_{10}$ cycloalkyl groups and aryl groups or R$^{7'}$ and R$^8$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms;

R$^3$ represents a hydrogen atom, a C$_1$-C$_{25}$ alkyl group, a substituted C$_1$-C$_{25}$ alkyl group having at least one substituent selected from the group consisting of substituents (a), an aralkyl group, a C$_3$-C$_{10}$ cycloalkyl group, a substituted C$_3$-C$_{10}$ cycloalkyl group having at least one substituent selected from the group consisting of C$_1$-C$_6$ alkyl groups, an aryl group, a halogen atom, a C$_1$-C$_7$ alkanoyl group, a substituted C$_2$-C$_7$ alkanoyl group having at least one substituent selected from the group consisting of substituents (c), an arylcarbonyl group, a cycloalkylcarbonyl group in which the cycloalkyl part is C$_3$-C$_{10}$, a substituted cycloalkylcarbonyl group in which the cycloalkyl part is C$_3$-C$_{10}$ and has at least one substituent selected from the group consisting of C$_1$-C$_6$ alkyl groups, a carboxy group, a C$_2$-C$_7$ alkoxycarbonyl group, an aryloxycarbonyl group, an aralkyloxycarbonyl group, a nitro group, a group of formula (II) as defined above or a group of formula (III) as defined above;

Ar represents a divalent aromatic carbocyclic group or a divalent aromatic heterocyclic group;

W represents a methylene group, a carbonyl group, a group of formula >CH—OY in which Y represents a hydrogen atom, a C$_1$-C$_7$ alkanoyl group or an arylcarbonyl group, or a group of formula >C=N—OV in which V represents a hydrogen atom, a C$_1$-C$_6$ alkyl group, a substituted C$_1$-C$_6$ alkyl group having at least one substituent selected from the group consisting of substituents (c), a C$_1$-C$_7$ alkanoyl group or an arylcarbonyl group;

U represents a single bond or a methylene group; or, when W represents a carbonyl group or said group of formula $>C=N-OV$, U, $R^1$ and the carbon atom to which $R^1$ is attached may together represent a group of formula $-CH=C<$;

or W-U may represent a carbon-carbon double bond; and n represents an integer from 1 to 10;

said aralkyl groups have an alkyl portion containing from 1 to 6 carbon atoms and an aryl portion as defined below, the alkyl portion being unsubstituted or having at least one substituent selected from the group consisting of substituents (c);

substituents (a):

hydroxy groups; protected hydroxy groups in which the protecting group is selected from the group consisting of substituents (b); $C_1$–$C_7$ aliphatic carboxylic acyl groups; $C_2$–$C_7$ aliphatic carboxylic acyl groups having at least one substituent selected from the group consisting of substituents (c); arylcarbonyl groups; cycloalkylcarbonyl groups in which the cycloalkyl part is $C_3$–$C_{10}$; substituted cycloalkylcarbonyl groups in which the cycloalkyl part is $C_3$–$C_{10}$ and having at least one substituent selected from the group consisting of $C_1$–$C_6$ alkyl groups; carboxy groups; $C_2$–$C_7$ alkoxycarbonyl groups; aryloxycarbonyl groups; aralkyloxycarbonyl groups; hydroxyimino groups; protected hydroxyimino groups in which the protecting group is selected from the group consisting of substituents (b); groups of formula (II) as defined above; and groups of formula (III) as defined above;

substituents (b):

$C_1$–$C_6$ alkyl groups, substituted $C_1$–$C_6$ alkyl groups having at least one subtituent selected from the group consisting of substituents (c), $C_1$–$C_7$ aliphatic carboxylic acyl groups, substituted $C_2$–$C_7$ aliphatic carboxylic acyl groups having at least one substituent selected from the group consisting of substituents (c), arylcarbonyl groups, $C_2$–$C_7$ alkoxycarbonyl groups, aryloxycarbonyl groups, groups of formula (III) as defined above and sulfo groups;

substituents (c)

carboxy groups, $C_2$–$C_7$ alkoxycarbonyl groups and aryl groups;

said aryl groups and the aryl parts of said aralkyl, arylcarbonyl, arloxycarbonyl, aralkyloxycarbonyl and divalent aromatic groups being $C_6$–$C_{14}$ carbocyclic aryl groups which are unsubstituted or have at least one substituent selected from the group consisting of substituents (d);

said heterocyclic groups, heterocyclic parts of said heterocyclic acyl and acyloxy groups and said divalent heterocyclic aromatic groups have from 5 to 14 ring atoms, of which from 1 to 5 are heteroatoms selected from the group consisting of nitrogen, oxygen and sulfur hetero-atoms, said heterocyclic groups being unsubstituted or having at least one substituent selected from the group consisting of substituents (d) and subtituents (e);

substituents (d)

$C_1$–$C_6$ alkyl groups, $C_1$–$C_6$ alkoxy groups, hydroxy groups, sulfoxy groups, halogen atoms, nitro groups, groups of formula (II), as defined above, $C_1$–$C_7$ aliphatic carboxylic acyl groups, $C_7$–$C_{11}$ aromatic carboxylic acyl groups, $C_1$–$C_7$ aliphatic carboxylic acyloxy groups and $C_7$–$C_{11}$ arylcarbonyloxy groups in which the aryl part is unsubstituted or has at least one substituent selected from the group consisting of $C_1$–$C_6$ alkyl groups, $C_1$–$C_6$ alkoxy groups and halogen atoms;

substituents (e)

aryl groups and oxygen atoms; and pharmaceutically acceptable salts thereof.

14. A composition as claimed in claim 13, wherein:

$R^1$ represents a hydrogen atom or a $C_1$–$C_{10}$ alkyl group;

$R^2$, $R^4$ and $R^5$ are independently selected from the group consisting of: hydrogen atoms; $C_1$–$C_{10}$ alkyl groups; substituted $C_1$–$C_{10}$ alkyl groups having at least one substituent selected from the group consisting of substituents (a); aralkyl groups; aryl groups; halogen atoms; hydroxy groups; protected hydroxy groups in which the protecting group is selected from the group consisting of substituents (b); $C_1$–$C_6$ alkanoyl groups; substituted $C_2$–$C_6$ alkanoyl groups having at least one substituent selected from the group consisting of substituents (c); arylcarbonyl groups; carboxy groups; $C_2$–$C_7$ alkoxycarbonyl groups; nitro groups; groups of formula (II), as defined in claim 13, and groups of formula (III), as defined in claim 13;

$R^3$ represents a hydrogen atom, a $C_1$–$C_{10}$ alkyl group, a substituted $C_1$–$C_{10}$ alkyl group having at least one substituent selected from the group consisting of substituents (a), an aralkyl group, an aryl group, a halogen atom, a $C_1$–$C_6$ alkanoyl group, a substituted $C_2$–$C_6$ alkanoyl group having at least one substituent selected from the group consisting of substituents (c), an arylcarbonyl group, a carboxy group, a $C_2$–$C_7$ alkoxycarbonyl group, a nitro group, a group of formula (II) as defined in claim 13 or a group of formula (III) as defined in claim 13;

$R^7$ and $R^8$ are independently selected from the group consisting of hydrogen atoms, $C_1$–$C_6$ alkyl groups, aralkyl groups, aryl groups, $C_1$–$C_5$ alkanoyl groups and arylcarbonyl groups, or $R^7$ and $R^8$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms;

$R^{7'}$ and $R^{8'}$ are independently selected from the group consisting of hydrogen atoms, $C_1$–$C_6$ alkyl groups, aralkyl groups and aryl groups or $R^{7'}$ and $R^{8'}$, together with the nitrogen atom to which they are attached, form a nitrogen-containing heterocyclic group having from 5 to 7 ring atoms, of which one is said nitrogen atom and from 0 to 2 are additional hetero-atoms selected from the group consisting of nitrogen, oxygen and sulfur hetero-atoms, said heterocyclic group being unsubstituted or having at least one substituent selected from the group consisting of $C_1$–$C_6$ alkanoyl groups and arylcarbonyl groups;

Ar represents a phenylene group;

W represents a methylene group, a carbonyl group, a group of formula $>CH-OY$, in which Y is as defined in claim 13, or a group of formula $>C=N-OV$, in which V is as defined in claim 13;

U represents a methylene group;

or, when W represents a carbonyl group or said group of formula >C=N—OV, U, R¹ and the carbon atom to which R¹ is attached may together represent a group of formula —CH=C<;
or W-U may represent a carbon-carbon double bond; and n represents the integer 1, 2 or 3.

15. A composition as claimed in claim 13, wherein:
R¹ represents a C₁-C₄ alkyl group;
R², R⁴ and R⁵ are independently selected from the group consisting of: hydrogen atoms; C₁-C₄ alkyl groups; halogen atoms; hydroxy groups; protected hydroxy groups in which the protecting group is selected from the group consisting of substituents (f); C₁-C₅ alkanoyl groups; carboxy groups; C₂-C₅ alkoxycarbonyl groups; and nitro groups;
R³ represents a hydrogen atom, a C₁-C₄ alkyl group, a halogen atom, a C₁-C₅ alkanoyl group, a carboxy group, a C₁-C₅ alkoxycarbonyl group or a nitro group;
Ar represents an unsubstituted 1,4-phenylene group;
W represents a methylene group or a carbonyl group;
U represents a methylene group;
or W-U may represent a carbon-carbon double bond; and n represents the integer 1 or 2;
substituents (f):
C₁-C₄ alkyl groups having a single substituent selected from the group consisting of carboxy groups and C₂-C₅ alkoxycarbonyl groups, C₁-C₅ alkanoyl groups and benzoyl groups.

16. A composition as claimed in claim 15, wherein:
R¹ represents a C₁-C₄ alkyl group;
R² represents a hydrogen atom or a C₁-C₄ alkyl group;
R³ represents a hydrogen atom, a C₁-C₄ alkyl group, a halogen atom, a C₂-C₅ alkanoyl group, a carboxy group, or a C₂-C₅ alkoxycarbonyl group;
R⁴ represents a hydrogen atom, a C₁-C₄ alkyl group, a hydroxy group or a protected hydroxy group in which the protecting group is selected from the group consisting of substituents (f), defined in claim 15;
R⁵ represents a hydrogen atom or a C₁-C₄ alkyl group;
Ar represents a phenylene group;
W represents a methylene group or a carbonyl group;
U represents a methylene group;
or W-U may represent a carbon-carbon double bond; and n represents the integer 1 or 2.

17. A composition as claimed in claim 15, wherein:
R¹ represents a C₁-C₄ alkyl group;
R² represents a hydrogen atom or a C₁-C₄ alkyl group;
R³ represents a hydrogen atom, a C₁-C₄ *alkyl group, a halogen atom, a* C₂-C₅ alkanoyl group, a carboxy group or a C₂-C₅ alkoxycarbonyl group;
R⁴ represents a hydrogen atom, a C₁-C₄ alkyl group, a hydroxy group or a protected hydroxy group in which the protecting group is selected from the group consisting of substituents (f), defined in claim 15;
R⁵ represents a hydrogen atom or a C₁-C₄ alkyl group;
Ar represents an unsubstituted 1,4-phenylene group;
W represents a methylene group or a carbonyl group;

U represents a methylene group;
or W-U may represent a carbon-carbon double bond; and n represents the integer 1 or 2;

18. A composition as claimed in claim 13, wherein said compound is selected from the group consisting of
5-[-(2-methylchroman-2-ylmethoxy)benzyl]thiazolidine-2,4-dione;
5-[4-(2,5,6,7,8-pentamethylchroman-2-ylmethoxy)-benzyl]-thiazolidine-2,4-dione;
2-[4-(2,4-dioxothiazolidin-5-ylmethyl)phenoxymethyl]-2,8-dimethyl-4-oxochroman-7-yloxyacetic acid;
2-[4-(2,4-dioxothiazolidin-5-ylmethyl)phenoxymethyl]-2-methylchroman-6-carboxylic acid; and
2[4-(2,4-dioxothiazolidin-5-ylmethyl)phenoxymethyl]-2-methyl-4-oxochroman-6-carboxylic acid;
and pharmaceutically acceptable salts thereof.

19. A method of reducing blood lipid and blood glucose levels in an animal by administering to said animal an effective amount of a compound selected from the group consisting of compounds of formula (I):

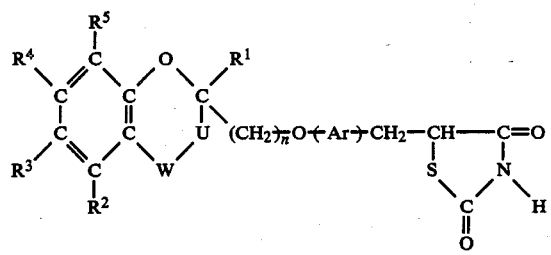

in which:
R¹ represents a hydrogen atom, a C₁-C₂₅ alkyl group, an aralkyl group, a C₃-C₁₀ cycloalkyl group or a substituted C₃-C₁₀ cycloalkyl group having at least one substituent selected from the group consisting of C₁-C₆ alkyl groups;
R², R⁴ and R⁵ are independently selected from the group consisting of: hydrogen atoms; C₁-C₂₅ alkyl groups; substituted C₁-C₂₅ alkyl groups having at least one substituent selected from the group consisting of substituents (a); aralkyl groups; C₃-C₁₀ cycloalkyl groups; substituted C₃-C₁₀ cycloalkyl groups having at least one substituent selected from the group consisting of C₁-C₆ alkyl groups; aryl groups; halogen atoms; hydroxy groups; protected hydroxy groups in which the protecting group is selected from the group consisting of substituents (b); C₁-C₇ alkanoyl groups; substituted C₂-C₇ alkanoyl groups having at least one substituent selected from the group consisting of substituents (c); arylcarbonyl groups; cycloalkylcarbonyl groups in which the cycloalkyl part is C₃-C₁₀; substituted cycloalkylcarbonyl groups in which the cycloalkyl part is C₃-C₁₀ and has at least one substituent selected from the group consisting of C₁-C₆ alkyl groups; carboxy groups; C₂-C₇ alkoxycarbonyl groups; aryloxycarbonyl groups; aralkyloxycarbonyl groups; nitro groups; groups of formula (II):

in which $R^7$ and $R^8$ are independently selected from the group consisting of hydrogen atoms, $C_1$-$C_6$ alkyl groups, aralkyl groups, $C_3$-$C_{10}$ cycloalkyl groups, aryl groups, $C_1$-$C_7$ alkanoyl groups, aralkanoyl groups, arylcarbonyl groups and $C_2$-$C_7$ alkoxycarbonyl groups, or $R^7$ and $R^8$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms, and groups of formula (III):

in which $R^{7'}$ and $R^{8'}$ are independently selected from the group consisting of hydrogen atoms, $C_1$-$C_6$ alkyl groups, aralkyl groups, $C_3$-$C_{10}$ cycloalkyl groups and aryl groups or $R^{7'}$ and $R^{8'}$, together with the nitrogen atom to which they are attached, form a nitrogen-containing heterocyclic group having from 5 to 10 ring atoms, of which one is said nitrogen atom and from 0 to 3 are additional hetero-atoms selected from the group consisting of nitrogen, oxygen and sulfur hetero-atoms;

$R^3$ represents a hydrogen atom, a $C_1$-$C_{25}$ alkyl group, a substituted $C_1$-$C_{25}$ alkyl group having at least one substituent selected from the group consisting of substituents (a), an aralkyl group, a $C_3$-$C_{10}$ cycloalkyl group, a substituted $C_3$-$C_{10}$ cycloalkyl group having at least one substituent selected from the group consisting of $C_1$-$C_6$ alkyl groups, an aryl group, a halogen atom, a $C_1$-$C_7$ alkanoyl group, a substituted $C_2$-$C_7$ alkanoyl group having at least one substituent selected from the group consisting of substituents (c), an arylcarbonyl group, a cycloalkylcarbonyl group in which the cycloalkyl part is $C_3$-$C_{10}$, a substituted cycloalkylcarbonyl group in which the cycloalkyl part is $C_3$-$C_{10}$ and has at least one substituent selected from the group consisting of $C_1$-$C_6$ alkyl groups, a carboxy group, a $C_2$-$C_7$ alkoxycarbonyl group, an aryloxycarbonyl group, an aralkyloxycarbonyl group, a nitro group, a group of formula (II) as defined above or a group of formula (III) as defined above;

Ar represents a divalent aromatic carbocyclic group or a divalent aromatic heterocyclic group;

W represents a methylene group, a carbonyl group, a group of formula $>$CH—OY in which Y represents a hydrogen atom, a $C_1$-$C_7$ alkanoyl group or an arylcarbonyl group, or a group of formula $>$C=N—OV in which V represents a hydrogen atom, a $C_1$-$C_6$ alkyl group, a substituted $C_1$-$C_6$ alkyl group having at least one substituent selected from the group consisting of substituents (c), a $C_1$-$C_7$ alkanoyl group or an arylcarbonyl group;

U represents a single bond or a methylene group;

or, when W represents a carbonyl group or said group of formula $>$C=N—OV, U, $R^1$ and the carbon atom to which $R^1$ is attached may together represent a group of formula —CH=C$<$;

or W-U may represent a carbon-carbon double bond; and n represents an integer from 1 to 10;

said aralkyl groups have an alkyl portion containing from 1 to 6 carbon atoms and an aryl portion as defined below, the alkyl portion being unsubstituted or having at least one substituent selected from the group consisting of substituents (c);

substituents (a):

hydroxy groups; protected hydroxy groups in which the protecting group is selected from the group consisting of substituents (b); $C_1$-$C_7$ aliphatic carboxylic acyl groups; $C_2$-$C_7$ aliphatic carboxylic acyl groups having at least one substituent selected from the group consisting of substituents (c); arylcarbonyl groups; cycloalkylcarbonyl groups in which the cycloalkyl part is $C_3$-$C_{10}$; substituted cycloalkylcarbonyl groups in which the cycloalkyl part is $C_3$-$C_{10}$ and having at least one substituent selected from the group consisting of $C_1$-$C_6$ alkyl groups; carboxy groups; $C_2$-$C_7$ alkoxycarbonyl groups; aryloxycarbonyl groups; aralkyloxycarbonyl groups; hydroxyimino groups; protected hydroximino groups in which the protecting group is selected from the group consisting of substituents (b); groups of formula (II) as defined above; and groups of formula (III) as defined above;

substituents (b):

$C_1$-$C_6$ alkyl groups, substituted $C_1$-$C_6$ alkyl groups having at least one substituent selected from the group consisting of substituents (c), $C_1$-$C_7$ aliphatic carboxylic acyl groups, substituted $C_2$-$C_7$ aliphatic carboxylic acyl groups having at least one substituent selected from the group consisting of substituents (c), arylcarbonyl groups, $C_2$-$C_7$ alkoxycarbonyl groups, aryloxycarbonyl groups, groups of formula (III) as defined above and sulfo groups; substituents (c)

carboxy groups, $C_2$-$C_7$ alkoxycarbonyl groups and aryl groups;

said aryl groups and the aryl parts of said aralkyl, araylcarbonyl, aryloxycarbonyl, aralkyloxycarbonyl and divalent aromatic groups being $C_6$-$C_{14}$ carbocyclic aryl groups which are unsubstituted or have at least one substituent selected from the group consisting of substituents (d);

said heterocyclic groups, heterocyclic parts of said heterocyclic acyl and acyloxy group and said divalent heterocyclic aromatic groups have from 5 to 14 ring atoms, of which from 1 to 5 are heteroatoms selected from the group consisting of nitrogen, oxygen and sulfur hetero-atoms, said heterocyclic groups being unsubstituted or having at least one subtituent selected from the group consisting of substituents (d) and substituents (e);

substituents (d)

$C_1$-$C_6$ alkyl groups, $C_1$-$C_6$ alkoxy groups, hydroxy groups, sulfoxy groups, halogen atoms, nitro groups, groups of formula (II), as defined above, $C_1$-$C_7$ aliphatic carboxylic acyl groups, $C_1$-$C_{11}$ aromatic carboxylic acyl groups, $C_1$-$C_7$ aliphatic carboxylic acyloxy groups and $C_7$-$C_{11}$ arylcarbonyloxy groups in which the aryl part is unsubstituted or has at least one substituent selected from the group consisting of $C_1-C_6$ alkyl groups, $C_1-C_6$ alkoxy groups and halogen atoms; substituents (e) aryl groups and oxygen atoms; and pharmaceutically acceptable salts thereof.

20. A method as claimed in claim 19, wherein:
$R^1$ represents a $C_1-C_4$ alkyl group;
$R^2$, $R^4$ and $R^5$ are independently selected from the group consisting of: hydrogen atoms; $C_1-C_4$ alkyl groups; halogen atoms; hydroxy groups; protected hydroxy groups in which the protecting group is selected from the group consisting of substituents (f); $C_1-C_5$ alkanoyl groups; carboxy groups; $C_2-C_5$ alkoxycarbonyl groups; and nitro groups;
$R^3$ represents a hydrogen atom, a $C_1-C_4$ alkyl group, a halogen atom, a $C_1-C_5$ alkanoyl group, a carboxy group, a $C_2-C_5$ alkoxycarbonyl group or a nitro group;
Ar represents an unsubstituted 1,4-phenylene group;
W represents a methylene group or a carbonyl group;
U represents a methylene group;
or W-U may represent a carbon-carbon double bond; and
n represents the integer 1 or 2;
substituents (f):
$C_1-C_4$ alkyl groups having a single substituent selected from the group consisting of carboxy groups and $C_2-C_5$ *alkoxycarbonyl groups*, $C_1-C_5$ alkanoyl groups and benzoyl groups.

21. A method as claimed in claim 20, wherein:
$R^1$ represents $C_1-C_4$ alkyl group;
$R^2$ represents a hydrogen atom or a $C_1-C_4$ alkyl group;
$R^3$ represents a hydrogen atom, a $C_1-C_4$ alkyl group, a halogen atom, a $C_2-C_5$ alkanoyl group, a carboxy group or a $C_2-C_5$ alkoxycarbonyl group;
$R^4$ represents a hydrogen atom, a $C_1-C_4$ alkyl group, a hydroxy group or a protected hydroxy group in which the protecting group is selected from the group consisting of substituents (f), defined in claim 20;
$R^5$ represents a hydrogen atom or a $C_1-C_4$ alkyl group;
Ar represents an unsubstituted 1,4-phenylene group;
W represents a methylene group or a carbonyl group;
U represents a methylene group;
or W-U may represent a carbon-carbon double bond; and
n represents the integer 1 or 2;

22. A method as claimed in claim 19, wherein said active compound is selected from the group consisting of
5-]4-(2-methylchroman-2-ylmethoxy)benzyl]thiazolidine-2,4-dione;
5-]4-(2,5,6,7,8-pentamethylchroman-2-ylmethoxy)-benzyl]-thiazolidine-2,4-dione;
2-[4-(2,4-dioxothiazolidin-5-ylmethyl)phenoxymethyl]-2,8-dimethyl-4-oxochroman-7-yloxyacetic acid;
2-[4-(2,4-dioxothiazolidin-5-ylmethyl)phenoxymethyl]-2-methylchroman-6-carboxylic acid; and
2-[4-(2,4-dioxothiazolidin-5-ylmethyl)phenoxymethyl]-2-methyl-4-oxochroman-6-carboxylic acid; and pharmaceutically acceptable salts thereof.

* * * * *